(12) United States Patent
Rimseliene et al.

(10) Patent No.: US 10,273,530 B2
(45) Date of Patent: Apr. 30, 2019

(54) ANTIBODIES THAT BIND THERMOPHILIC DNA POLYMERASES

(71) Applicant: Thermo Fisher Scientific Baltics UAB, Vilnius (LT)

(72) Inventors: Renata Rimseliene, Vilnius (LT); Donata Ulcinaite, Vilnius (LT); Birute Gagiliene, Vilnius (LT); Rasa Sukackaite, Vilnius (LT); Aurelija Zvirbliene, Vilnius (LT); Indre Kucinskaite-Kodze, Vilnius (LT); Dovile Dekaminaviciute, Vilnius (LT)

(73) Assignee: Thermo Fisher Scientific Baltics UAB, Vilnius (LT)

( * ) Notice: Subject to any disclaimer, the term of this patent is extended or adjusted under 35 U.S.C. 154(b) by 0 days.

(21) Appl. No.: 15/405,580

(22) Filed: Jan. 13, 2017

(65) Prior Publication Data

US 2017/0204454 A1 Jul. 20, 2017

Related U.S. Application Data

(60) Provisional application No. 62/279,426, filed on Jan. 15, 2016.

(51) Int. Cl.
| | | |
|---|---|---|
| *C12Q 1/6848* | (2018.01) | |
| *C07K 16/12* | (2006.01) | |
| *C07K 16/40* | (2006.01) | |
| *C12Q 1/686* | (2018.01) | |
| *C12N 9/12* | (2006.01) | |
| *C12Q 1/68* | (2018.01) | |

(52) U.S. Cl.
CPC ............ *C12Q 1/6848* (2013.01); *C07K 16/12* (2013.01); *C07K 16/40* (2013.01); *C12N 9/1252* (2013.01); *C12Q 1/686* (2013.01); *C07K 2317/56* (2013.01); *C07K 2317/565* (2013.01); *C07K 2317/76* (2013.01); *C07K 2317/92* (2013.01)

(58) Field of Classification Search
CPC .................................................... C12Q 1/6848
USPC .......................................................... 435/6
See application file for complete search history.

(56) References Cited

U.S. PATENT DOCUMENTS

| | | |
|---|---|---|
| 5,489,523 A | 2/1996 | Mathur |
| 6,627,424 B1 | 9/2003 | Wang |
| 7,074,556 B2 | 7/2006 | Li et al. |
| 7,541,170 B2 | 6/2009 | Wang et al. |
| 7,560,260 B2 | 7/2009 | Vander Horn et al. |
| 7,919,296 B2 | 4/2011 | Wang |
| 8,367,376 B2 | 2/2013 | Vander Horn et al. |
| 8,697,410 B2 | 4/2014 | Cheng |
| 8,859,205 B2 | 10/2014 | Gong et al. |
| 8,916,352 B2 | 12/2014 | Cheng et al. |
| 9,145,550 B2 | 9/2015 | Vander Horn et al. |
| 2013/0089895 A1 | 4/2013 | Martin et al. |
| 2013/0164817 A1 | 6/2013 | Martin et al. |

FOREIGN PATENT DOCUMENTS

| | | |
|---|---|---|
| EP | 0592035 | 4/1994 |
| EP | 2902488 | 8/2015 |
| JP | 11-75847 | 3/1999 |
| WO | WO-2007/016702 | 2/2007 |
| WO | WO-2010/080910 | 7/2010 |
| WO | WO-2012/115464 | 8/2012 |
| WO | WO-2015/061714 | 4/2015 |
| WO | WO 2012/177695 | 12/2015 |
| WO | WO-2017/121836 | 7/2017 |

OTHER PUBLICATIONS

NCBI cd05779: DNA_polB_epsilon_exo Oct. 1, 2007.*
Advantages of immunoglobulin F(ab) and F(ab')2 fragments 1998.*
Daiss, et al., "Topographical characterization of the DNA polymerase from Thermus aquaticus Defining groups of inhibitor mAbs by epitope mapping and functional analysis using surface plasmon resonance", *Journal of Immunological Methods*, vol. 183, No. 1, 1995, 15-26.
Kellogg, et al., "TaqStart Antibody(TM): "Hot Start" PCR Facilitated by a Neutralizing DNA Polymerase", *BioTechniques*, vol. 16, No. 6, 1994, 1134-1137.
Kennedy, et al., "The Mechanistic Architecture of the Thermostable Pyrococcus Furiosus Family B DNA Polymerase Motif A and its Interaction with dNTP Substrate", *NIH Public Access Author Manuscript*. Published in final edited form as: Biochemistry. Dec. 1, 2009; 48(47): 11161-11168, May 18, 2011, 17 Pages.
Mizuguchi, et al., "Characterization and Application to Hot Start PCR of Neutralizing Monoclonal Antibodies against KOD DNA Polymerase", *The Journal of Biochemistry*, vol. 126, No. 4, 1999, 762-768.
PCT/EP2017/050648, "International Search Report mailed", dated Apr. 11, 2017, 6 Pages.
Scalice, et al., "Monoclonal antibodies prepared against the DNA polymerase from Thermus aquaticus are potent inhibitors of enzyme activity", *Journal of Immunological Methods*, vol. 172, No. 2, 1994, 147-163.
Anonymous, "REFSEQ:WP_013143881", May 26, 2013.

(Continued)

*Primary Examiner* — Jana A Hines
*Assistant Examiner* — Khatol S Shahnan Shah

(57) ABSTRACT

This disclosure relates to antibodies that bind thermophilic family B DNA polymerases. Related uses, methods, and compositions are also provided.

16 Claims, 4 Drawing Sheets
Specification includes a Sequence Listing.

(56) References Cited

OTHER PUBLICATIONS

Kennedy, et al., "The Mechanistic Architecture of Thermostable Pyrococcus Furiosus Family B DNA Polymerase Motif A and Its Interaction with the dNTP Substrate", *Biochemistry*, vol. 48, No. 47, Dec. 1, 2009, 11161-11168.
Tubeleviciute, et al., "Compartmentalized self-replication (CSR) selection of Thermococcus litoralis Sh1B DNA polymerase for diminished uracil binding", *Protein Engineering, Design & Selection*, vol. 23, No. 8, May 31, 2010, 589-597.

\* cited by examiner

| | |
|---|---|
| Tli | MILDTDYITKDGKPIIRIFKKENGEFKIELDPHFQPYIYALLKDDSAIEEIKAIKGERHG |
| Tsp9N7 | MILDTDYITENGKPVIRVFKKENGEFKIEYDRTFEPYFYALLKDDSAIEDVKKVTAKRHG |
| Tgo | MILDTDYITEDGKPVIRIFKKENGEFKIDYDRNFEPYIYALLKDDSAIEDVKKITAERHG |
| Tko | MILDTDYITEDGKPVIRIFKKENGEFKIEYDRTFEPYFYALLKDDSAIEEVKKITAERHG |
| Pfu | MILDVDYITEEGKPVIRLFKKENGKFKIEHDRTFRPYIYALLRDDSKIEEVKKITGERHG |
| DV | MILDADYITEDGKPIIRIFKKENGEFKVEYDRNFRPYIYALLKDDSQIDEVRKITAERHG |
| | |
| Tli | KTVRVLDAVKVRKKFLGREVEVWKLIFEHPQDVPAMRGKIREHPAVVDIYEYDIPFAKRY |
| Tsp9N7 | TVVKVKRAEKVQKKFLGRPIEVWKLYFNHPQDVPAIRDRIRAHPAVVDIYEYDIPFAKRY |
| Tgo | TTVRVVRAEKVKKKFLGRPIEVWKLYFTHPQDVPAIRDKIKEHPAVVDIYEYDIPFAKRY |
| Tko | TVVTVKRVEKVQKKFLGRPVEVWKLYFTHPQDVPAIRDKIREHPAVIDIYEYDIPFAKRY |
| Pfu | KIVRIVDVEKVEKKFLGKPITVWKLYLEHPQDVPTIREKVREHPAVVDIFEYDIPFAKRY |
| DV | KIVRIIDAEKVRKKFLGRPIEVWRLYFEHPQDVPAIRDKIREHSAVIDIFEYDIPFAKRY |
| | |
| Tli | LIDKGLIPMEGDEELKLLAFDIETFYHEGDEFGKGEIIMISYADEEEARVITWKNIDLPY |
| Tsp9N7 | LIDKGLIPMEGDEELTMLAFDIETLYHEGEEFGTGPILMISYADGSEARVITWKKIDLPY |
| Tgo | LIDKGLIPMEGDEELKMLAFDIETLYHEGEEFAEGPILMISYADEEGARVITWKNIDLPY |
| Tko | LIDKGLVPMEGDEELKMLAFDIETLYHEGEEFAEGPILMISYADEEGARVITWKNVDLPY |
| Pfu | LIDKGLIPMEGEEELKILAFDIETLYHEGEEFGKGPIIMISYADENEAKVITWKNIDLPY |
| DV | LIDKGLIPMEGDEELKLLAFDIETLYHEGEEFAKGPIIMISYADEEEAKVITWKKIDLPY |
| | |
| Tli | VDVVSNEREMIKRFVQVVKEKDPDVIITYNGDNFDLPYLIKRAEKLGVRLVLGRDKEHPE |
| Tsp9N7 | VDVVSTEKEMIKRFLRVVREKDPDVLITYNGDNFDFAYLKKRCEELGIKFTLGRDG--SE |
| Tgo | VDVVSTEKEMIKRFLKVVKEKDPDVLITYNGDNFDFAYLKKRSEKLGVKFILGREG--SE |
| Tko | VDVVSTEREMIKRFLRVVKEKDPDVLITYNGDNFDFAYLKKRCEKLGINFALGRDG--SE |
| Pfu | VEVVSSEREMIKRFLRIIREKDPDIIVTYNGDSFDFPYLAKRAEKLGIKLTIGRDG--SE |
| DV | VEVVSSEREMIKRFLKVIREKDPDVIITYNGDSFDLPYLVKRAEKLGIKLPLGRDG--SE |
| | |
| Tli | PKIQRMGDSFAVEIKGRIHFDLFPVVRRTINLPTYTLEAVYEAVLGKTKSKLGAEEIAAI |
| Tsp9N7 | PKIQRMGDRFAVEVKGRIHFDLYPVIRRTINLPTYTLEAVYEAVFGKPKEKVYAEEIAQA |
| Tgo | PKIQRMGDRFAVEVKGRIHFDLYPVIRRTINLPTYTLEAVYEAIFGQPKEKVYAEEIAQA |
| Tko | PKIQRMGDRFAVEVKGRIHFDLYPVIRRTINLPTYTLEAVYEAVFGQPKEKVYAEEITTA |
| Pfu | PKMQRIGDMTAVEVKGRIHFDLYHVITRTINLPTYTLEAVYEAIFGKPKEKVYADEIAKA |
| DV | PKMQRLGDMTAVEIKGRIHFDLYHVIRRTINLPTYTLEAVYEAIFGKPKEKVYAHEIAEA |
| | |
| Tli | WETEESMKKLAQYSMEDARATYELGKEFFPMEAELAKLIGQSVWDVSRSSTGNLVEWYLL |
| Tsp9N7 | WESGEGLERVARYSMEDAKVTYELGREFFPMEAQLSRLIGQSLWDVSRSSTGNLVEWFLL |
| Tgo | WETGEGLERVARYSMEDAKVTYELGKEFFPMEAQLSRLVGQSLWDVSRSSTGNLVEWFLL |
| Tko | WETGENLERVARYSMEDAKVTYELGKEFLPMEAQLSRLIGQSLWDVSRSSTGNLVEWFLL |
| Pfu | WESGENLERVAKYSMEDAKATYELGKEFLPMEIQLSRLVGQPLWDVSRSSTGNLVEWFLL |
| DV | WETGKGLERVAKYSMEDAKVTYELGREFFPMEAQLSRLVGQPLWDVSRSSTGNLVEWYLL |
| | |
| Tli | RVAYARNELAPNKPDEEEYKRRLRTTYLGGYVKEPEKGLWENIIYLDFRSLYPSIIVTHN |
| Tsp9N7 | RKAYKRNELAPNKPDERELARR-RGGYAGGYVKEPERGLWDNIVYLDFRSLYPSIIITHN |
| Tgo | RKAYERNELAPNKPDERELARR-RESYAGGYVKEPERGLWENIVYLDFRSLYPSIIITHN |
| Tko | RKAYERNELAPNKPDEKELARR-RQSYEGGYVKEPERGLWENIVYLDFRSLYPSIIITHN |
| Pfu | RKAYERNEVAPNKPSEEEYQRRLRESYTGGFVKEPEKGLWENIVYLDFRALYPSIIITHN |
| DV | RKAYERNELAPNKPDEREYERRLRESYAGGYVKEPEKGLWEGLVSLDFRSLYPSIIITHN |

*FIG. 1A*

```
Tli     VSPDTLEKEGCKNYDVAPIVGYRFCKDFPGFIPSILGDLIAMRQDIKKKMKSTIDPIEKK
Tsp9N7  VSPDTLNREGCKEYDVAPEVGHKFCKDFPGFIPSLLGDLLEERQKIKRKMKATVDPLEKK
Tgo     VSPDTLNREGCEEYDVAPQVGHKFCKDFPGFIPSLLGDLLEERQKVKKKMKATIDPIEKK
Tko     VSPDTLNREGCKEYDVAPQVGHRFCKDFPGFIPSLLGDLLEERQKIKKKMKATIDPIERK
Pfu     VSPDTLNLEGCKNYDIAPQVGHKFCKDIPGFIPSLLGHLLEERQKIKTKMKETQDPIEKI
DV      VSPDTLNREGCREYDVAPEVGHKFCKDFPGFIPSLLKRLLDERQEIKRKMKASKDPIEKK

Tli     MLDYRQRAIKLLANSYYGYMGYPKARWYSKECAESVTAWGRHYIEMTIREIEEKFGFKVL
Tsp9N7  LLDYRQRAIKILANSFYGYYGYAKARWYCKECAESVTAWGREYIEMVIRELEEKFGFKVL
Tgo     LLDYRQRAIKILANSFYGYYGYAKARWYCKECAESVTAWGRQYIETTIREIEEKFGFKVL
Tko     LLDYRQRAIKILANSYYGYYGYARARWYCKECAESVTAWGREYITMTIKEIEEKYGFKVI
Pfu     LLDYRQKAIKLLANSFYGYYGYAKARWYCKECAESVTAWGRKYIELVWKELEEKFGFKVL
DV      MLDYRQRAIKILANSYYGYYGYAKARWYCKECAESVTAWGREYIEFVRKELEEKFGFKVL

Tli     YADTDGFYATIPGEKPELIKKKAKEFLNYINSKLPGLLELEYEGFYLRGFFVTKKRYAVI
Tsp9N7  YADTDGLHATIPGADAETVKKKAKEFLKYINPKLPGLLELEYEGFYVRGFFVTKKKYAVI
Tgo     YADTDGFFATIPGADAETVKKKAKEFLDYINAKLPGLLELEYEGFYKRGFFVTKKKYAVI
Tko     YSDTDGFFATIPGADAETVKKKAMEFLKYINAKLPGALELEYEGFYKRGFFVTKKKYAVI
Pfu     YIDTDGLYATIPGGESEEIKKKALEFVKYINSKLPGLLELEYEGFYKRGFFVTKKRYAVI
DV      YIDTDGLYATIPGAKPEEIKKKALEFVDYINAKLPGLLELEYEGFYVRGFFVTKKKYALI

Tli     DEEGRITTRGLEVVRRDWSEIAKETQAKVLEAILKEGSVEKAVEVVRDVVEKIAKYRVPL
Tsp9N7  DEEGKITTRGLEIVRRDWSEIAKETQARVLEAILKHGDVEEAVRIVKEVTEKLSKYEVPP
Tgo     DEEDKITTRGLEIVRRDWSEIAKETQARVLEAILKHGDVEEAVRIVKEVTEKLSKYEVPP
Tko     DEEGKITTRGLEIVRRDWSEIAKETQARVLEALLKDGDVEKAVRIVKEVTEKLSKYEVPP
Pfu     DEEGKVITRGLEIVRRDWSEIAKETQARVLETILKHGDVEEAVRIVKEVIQKLANYEIPP
DV      DEEGKIITRGLEIVRRDWSEIAKETQAKVLEAILKHGNVEEAVKIVKEVTEKLSKYEIPP

Tli     EKLVIHEQITRDLKDYKAIGPHVAIAKRLAARGIKVKPGTIISYIVLKGSGKISDRVILL
Tsp9N7  EKLVIHEQITRDLRDYKATGPHVAVAKRLAARGVKIRPGTVISYIVLKGSGRIGDRAIPA
Tgo     EKLVIYEQITRDLKDYKATGPHVAVAKRLAARGIKIRPGTVISYIVLKGSGRIGDRAIPF
Tko     EKLVIHEQITRDLKDYKATGPHVAVAKRLAARGVKIRPGTVISYIVLKGSGRIGDRAIPF
Pfu     EKLAIYEQITRPLHEYKAIGPHVAVAKKLAAKGVKIKPGMVIGYIVLRGDGPISNRAILA
DV      EKLVIYEQITRPLHEYKAIGPHVAVAKRLAARGVKVRPGMVIGYIVLRGDGPISKRAILA

Tli     TEYDPRKHKYDPDYYIENQVLPAVLRILEAFGYRKEDLRYQSSKQTGLDAWLKR------
Tsp9N7  DEFDPTKHRYDAEYYIENQVLPAVERILKAFGYRKEDLRYQKTKQVGLGAWLKVKGKK--
Tgo     DEFDPAKHKYDAEYYIENQVLPAVERILRAFGYRKEDLRYQKTRQVGLGAWLKPKT----
Tko     DEFDPTKHKYDAEYYIENQVLPAVERILRAFGYRKEDLRYQKTRQVGLSAWLKPKGT---
Pfu     EEYDPKKHKYDAEYYIENQVLPAVLRILEGFGYRKEDLRYQKTRQVGLTSWLNIKKS---
DV      EEFDLRKHKYDAEYYIENQVLPAVLRILEAFGYRKEDLRWQKTKQTGLTAWLNIKKK---

Tli     SEQ ID NO: 22
Tsp9N7  SEQ ID NO: 40
Tgo     SEQ ID NO: 30
Tko     SEQ ID NO: 34
Pfu     SEQ ID NO: 1
DV      SEQ ID NO: 16
```

*FIG. 1B*

```
Tli      TYLGGYVKEPEKGLWENIIYLDFRSLYPSIIVTHNVSPDTLEKEGCKNYDVAPIVGYRFC
Tsp9N7   GYAGGYVKEPERGLWDNIVYLDFRSLYPSIIITHNVSPDTLNREGCKEYDVAPEVGHKFC
Tgo      SYAGGYVKEPERGLWENIVYLDFRSLYPSIIITHNVSPDTLNREGCEEYDVAPQVGHKFC
Tko      SYEGGYVKEPERGLWENIVYLDFRSLYPSIIITHNVSPDTLNREGCKEYDVAPQVGHRFC
Pfu      SYTGGFVKEPEKGLWENIVYLDFRALYPSIIITHNVSPDTLNEGCKNYDIAPQVGHKFC
DV       SYAGGYVKEPEKGLWEGLVSLDFRSLYPSIIITHNVSPDTLNREGCREYDVAPEVGHKFC

Tli      KDFPGFIPSILGDLIAMRQDIKKKMKSTIDPIEKKMLDYRQRAIKLLANSYYGYMGYPKA
Tsp9N7   KDFPGFIPSLLGDLLEERQKIKRKMKATVDPLEKKLLDYRQRAIKILANSFYGYYGYAKA
Tgo      KDFPGFIPSLLGDLLEERQKVKKKMKATIDPIEKKLLDYRQRAIKILANSFYGYYGYAKA
Tko      KDFPGFIPSLLGDLLEERQKIKKKMKATIDPIERKLLDYRQRAIKILANSYYGYYGYARA
Pfu      KDIPGFIPSLLGHLLEERQKIKTKMKETQDPIEKILLDYRQKAIKLLANSFYGYYGYAKA
DV       KDFPGFIPSLLKRLLDERQEIKRKMKASKDPIEKKMLDYRQRAIKILANSYYGYYGYAKA

Tli      RWYSKECAESVTAWGRHYIEMTIREIEEKFGFKVLYADTDGFYATIPGEKPELIKKKAKE
Tsp9N7   RWYCKECAESVTAWGREYIEMVIRELEEKFGFKVLYADTDGLHATIPGADAETVKKKAKE
Tgo      RWYCKECAESVTAWGRQYIETTIREIEEKFGFKVLYADTDGFFATIPGADAETVKKKAKE
Tko      RWYCKECAESVTAWGREYITMTIKEIEEKYGFKVIYSDTDGFFATIPGADAETVKKKAME
Pfu      RWYCKECAESVTAWGRKYIELVWKELEEKFGFKVLYIDTDGLYATIPGGESEEIKKKALE
DV       RWYCKECAESVTAWGREYIEFVRKELEEKFGFKVLYIDTDGLYATIPGAKPEEIKKKALE

Tli      FLNYINSKLPGLLELEYEGFYLRGFFVTKKRYAVIDEEGRITTRGLEVVRRDWSEIAKET
Tsp9N7   FLKYINPKLPGLLELEYEGFYVRGFFVTKKKYAVIDEEGKITTRGLEIVRRDWSEIAKET
Tgo      FLDYINAKLPGLLELEYEGFYKRGFFVTKKKYAVIDEEDKITTRGLEIVRRDWSEIAKET
Tko      FLKYINAKLPGALELEYEGFYKRGFFVTKKKYAVIDEEGKITTRGLEIVRRDWSEIAKET
Pfu      FVKYINSKLPGLLELEYEGFYKRGFFVTKKRYAVIDEEGKVITRGLEIVRRDWSEIAKET
DV       FVDYINAKLPGLLELEYEGFYVRGFFVTKKKYALIDEEGKIITRGLEIVRRDWSEIAKET

Tli      QAKVLEAILKEGSVEKAVEVVRDVVEKIAKYRVPLEKLVIHEQITRDLKDYKAIGPHVAI
Tsp9N7   QARVLEAILKHGDVEEAVRIVKEVTEKLSKYEVPPEKLVIHEQITRDLRDYKATGPHVAV
Tgo      QARVLEAILKHGDVEEAVRIVKEVTEKLSKYEVPPEKLVIYEQITRDLKDYKATGPHVAV
Tko      QARVLEALLKDGDVEKAVRIVKEVTEKLSKYEVPPEKLVIHEQITRDLKDYKATGPHVAV
Pfu      QARVLETILKHGDVEEAVRIVKEVIQKLANYEIPPEKLAIYEQITRPLHEYKAIGPHVAV
DV       QAKVLEAILKHGNVEEAVKIVKEVTEKLSKYEIPPEKLVIYEQITRPLHEYKAIGPHVAV

Tli      AKRLAARGIKVKPGTIISYIVLKGSGKISDRVILLTEYDPRKHKYDPDYYIENQVLPAVL
Tsp9N7   AKRLAARGVKIRPGTVISYIVLKGSGRIGDRAIPADEFDPTKHRYDAEYYIENQVLPAVE
Tgo      AKRLAARGIKIRPGTVISYIVLKGSGRIGDRAIPFDEFDPAKHHYDAEYYIENQVLPAVE
Tko      AKRLAARGVKIRPGTVISYIVLKGSGRIGDRAIPFDEFDPTKHHYDAEYYIENQVLPAVE
Pfu      AKKLAAKGVKIKPGMVIGYIVLRGDGPISNRAILAEEYDPKKHKYDAEYYIENQVLPAVL
DV       AKRLAARGVKVRPGMVIGYIVLRGDGPISKRAILAEEFDLRKHKYDAEYYIENQVLPAVL

Tli      RILEAFGYRKEDLRYQSSKQTGL    SEQ ID NO: 24
Tsp9N7   RILKAFGYRKEDLRYQKTKQVGL    SEQ ID NO: 38
Tgo      RILRAFGYRKEDLRYQKTRQVGL    SEQ ID NO: 32
Tko      RILRAFGYRKEDLRYQKTRQVGL    SEQ ID NO: 36
Pfu      RILEGFGYRKEDLRYQKTRQVGL    SEQ ID NO: 4
DV       RILEAFGYRKEDLRWQKTKQTGL    SEQ ID NO: 18
```

*FIG. 2*

ANTIBODIES THAT BIND THERMOPHILIC DNA POLYMERASES

This application claims the benefit of priority to U.S. Provisional Application No. 62/279,426, filed Jan. 15, 2016, which is incorporated by reference herein in its entirety for any purpose.

The present application is filed with a Sequence Listing in electronic format. The Sequence Listing is provided as a file entitled "2016-12-30_01158-0003-00US_ST25.txt" created on Dec. 30, 2016, which is 257,434 bytes in size. The information in the electronic format of the sequence listing is incorporated herein by reference in its entirety.

This disclosure relates to the field of antibodies that bind thermophilic DNA polymerases, including methods, uses, and compositions comprising such antibodies.

Thermophilic DNA polymerases are commonly used in biotechnology and molecular biology applications, including nucleic acid synthesis techniques such as amplification (e.g., PCR), which involves cycles of alternating denaturation and primer annealing and extension. Thermophilic DNA polymerases are resistant to inactivation by high temperatures and so are compatible with thermal denaturation steps. DNA polymerases comprise a catalytic domain that extends a 3' terminus of a DNA strand in a template-dependent manner. DNA polymerases can also comprise an exonuclease domain, such as a 3' to 5' exonuclease domain. Such an exonuclease domain can reduce the frequency of misincorporation by removing mismatched nucleotides from the 3' end of a nascent DNA strand. Certain artificial DNA polymerases further comprise a sequence non-specific double-stranded DNA (dsDNA) binding domain. The presence of this domain can improve performance of the enzyme with respect to various parameters, including processivity, sensitivity, and yield.

Nucleic acid amplification can permit rapid detection of a target nucleic acid sequence and/or provide sufficient quantities of a sample for further analysis or manipulation, such as sequencing, cloning, restriction digestion, hybridization, ligation, mutagenesis, recombination, etc. Two key parameters of amplification are sensitivity and yield. Improving the sensitivity reduces the minimum amount of a target needed to produce a detectable product. Improving the yield increases the amount of product that results from a reaction, or reduces the amount of time and/or reagents necessary to obtain a given amount of product.

Hot start compositions are often used in nucleic acid synthesis (such as amplification) reactions to reduce non-specific nucleic acid synthesis at lower temperatures, improving specificity. In some embodiments, the present application provides antibodies that bind DNA polymerase and which may be used in hot start compositions. In some embodiments, hot start compositions are provided, comprising an antibody described herein bound to a DNA polymerase. In some such embodiments, the DNA polymerase is a thermophilic DNA polymerase.

In some embodiments, the present disclosure provides antibodies that bind to a DNA polymerase.

In some embodiments, a monoclonal antibody that binds a DNA polymerase is provided, wherein the antibody comprises: (a) a light chain comprising a CDR1 of SEQ ID NO: 57, a CDR2 of SEQ ID NO: 58, and a CDR3 of SEQ ID NO: 59, and a heavy chain comprising a CDR1 of SEQ ID NO: 60, a CDR2 of SEQ ID NO: 61, and a CDR3 of SEQ ID NO: 62; or (b) a light chain comprising a CDR1 of SEQ ID NO: 63, a CDR2 of SEQ ID NO: 64, and a CDR3 of SEQ ID NO:65 and a heavy chain comprising a CDR1 of SEQ ID NO: 66, a CDR2 of SEQ ID NO: 67, and a CDR3 of SEQ ID NO: 68. In some embodiments, the antibody comprises: (a) a light chain variable region comprising the sequence of SEQ ID NO: 53 and a heavy chain variable region comprising the sequence of SEQ ID NO: 54; or (b) a light chain variable region comprising the sequence of SEQ ID NO: 55 and a heavy chain variable region comprising the sequence of SEQ ID NO: 56.

In some embodiments, the antibody is an antibody fragment. In some embodiments, the antibody fragment is selected from a Fab fragment, a Fab' fragment, a (Fab')$_2$ fragment, an Fv fragment, and an scFv fragment. In some embodiments, the antibody is an IgG antibody. In some embodiments, the antibody is an IgG1, IgG2, IgG3, or IgG4 antibody.

In some embodiments, compositions are provided, comprising an antibody described herein and a protein comprising a DNA polymerase catalytic domain. In some embodiments, the DNA polymerase catalytic domain is a thermophilic DNA polymerase catalytic domain. In some embodiments, the thermophilic DNA polymerase catalytic domain is a family B DNA polymerase catalytic domain. In some embodiments, the thermophilic DNA polymerase catalytic domain comprises an amino acid sequence having at least 90%, 95%, 98%, 99%, or 100% identity to a sequence selected from SEQ ID NOs: 4 to 6, 10 to 12, 18, 19, 22, 23, 26, 27, 32, 33, and 36 to 38. In some embodiments, the protein further comprises a 3' to 5' exonuclease domain. In some embodiments, the 3' to 5' exonuclease domain is N-terminal to the DNA polymerase catalytic domain. In some embodiments, the 3' to 5' exonuclease domain is a DEDDy archaeal exonuclease domain. In some embodiments, the 3' to 5' exonuclease domain comprises an amino acid sequence having at least 90%, 95%, 98%, 99%, or 100% identity to SEQ ID NO: 52. In some embodiments, the 3' to 5' exonuclease domain comprises an amino acid sequence having at least 90%, 95%, 98%, 99%, or 100% identity to the 3' to 5' exonuclease domain of a sequence selected from SEQ ID NOs: 1 to 3, 16, 17, 24, 25, 28, 29, 30, 31, 34, 35, 40, 41, and 69 to 71. In some embodiments, the protein comprises an amino acid sequence selected from SEQ ID NOs: 1 to 3, 16, 17, 24, 25, 28, 29, 30, 31, 34, 35, 40, 41, and 69 to 71. In some embodiments, the protein further comprises a sequence non-specific DNA-binding domain. In some embodiments, the sequence non-specific DNA-binding domain comprises an amino acid sequence having at least 90%, 95%, 98%, 99%, or 100% identity to a sequence selected from SEQ ID NOs: 42 to 51. In some embodiments, the sequence non-specific DNA-binding domain is C-terminal to the DNA polymerase catalytic domain. In some embodiments, the sequence non-specific DNA-binding domain is a 7 kD DNA-binding domain. In some embodiments, the sequence non-specific DNA-binding domain is an Sso7d, Sac7d, or Sac7e domain. In some embodiments, the protein comprises an amino acid sequence having at least 90%, 95%, 98%, 99%, or 100% identity to a sequence selected from SEQ ID NOs: 7 to 9, 13 to 15, 20, and 21. In some embodiments, the thermophilic DNA polymerase comprises an amino acid sequence comprising (i) at least one difference at a position corresponding to position 15, 72, 93, 141, 143, 247, 265, 337, 385, 387, 388, 399, 400, 405, 407, 410, 485, 542, 546, 593, or 595 of SEQ ID NO: 1 or (ii) at least one missing residue corresponding to position 92, 93, 94, or 381 of SEQ ID NO: 1. In some embodiments, the at least one mismatch or missing residue comprises at least one of:

(i) a missing residue corresponding to position 92 or 94 of SEQ ID NO: 1;
(ii) a Q or R at the position corresponding to position 93 of SEQ ID NO: 1;
(iii) an A at the position corresponding to position 141 of SEQ ID NO: 1;
(iv) an A at the position corresponding to position 143 of SEQ ID NO: 1;
(v) an I at the position corresponding to position 337 of SEQ ID NO: 1;
(vi) a Q, S, N, L, or H at the position corresponding to position 385 of SEQ ID NO: 1;
(vii) a P or S at the position corresponding to position 387 of SEQ ID NO: 1;
(viii) a P at the position corresponding to position 388 of SEQ ID NO: 1;
(ix) a D at the position corresponding to position 399 of SEQ ID NO: 1;
(x) a G or D at the position corresponding to position 400 of SEQ ID NO: 1;
(xi) an E at the position corresponding to position 405 of SEQ ID NO: 1;
(xii) an I at the position corresponding to position 407 of SEQ ID NO: 1;
(xiii) an L or F at the position corresponding to position 410 of SEQ ID NO: 1;
(xiv) a T at the position corresponding to position 485 of SEQ ID NO: 1;
(xv) a P at the position corresponding to position 542 of SEQ ID NO: 1;
(xvi) an H at the position corresponding to position 546 of SEQ ID NO: 1;
(xvii) a T at the position corresponding to position 593 of SEQ ID NO: 1; or
(xviii) an S at the position corresponding to position 595 of SEQ ID NO: 1.

In some embodiments, the composition further comprises at least one additional hot start inhibitor. In some embodiments, an additional hot start inhibitor is selected from an antibody, an Affibody®, a chemical modification, and an oligonucleotide, such as an aptamer. In some embodiments, an additional hot start inhibitor is an oligonucleotide. In some embodiments, an additional hot start inhibitor is an Affibody®. In some embodiments, an additional hot start inhibitor is chemical modification. In some embodiments, an additional hot start inhibitor is a second antibody.

In some embodiments, the composition is a storage composition. In some embodiments, the composition comprises at least one protein stabilizer. In some embodiments, the protein stabilizer is selected from BSA, inactive polymerase, and apotransferrin. In some embodiments, the composition comprises a UTPase. In some embodiments, the composition comprises at least one buffering agent. In some embodiments, the buffering agent is selected from acetate buffer, sulfate buffer, phosphate buffer, MOPS, HEPES and Tris-(hydroxymethyl)aminomethane (TRIS). In some embodiments, the composition comprises at least one monovalent cationic salt. In some embodiments, the monovalent cationic salt is selected from KCl and NaCl. In some embodiments, the composition comprises at least one stabilizer. In some embodiments, the stabilizer is selected from glycerol, trehalose, lactose, maltose, galactose, glucose, sucrose, dimethyl sulfoxide (DMSO), polyethylene glycol, and sorbitol. In some embodiments, the composition comprises at least one reducing agent. In some embodiments, the reducing agent is dithiothreitol (DTT). In some embodiments, the composition comprises at least one divalent cation chelating agent. In some embodiments, the divalent cation chelating agent is EDTA. In some embodiments, the composition comprises at least one detergent. In some embodiments the detergent is anionic. In some embodiments, the detergent is cationic. In some embodiments, the detergent is non-ionic. In some embodiments, the detergent is zwitterionic. In some embodiments, the composition comprises a detergent selected from Hecameg (6-O—(N-Heptylcarbamoyl)-methyl-α-D-glucopyranoside), Triton X-200, Brij-58, CHAPS, n-Dodecyl-b-D-maltoside, NP-40, sodium dodecyl sulphate (SDS), TRITON® X-15, TRITON® X-35, TRITON® X-45, TRITON® X-100, TRITON® X-102, TRITON® X-114, TRITON® X-165, TRITON® X-305, TRITON® X-405, TRITON® X-705, Tween® 20 and/or ZWITTERGENT®.

In some embodiments, the composition is an aqueous solution. In some embodiments, the composition is a lyophilized composition.

In some embodiments, methods of in vitro nucleic acid synthesis are provided, comprising contacting at least one primer and at least one template with a composition comprising an antibody described herein and a DNA polymerase in the presence of at least one dNTP, and heating the composition to at least 60° C., at least 65° C., at least 70° C., at least 75° C., at least 80° C., or at least 85° C. In some embodiments, the method further comprises amplification of the template. In some embodiments, the amplification comprises polymerase chain reaction (PCR).

In some embodiments, nucleic acids comprising a sequence encoding a heavy chain of an antibody described herein are provided. In some embodiments, nucleic acids comprising a sequence encoding a light chain of an antibody described herein are provided. In some embodiments, nucleic acids comprising a sequence encoding a heavy chain and a light chain of an antibody described herein are provided. In some embodiments, an expression vector comprising a nucleic acid described herein is provided. In some embodiments, an isolated host cell comprising at least one nucleic acid described herein or an expression vector described herein is provided. In some embodiments, methods of producing an antibody described herein are provided, comprising culturing a host cell described herein under conditions suitable for expressing the antibody. In some embodiments, the method further comprises isolating the antibody.

In some embodiments, a kit comprising an antibody described herein is provided. In some embodiments, the kit comprises a composition comprising an antibody described herein and a DNA polymerase. In some embodiments, the kit further comprises at least one additional reagent for nucleic acid synthesis. In some embodiments, the at least one additional reagent for nucleic acid synthesis is selected from buffers, dNTPs, stabilizers, detergents, and dyes. In some embodiments, the kit further comprises a composition comprising at least one buffering agent, at least one monovalent cationic salt, at least one divalent cationic salt, at least one detergent and at least one dNTP.

BRIEF DESCRIPTION OF THE DRAWINGS

FIGS. 1A-B show a multiple amino acid sequence alignment of *Thermococcus litoralis* ("Tli"; SEQ ID NO: 22), ("Tsp9N7"; SEQ ID NO: 40), *Thermococcus gorgonarius* ("Tgo"; SEQ ID NO: 30), *Thermococcus kodakarensis* ("Tko"; SEQ ID NO: 34), *Pyrococcus furiosus* ("Pfu"; SEQ ID NO: 1), and Deep Vent ("DP"; SEQ ID NO: 16) polymerases.

FIG. 2 shows a multiple amino acid sequence alignment of the catalytic domains of *Thermococcus litoralis* ("Tli"; SEQ ID NO: 24), ("Tsp9N7"; SEQ ID NO: 38), *Thermococcus gorgonarius* ("Tgo"; SEQ ID NO: 32), *Thermococcus kodakarensis* ("Tko"; SEQ ID NO: 36), *Pyrococcus furiosus* ("Pfu"; SEQ ID NO: 4), and Deep Vent ("DP"; SEQ ID NO: 18) polymerases.

DETAILED DESCRIPTION

Figure 3:
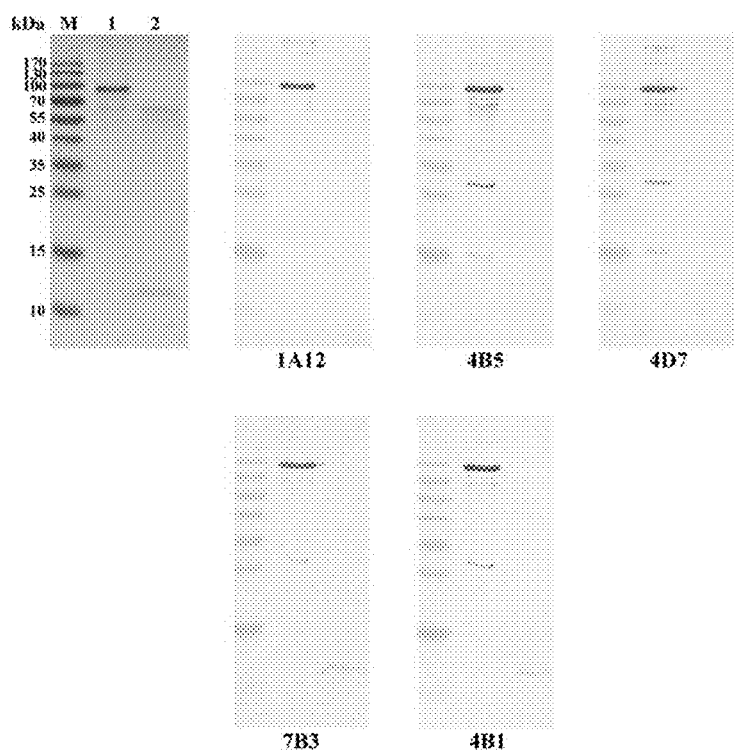
FIG. 3 shows Western blotting of recombinant Sso7d and *Pyrococcus* DNA polymerase with a sequence non-specific DNA binding domain (*Pyrococcus* DNA polymerase-DBD, SEQ ID NO: 13) immunostained with the indicated neutralizing monoclonal antibodies. The upper left picture shows the Coommassie-stained SDS-PAGE gel. On each gel, lane 1 is a pre-stained protein molecular weight marker, lane 2 is *Pyrococcus* DNA polymerase-DBD (SEQ ID NO: 13), and lane 3 is Sso7D.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be nonlimiting, such that recitation of items in a list is not to the exclusion of other like items that can be substituted or added to the listed items.

The term "nucleic acid synthesis" refers to template-directed synthesis of a nucleic acid strand using a polymerase enzyme. Nucleic acid synthesis includes all such template-directed nucleic acid synthesis by a polymerase, including, but not limited to, amplification, PCR, end point PCR (ePCR), real time or quantitative (qPCR), one-step RT-PCR, sequencing, etc.

As used herein the terms "amplify", "amplifying", "amplification" and other related terms include producing multiple copies of an original biomolecule, such as a nucleic acid. In some embodiments, nucleic acid amplification produces multiple copies of an original nucleic acid and/or its complement (e.g., target nucleic acid, also referred to as a target polynucleotide), where the copies comprise at least a portion of the template sequence and/or its complement. Such copies may be single-stranded or double-stranded.

A "template" or "template nucleic acid" or "template polynucleotide" refers to a polynucleotide that comprises the polynucleotide sequence to be amplified. In some embodiments, the polynucleotide sequence to be amplified is flanked by primer hybridization sites, such as a hybridization site for a 5' primer (or the complement thereof) and a hybridization site for a 3' primer (or the complement thereof). A template may comprise RNA and/or DNA, and may be from a natural source, or be synthetic. Nonlimiting exemplary templates include genomic DNA, viral DNA, mitochondrial DNA, viral RNA, mRNA, tRNA, microRNA, plasmids, vectors, cosmids, artificial chromosomes, etc. Any polynucleotide that may be copied or amplified by a polymerase enzyme is considered a template.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity, and/or can have a stabilizing effect on the structure of the protein.

Residues "correspond" to each other where they occur at equivalent positions in aligned amino acid sequences, such as family B thermophilic polymerase sequences and/or a domain thereof, such as a catalytic or exonuclease domain. Corresponding positions can be identified as positions that align with one another. Related or variant polypeptides are aligned by any method in the art. Such methods typically maximize matches, and include methods such as using manual alignments and by using any of the numerous alignment programs available (for example, BLASTP) and others known in the art. By aligning the sequences of polypeptides, one of skill in the art can identify corresponding residues, using conserved and identical amino acid residues as guides. In some embodiments, an amino acid of a polypeptide is considered to correspond to an amino acid in a disclosed sequence when the amino acid of the polypeptide is aligned with the amino acid in the disclosed sequence upon alignment of the polypeptide with the disclosed sequence to maximize identity and homology (e.g., where conserved amino acids are aligned) using a standard alignment algorithm, such as the BLASTP algorithm with default scoring parameters (such as, for example, BLOSUM62 Matrix, Gap existence penalty 11, Gap extension penalty 1, and with default general parameters).

"Identity" is measured by a score determined by comparing the amino acid sequences of the two polypeptides using the Bestfit program. Bestfit uses the local homology algorithm of Smith and Waterman, *Advances in Applied Mathematics* 2:482-489 (1981) to find the best segment of similarity between two sequences. When using Bestfit to determine whether a test amino acid sequence is, for instance, 95% identical to a reference sequence according to the present disclosure, the parameters are set so that the percentage of identity is calculated over the full length of the test amino acid sequence, such that 95% of the amino acids in the test amino acid sequence align with identical amino acids on the reference sequence.

"Sequence non-specific DNA binding domain" or "DNA binding domain" refers to a protein domain that binds to DNA without significant sequence preference. In some embodiments, a DNA binding domain binds to double-stranded DNA. Nonlimiting exemplary DNA binding domains include Sso7d from *Sulfolobus solfataricus*, Sac7d, Sac7a, Sac7b, and Sac7e from *S. acidocaldarius*, and Ssh7a and Ssh7b from *Sulfolobus shibatae*, Pae3192, Pae0384, and Ape3192, HMf family archaeal histone domains, and archaeal PCNA homolog.

With reference to two polypeptides or two polypeptide domains, the term "fused" means that the two polypeptides or polypeptide domains are contained in a single contiguous polypeptide sequence.

"Heterologous", when used with reference to portions of a protein, indicates that the protein comprises two or more domains that are not found in the same relationship to each other in nature. In some embodiments, such a protein, e.g., a fusion protein, contains two or more domains from unrelated proteins arranged to make a new functional protein.

"Error-correcting activity" of a polymerase or polymerase domain refers to the 3' to 5' exonuclease proofreading activity of a polymerase whereby nucleotides that do not form Watson-Crick base pairs with the template are removed from the 3' end of an oligonucleotide, i.e., a strand being synthesized from a template, in a sequential manner. Examples of polymerases that have error-correcting activity include polymerases from *Pyrococcus furiosus, Thermococcus litoralis*, and *Thermotoga maritima* with wild-type exonuclease domains, and certain others discussed herein.

"Sensitivity" as used herein, refers to the ability of a polymerase to amplify a target nucleic acid that is present at low copy number. In some embodiments, low copy number refers to a target nucleic acid that is present at fewer than 10,000 or fewer than 1,000 or fewer than 100 or fewer than 10 copies in the composition comprising the target nucleic acid and the polymerase.

"Specificity" as used herein, refers to the ability of a polymerase to amplify a target nucleic acid while producing fewer non-specific amplification byproducts, such as those resulting from primer-dimers.

As used herein the terms "hybridize", "hybridizing", "hybridization" and other related terms include hydrogen bonding between two different nucleic acids, or between two different regions of a nucleic acid, to form a duplex nucleic acid. Hybridization can comprise Watson-Crick or Hoogstein binding to form a duplex nucleic acid. The two different nucleic acids, or the two different regions of a nucleic acid, may be complementary, or partially complementary. The complementary base pairing can be the standard A-T or C-G base pairing, or can be other forms of base-pairing interactions. Duplex nucleic acids can include mismatched base-paired nucleotides. Complementary nucleic acid strands need not hybridize with each other across their entire length.

The term "antibody" is used in the broadest sense and encompasses various antibody structures, including but not limited to monoclonal antibodies, polyclonal antibodies, multispecific antibodies (such as bispecific antibodies), and antibody fragments so long as they exhibit the desired antigen-binding activity.

The term antibody includes, but is not limited to, fragments that are capable of binding to an antigen, such as Fv, single-chain Fv (scFv), Fab, Fab', di-scFv, sdAb (single domain antibody) and (Fab')$_2$ (including a chemically linked F(ab')$_2$). Papain digestion of antibodies produces two identical antigen-binding fragments, called "Fab" fragments, each with a single antigen-binding site, and a residual "Fc" fragment. Pepsin treatment yields a F(ab')$_2$ fragment that has two antigen-binding sites. The term antibody also includes, but is not limited to, chimeric antibodies, humanized antibodies, and antibodies of various species such as mouse, goat, horse, sheep, chicken, etc. Furthermore, for all antibody constructs provided herein, variants having the sequences from other organisms are also contemplated, such as CDR-grafted antibodies or chimeric antibodies. Antibody fragments also include either orientation of single chain scFvs, tandem di-scFv, diabodies, tandem tri-sdcFv, minibodies, etc. Antibody fragments also include nanobodies (sdAb, an antibody having a single, monomeric domain, such as a pair of variable domains of heavy chains, without a light chain). An antibody fragment can be referred to as being a specific species in some embodiments (for example, human scFv or a mouse scFv). This denotes the sequences of at least part of the non-CDR regions, rather than the source of the construct.

The term "monoclonal antibody" refers to an antibody of a substantially homogeneous population of antibodies, that is, the individual antibodies comprising the population are identical except for possible naturally-occurring mutations that may be present in minor amounts. The term "monoclonal" indicates the character of the antibody as being obtained from a substantially homogeneous population of antibodies, and is not to be construed as requiring production of the antibody by any particular method. For example, the monoclonal antibodies may be expressed by hybridomas, or may be made by recombinant DNA methods and expressed from another cell type. Monoclonal antibodies may also be isolated from phage libraries.

The term "CDR" denotes a complementarity determining region as defined by at least one method known in the art. In some embodiments, CDRs can be defined in accordance with any of the Chothia numbering schemes, the Kabat numbering scheme, a combination of Kabat and Chothia, the AbM definition, and/or the contact definition. Exemplary Kabat-defined CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991)).

The term "heavy chain variable region" as used herein refers to a region comprising at least three heavy chain CDRs. In some embodiments, the heavy chain variable region includes the three CDRs and at least FR2 and FR3. In some embodiments, the heavy chain variable region includes at least heavy chain CDR1, framework (FR) 2, CDR2, FR3, and CDR3. In some embodiments, a heavy chain variable region also comprises at least a portion of a FR1 and/or at least a portion of a FR4.

The term "heavy chain constant region" as used herein refers to a region comprising at least three heavy chain constant domains, CH1, CH2, and CH3. Non-function-altering deletions and alterations within the domains are encompassed within the scope of the term "heavy chain constant region," unless designated otherwise. Nonlimiting exemplary heavy chain constant regions include γ, δ, and α, and variants thereof that do not alter the functions of the antibody needed for its intended use. Nonlimiting exemplary heavy chain constant regions also include ε and μ, and variants thereof that do not alter the functions of the antibody needed for its intended use. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a γ1 constant region), IgG2 (comprising a γ2 constant region), IgG3 (comprising a γ3 constant region), and IgG4 (comprising a γ4 constant region) antibodies; IgA antibodies include, but are not limited to, IgA1 (comprising an α1 constant region) and IgA2 (comprising an α2 constant region) antibodies; and IgM antibodies include, but are not limited to, IgM1 and IgM2.

The term "heavy chain" as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "light chain variable region" as used herein refers to a region comprising at least three light chain CDRs. In some embodiments, the light chain variable region includes the three CDRs and at least FR2 and FR3. In some embodiments, the light chain variable region includes at least light chain CDR1, framework (FR) 2, CDR2, FR3, and CDR3. For example, a light chain variable region may comprise light chain CDR1, framework (FR) 2, CDR2, FR3, and CDR3. In some embodiments, a light chain variable region also comprises at least a portion of a FR1 and/or at least a portion of a FR4.

The term "light chain constant region" as used herein refers to a region comprising a light chain constant domain, CL. Nonlimiting exemplary light chain constant regions include λ and κ, and variants thereof that do not alter the functions of the antibody needed for its intended use.

The term "light chain" as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

In some embodiments, conditions that are suitable for nucleic acid hybridization and/or nucleic acid synthesis include parameters such as salts, buffers, pH, temperature, % GC content of the polynucleotide and primers, and/or time. For example, conditions suitable for hybridizing nucleic acids (e.g., polynucleotides and primers) can include hybridization solutions having sodium salts, such as NaCl, sodium citrate and/or sodium phosphate. In some embodiments, a hybridization solution can be a stringent hybridization solution which can include any combination of formamide (e.g., about 50%), 5×SSC (e.g., about 0.75 M NaCl and about 0.075 M sodium citrate), sodium phosphate (e.g., about 50 mM at about pH 6.8), sodium pyrophosphate (e.g., about 0.1%), 5×Denhardt's solution, SDS (e.g., about 0.1%), and/or dextran sulfate (e.g., about 10%). In some embodiments, hybridization and/or nucleic acid synthesis can be conducted at a temperature range of about 45-55° C., or about 55-65° C., or about 65-75° C. In some embodiments, hybridization or nucleic acid synthesis conditions can be conducted at a pH range of about 5-10, or about pH 6-9, or about pH 6.5-8, or about pH 6.5-7.

Thermal melting temperature ($T_m$) for nucleic acids can be a temperature at which half of the nucleic acid strands are double-stranded and half are single-stranded under a defined condition. In some embodiments, a defined condition can include ionic strength and pH in an aqueous reaction condition. A defined condition can be modulated by altering the concentration of salts (e.g., sodium), temperature, pH, buffers, and/or formamide. Typically, the calculated thermal melting temperature can be at about 5-30° C. below the $T_m$, or about 5-25° C. below the $T_m$, or about 5-20° C. below the $T_m$, or about 5-15° C. below the $T_m$, or about 5-10° C. below the $T_m$. Methods for calculating a $T_m$ are well known and can be found in Sambrook (1989 in "Molecular Cloning: A Laboratory Manual", 2$^{nd}$ edition, volumes 1-3; Wetmur 1966, J. Mol. Biol., 31:349-370; Wetmur 1991 Critical Reviews in Biochemistry and Molecular Biology, 26:227-259). Other sources for calculating a $T_m$ for hybridizing or denaturing nucleic acids include OligoAnalyze (from Integrated DNA Technologies) and Primer3 (distributed by the Whitehead Institute for Biomedical Research).

Antibodies that Bind DNA Polymerase and Methods of Making Same

Provided herein are antibodies that bind to DNA polymerase and their use in hot start compositions. In some embodiments, the DNA polymerase is a thermophilic DNA polymerase. Such thermophilic DNA polymerases may comprise, in some embodiments, a Family B polymerase catalytic domain, or a variant thereof. Many types of family B polymerases are described, e.g., in Rothwell and Watsman, *Advances in Protein Chemistry* 71:401-440 (2005). Examples of thermophilic Family B polymerases include those of the *Pyrococcus* and *Thermococcus* genera, such as the Deep Vent polymerase and Family B polymerases of *P. furiosus, P. calidifontis, P. aerophilum, T. kodakarensis, T. gorgonarius*, and *Thermococcus* sp. 9° N-7. Exemplary wild-type amino acid sequences for such thermophilic family B polymerases can be obtained from public databases such as NCBI GenBank or UniProt. Wild-type sequences include naturally-occurring variants of the amino acid sequences for such thermophilic family B polymerases. Note that in some cases, the sequences are annotated as containing inteins; the inteins are not present in the mature enzyme.

In some embodiments, an antibody that binds a DNA polymerase is provided, wherein the antibody comprises at least one, at least two, at least three, at least four, at least five, or all six CDRs, as follows: light chain CDR1 (LC-CDR1) comprising the amino acid sequence of SEQ ID NO: 57, LC-CDR2 comprising the amino acid sequence of SEQ ID NO: 58, LC-CDR3 comprising the amino acid sequence of SEQ ID NO: 59, heavy chain CDR1 (HC-CDR1) comprising the amino acid sequence of SEQ ID NO: 60, HC-CDR2 comprising the amino acid sequence of SEQ ID NO: 61, and HC-CDR3 comprising the amino acid sequence of SEQ ID NO: 62. In some embodiments, an antibody that binds a DNA polymerase is provided, wherein the antibody comprises light chain CDR1 (LC-CDR1) comprising the amino acid sequence of SEQ ID NO: 57, LC-CDR2 comprising the amino acid sequence of SEQ ID NO: 58, LC-CDR3 comprising the amino acid sequence of SEQ ID NO: 59, heavy chain CDR1 (HC-CDR1) comprising the amino acid sequence of SEQ ID NO: 60, HC-CDR2 comprising the amino acid sequence of SEQ ID NO: 61, and HC-CDR3 comprising the amino acid sequence of SEQ ID NO: 62.

In some embodiments, an antibody that binds a DNA polymerase is provided, wherein the antibody comprises at least one, at least two, at least three, at least four, at least five, or all six CDRs, as follows: light chain CDR1 (LC-CDR1) comprising the amino acid sequence of SEQ ID NO: 63, LC-CDR2 comprising the amino acid sequence of SEQ ID NO: 64, LC-CDR3 comprising the amino acid sequence of SEQ ID NO: 65, heavy chain CDR1 (HC-CDR1) comprising the amino acid sequence of SEQ ID NO: 66, HC-CDR2 comprising the amino acid sequence of SEQ ID NO: 67, and HC-CDR3 comprising the amino acid sequence of SEQ ID NO: 68. In some embodiments, an antibody that binds a DNA polymerase is provided, wherein the antibody comprises light chain CDR1 (LC-CDR1) comprising the amino acid sequence of SEQ ID NO: 63, LC-CDR2 comprising the amino acid sequence of SEQ ID NO: 64, LC-CDR3 comprising the amino acid sequence of SEQ ID NO: 65, heavy chain CDR1 (HC-CDR1) comprising the amino acid sequence of SEQ ID NO: 66, HC-CDR2 comprising the amino acid sequence of SEQ ID NO: 67, and HC-CDR3 comprising the amino acid sequence of SEQ ID NO: 68.

In some embodiments, an antibody that binds a DNA polymerase is provided, wherein the antibody comprises a light chain variable region comprising the amino acid sequence of SEQ ID NO: 53. In some embodiments, an antibody that binds a DNA polymerase is provided, wherein the antibody comprises a heavy chain variable region comprising the amino acid sequence of SEQ ID NO: 54. In some embodiments, an antibody that binds a DNA polymerase is provided, wherein the antibody comprises a light chain variable region comprising the amino acid sequence of SEQ ID NO: 53 and a heavy chain variable region comprising the amino acid sequence of SEQ ID NO: 54.

In some embodiments, an antibody that binds a DNA polymerase is provided, wherein the antibody comprises a light chain variable region comprising the amino acid sequence of SEQ ID NO: 55. In some embodiments, an antibody that binds a DNA polymerase is provided, wherein the antibody comprises a heavy chain variable region comprising the amino acid sequence of SEQ ID NO: 56. In some embodiments, an antibody that binds a DNA polymerase is provided, wherein the antibody comprises a light chain variable region comprising the amino acid sequence of SEQ ID NO: 55 and a heavy chain variable region comprising the amino acid sequence of SEQ ID NO: 56.

In some embodiments, the antibody is a monoclonal antibody. In some embodiments, the antibody is an IgG antibody. In some embodiments, the antibody is an IgG1, IgG2, IgG3, or IgG4 antibody. In some embodiments, the antibody is an IgGA, IgGD, or IgGM antibody.

In some embodiments, the antibody is an antibody fragment. Nonlimiting exemplary antibody fragments include Fab fragments, Fab' fragments, (Fab')$_2$ fragments, Fv fragments, and scFv fragments.

Methods for producing and screening for antibodies that are suitable for use in hot start compositions with the polymerases described herein are known in the art. In some embodiments, a hot start antibody inhibits the nucleic acid synthesis activity of the thermophilic polymerase described herein. In some embodiments, a hot start antibody inhibits exonuclease activity of the thermophilic polymerase. In some embodiments, a hot start antibody inhibits both the nucleic acid synthesis activity and the exonuclease activity of the thermophilic polymerase.

In some embodiments, hot-start antibodies increase the specificity of nucleic acid synthesis reactions, because they inactivate the polymerase at room temperature, thus avoiding extension of nonspecifically hybridized primers. The functional activity of the polymerase is restored by disassociating the antibody from the polymerase, for example, by incubating the composition at a higher temperature. In some embodiment, the "higher temperature" is from about 65° C. to about 99° C., from about 70° C. to about 99° C., from about 75° C. to about 99° C., or from about 80° C. to about 99° C., or from about 85° C. to about 99° C., or from about 90° C. to about 99° C., for a time period of at least 15 seconds, or at least 30 seconds, or at least 1 minute, or at least 90 seconds, or at least 2 minutes; to about 3 minutes, or about 4 minutes, or about 5 minutes, or about 7 minutes, or about 10 minutes, or more. In some embodiments, the higher temperature is at least 60° C., at least 65° C., at least 70° C., at least 75° C., at least 80° C., or at least 85° C. In some embodiments, the temperature and duration of incubation to disassociate the antibody and activate the polymerase may be determined for the particular polymerase and antibody to be employed. One skilled in the art can determine the appropriate temperature and duration of incubation.

Methods for screening for antibodies of use in the present invention include methods known in the art, such as affinity-based ELISA assays, as well as functional assays for polymerase and/or exonuclease inhibition. For such functional assays, the amount of DNA produced or digested per unit of time can be correlated to the activity of the polymerase or exonuclease used, thus providing an estimate of the amount of inhibition a particular antibody can exert on either or both the polymerase and exonuclease activity of the polymerase.

Antibodies may be produced using any method known in the art. As a nonlimiting example, an antibody to a particular antigen (such as a polymerase described herein) may be produced by immunizing an animal (such as a mouse, rat, rabbit, goat, sheep, horse, etc.) with the antigen and isolating antibodies from the serum of the animal and/or immortalizing primary B cells from the animal to produce hybridomas that express the antibodies. Phage display technology may also be used to produce antibodies that bind to the polymerases described herein. Phage display libraries are commercially available and methods of selecting antibodies from such libraries are known in the art. See, e.g., Vaughan et al., 1996, Nature Biotechnology, 14:309-314; Sheets et al., 1998, Proc. Natl. Acad. Sci. (USA) 95:6157-6162; Hoogenboom and Winter, 1991, J. Mol. Biol., 227:381; Marks et al., 1991, J. Mol. Biol., 222:581.

Hot Start Compositions

In some embodiments, a composition is provided comprising an antibody provided herein and a DNA polymerase. In some embodiments, the composition comprises an antibody provided herein and a thermophilic DNA polymerase. In some embodiments, the composition comprising the antibody and DNA polymerase is a hot start composition. For discussion of hot-start enzymes and/or compositions, see, e.g., U.S. Pat. Nos. 5,338,671; 7,074,556; US Publication 2015/0044683; US Publication 2014/0099644. As used herein, the term "hot start" generally refers to a means of limiting the availability of an essential reaction component (e.g., a polymerase) when the reaction mixture is maintained at a first temperature (typically a lower temperature) until a second temperature (typically a higher temperature) is reached which allows the essential component to participate in the reaction. Hot start reactions typically involve incubation at a first (e.g., lower) temperature and subsequent elevation to a second (e.g., higher) temperature which allows the desired reaction to take place. Activation of the hot start reaction is preferably achieved by an incubation at a temperature which is equal to or higher than the primer hybridization (annealing) temperature used in the amplification reaction to ensure primer binding specificity. The length of incubation required to recover enzyme activity depends on the temperature and pH of the reaction mixture and on the stability of the enzyme. A wide range of incubation conditions are usable; optimal conditions may be determined empirically for each reaction.

As used herein, the term "dual hot start reaction mixture" refers to the combination of reagents or reagent solutions which are used to block nucleic acid polymerase extension at low temperatures (e.g., ambient temperature) until the hot start conditions of the initial denaturation temperature in an amplification reaction (e.g., PCR) are reached. At the elevated amplification temperature, the nucleic acid polymerase is no longer inhibited and allows for primer extension. As used herein, the dual hot start reaction mixture is meant to include a reaction mixture that comprises at least two different mechanisms for hot start. Accordingly, "dual hot start reaction mixtures" may include more than two hot start mechanisms (e.g., "triple hot start reaction mixture", "quadruple hot start reaction mixture", "quintuple hot start reaction mixture", and so on).

Nonlimiting exemplary hot start mechanisms include, but are not limited to, antibodies or combinations of antibodies that block nucleic acid polymerase activity at lower temperatures and which dissociate from the polymerase at elevated temperatures (see, e.g., Eastlund et al., *LifeSci. Quarterly* 2:2 (2001), Mizuguchi et al., *J. Biochem.* (Tokyo) 126:762 (1999)); affibodies (small synthetic protein molecules that have high binding affinity for a target protein) or combinations of affibodies, sometimes referred to as antibody mimetics; oligonucleotides that block nucleic acid polymerase activity at lower temperatures and which dissociate from the polymerase at elevated temperatures (see, e.g., Dang et al., *J. Mol. Biol.* 264:268 (1996)); reversibly chemical modification of the nucleic acid polymerase such that the nucleic acid polymerase activity is blocked at lower temperatures and the modifications reverse or dissociate at elevated temperatures (see, e.g., U.S. Pat. No. 5,773,258 and Moretti et al., *Biotechniques* 25:716 (1998)); amino acid mutations of the nucleic acid polymerase that provide reduced activity at lower temperatures (see, e.g., Kermekchiev et al., *Nucl. Acids Res.* 31:6139 (2003)); nucleic acid polymerase fusion proteins including hyperstable DNA binding domains and topoisomerases (see, e.g., Pavlov et al., *Proc. Natl. Acad. Sci. USA* 99:13510 (2002)); ligands that inhibit the nucleic acid polymerase in a temperature-dependent manner (for example, HotMaster™ Taq DNA polymerase from Eppendorf (Hauppauge, N.Y.) and 5 PRIME (Gaithersburg, Md.)); single-stranded binding proteins that sequester primers at low temperatures (see, e.g., U.S. Patent Application Publication No. 2008/0138878); thermostable pyrophosphatase which hydrolyzes inorganic pyrophosphate at elevated temperatures (see, e.g., U.S. Patent Application Publication No. 2006/0057617); thermolabile blockers, such as a polymerase blocking protein (see, e.g., U.S. Patent Application Publication No. 2007/0009922); primer competitor sequences (see, e.g., Puskas et al., *Genome Res.* 5:309 (1995) and Vestheim et al., *Front. Zool.* 5:12 (2008)); modified primer constructs (see, e.g., Ailenberg et al., *Biotechniques* 29:22 (2000) and Kaboev et al., *Nucl. Acids Res.* 28:E94 (2000)); modified primers that improve hybridization selectivity (see, e.g., U.S. Pat. Nos. 6,794,142 and 6,001,611); primers with 3' modifications that are removable by 3'-5' exonuclease activity (see, e.g., U.S. Patent Application Publication No. 2003/0119150 and U.S. Pat. No. 6,482,590); primers with modified nucleobases that are removable by UV irradiation (see, e.g., Young et al., *Chem. Commun.* (Camb) 28:462 (2008)); primer modifications that are removable by thermal deprotection (see, e.g., U.S. Patent Application Publication No. 2003/0162199 and Lebedev et al., *Nucl. Acids Res.* 36:e131 (2008)); or modification of the dNTPs with thermolabile modification groups (see, e.g., U.S. Patent Application Publication No. 2003/0162199 and Koukhareva et al., *Nucl. Acids Symp. Ser.* (Oxford), 259 (2008)). Agents that are used as hot start mechanisms, such as, but not limited to, antibodies, oligonucleotides, Affibodies®, chemical modifications, etc., may be referred to as "hot start inhibitors."

In some embodiments, the hot start composition comprises an antibody specific for the polymerase. In some embodiments, the hot start composition comprises an antibody specific for the polymerase, which is bound to the polymerase. In some embodiments, the hot start composition comprises an inhibitor specific for the polymerase, which is bound to the polymerase. In some embodiments, the inhibitor comprises an Affibody®. Affibodies® are described, e.g., in US Publication 2012/0082981; see also Nord et al., 2000, *J. Biotechnol.* 80: 45-54; U.S. Pat. No. 6,602,977; Nygren, 2008, *FEBS J.* 275: 2668-2676; Nord et al., 1997, 15: 772-777; U.S. Pat. No. 5,831,012. In some embodiments, the inhibitor comprises an oligonucleotide. In some embodiments, the inhibitor comprises a chemical modification.

As used herein, dual hot start reaction mixtures comprising "at least two different mechanisms" encompass those reaction mixtures that may comprise at least two different hot start mechanisms that function similarly or use similar components. For example, dual hot start reaction mixtures can comprise reagents or reagent solutions designed for two different antibody-based hot start mechanisms, or two different oligonucleotide-based hot start mechanisms, or one antibody-based and one oligonucleotide-based hot start mechanism, or one antibody-based and one chemical modification-based hot start mechanism, or any such combination available.

Exemplary DNA Polymerases

In some embodiments the thermophilic DNA polymerase comprises a DNA polymerase catalytic domain, a 3' to 5' exonuclease domain, and/or a non-specific DNA-binding domain. In some embodiments the thermophilic DNA polymerase comprises a DNA polymerase catalytic domain, a 3' to 5' exonuclease domain, and a non-specific DNA-binding domain.

In some embodiments, the family B polymerase catalytic domain is a subfamily B3 polymerase domain. In some embodiments, the family B polymerase catalytic domain is a family B polymerase domain of a *Pyrococcus*, or a variant thereof. In some embodiments, the family B polymerase catalytic domain is a family B polymerase domain of a *Thermococcus*, or a variant thereof. In some embodiments, the family B polymerase catalytic domain is a family B polymerase domain of a *Pyrobaculum*, or a variant thereof. In some embodiments, the family B polymerase catalytic domain is a family B polymerase domain of *Pyrococcus furiosus*, or a variant thereof. In some embodiments, the family B polymerase catalytic domain is a family B polymerase domain of *Pyrococcus species* GB-D, or a variant thereof. In some embodiments, the family B polymerase catalytic domain is a family B polymerase domain of *Thermococcus kodakarensis*, or a variant thereof. In some embodiments, the family B polymerase catalytic domain is a family B polymerase domain of *Thermococcus litoralis*, or a variant thereof. In some embodiments, the family B polymerase catalytic domain is a family B polymerase domain of *Thermococcus gorgonarius*, or a variant thereof. In some embodiments, the family B polymerase catalytic domain is a family B polymerase domain of *Thermococcus* sp. 9° N-7, or a variant thereof. In some embodiments, the family B polymerase catalytic domain is a family B polymerase domain of *Pyrobaculum calidifontis*, or a variant thereof. In some embodiments, the family B polymerase catalytic domain is a family B polymerase domain of *Pyrobaculum aerophilum*, or a variant thereof.

In some embodiments, all domains of the thermophilic DNA polymerase are contained in a single polypeptide. In some embodiments, the thermophilic DNA polymerase comprises a plurality of polypeptide chains, which may be noncovalently associated or covalently associated. The plurality of polypeptide chains can include a first polypeptide comprising a polymerase catalytic domain and a second polypeptide comprising an additional domain, such as a sequence non-specific DNA-binding domain. A covalent association can include, e.g., one or more disulfide bonds or chemical conjugation using a linking compound, e.g., a chemical crosslinking agent, including, for example, succinimidyl-(N-maleimidomethyl)-cyclohexane-1-carboxylate (SMCC). Disulfide bonds and chemical conjugation are discussed further below.

In some embodiments, the thermophilic DNA polymerase comprises a sequence non-specific DNA-binding domain, e.g., a thermophilic DNA binding domain. The DNA binding domain can be, for example, present as part of a fusion protein with the polymerase catalytic domain. In some embodiments, the DNA binding domain is fused C-terminal to the polymerase catalytic domain. In some embodiments, the DNA binding domain is noncovalently associated with the polypeptide comprising the polymerase catalytic domain, e.g., in the manner of the association between sliding clamps and certain family B polymerases. In some embodiments, the polypeptide comprising the polymerase catalytic domain further comprises a sequence that noncovalently associates with an DNA binding domain, such as the PCNA-interacting sequence of a dimeric archaeal polymerase such as Pfu Pol II. As discussed, e.g., in U.S. Pat. No. 7,541,170, an DNA binding domain can provide improved processivity relative to version of the enzyme lacking the DNA binding domain. Processivity reflects the extent to which a polymerase continues to synthesize DNA (adding nucleotides in processive catalytic events) along the same template without falling off. In some embodiments, high processivity correlates to high sensitivity in amplification reactions.

In some embodiments, the DNA binding domain is covalently conjugated to the polypeptide comprising the polymerase catalytic domain. Techniques for covalent conjugation of heterologous domains are described, e.g., in BIOCONJUGATE TECHNIQUES, Hermanson, Ed., Academic Press (1996). Such techniques include, for example, derivatization for the purpose of linking the moieties to each other, either directly or through a linking compound, by methods that are well known in the art of protein chemistry. For example, in one chemical conjugation embodiment, the catalytic domain and the nucleic acid binding domain are linked using a heterobifunctional coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteines in each moiety, which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages.

In some embodiments, the DNA polymerase catalytic domain is a family B polymerase catalytic domain. In some embodiments, the DNA polymerase catalytic domain comprises an amino acid sequence having at least 90%, 95%, 98%, 99%, or 100% identity to a sequence selected from SEQ ID NOs: 4 to 6, 10 to 12, 18, 19, 22, 23, 26, 27, 32, 33, and 36 to 38.

In some embodiments, the DNA polymerase comprises a 3' to 5' exonuclease domain. In some embodiments, the 3' to 5' exonuclease domain is N-terminal to the DNA polymerase catalytic domain. The 3'-5' exonuclease domain can have error-correcting activity, also known as proofreading activity, in which the exonuclease preferentially removes a base from a nascent DNA strand/extension product/3' terminus that is not a Watson-Crick match to the template strand. In some embodiments, the 3'-5' exonuclease domain is a DEDDy archaeal exonuclease domain. In some embodiments, the 3' to 5' exonuclease domain comprises an amino acid sequence having at least 90%, 95%, 98%, 99%, or 100% identity to SEQ ID NO: 52. In some embodiments, the 3' to 5' exonuclease domain comprises an amino acid sequence having at least 90%, 95%, 98%, 99%, or 100% identity to the 3' to 5' exonuclease domain of a sequence selected from SEQ ID NOs: 1 to 3, 16, 17, 24, 25, 28, 29, 30, 31, 34, 35, 40, 41, and 69 to 71. One skilled in the art can identify the 3' to 5' exonuclease domain in any one of those sequences. For example, an exonuclease domain can be identified using BLASTP against the RefSeq database can be identified by using NCBI BLASTP to search the RefSeq database. NCBI BLASTP automatically identifies certain domains such as exonuclease domains and indicates their termini as the positions at which the domain begins and ends.

In some embodiments, the exonuclease domain is an exonuclease domain of a *Pyrococcus*. In some embodiments, the exonuclease domain is an exonuclease domain of a *Thermococcus*. In some embodiments, the exonuclease domain is an exonuclease domain of a *Pyrobaculum*. In some embodiments, the exonuclease domain is an exonuclease domain of *Pyrococcus furiosus*. In some embodiments, the exonuclease domain is an exonuclease domain of *Pyrococcus* species GB-D. In some embodiments, the exonuclease domain is an exonuclease domain of *Thermococcus kodakarensis*. In some embodiments, the exonuclease domain is an exonuclease domain of *Thermococcus litoralis*. In some embodiments, the exonuclease domain is an exonuclease domain of *Thermococcus gorgonarius*. In some embodiments, the exonuclease domain is an exonuclease domain of *Thermococcus* sp. 9° N-7. In some embodiments, the exonuclease domain is an exonuclease domain of *Pyrobaculum calidifontis*. In some embodiments, the exonuclease domain is an exonuclease domain of *Pyrobaculum aerophilum*.

In some embodiments, the thermophilic DNA polymerase comprises an inactivated or reduced-activity exonuclease domain. An inactivated exonuclease domain is a mutated version of a wild-type domain that has less than 50% of the wild-type exonuclease activity. In some embodiments, the inactivated domain has less than 40%, less than 30%, less than 25%, less than 20%, less than 15%, less than 10%, or less than 5% of the wild-type exonuclease activity. In some embodiments, the inactivated domain has less than 2%, 1%, 0.5%, 0.2%, 0.1%, 0.05%, 0.02%, or 0.01% of the wild-type exonuclease activity. A reduced-activity exonuclease domain is a mutated version of a wild-type domain that has less than 10% of the wild-type exonuclease activity. Measurement of exonuclease activity is described, for example, in *DNA Replication* $2^{nd}$, edition, by Kornberg and Baker, W.H. Freeman & Company, New York, N.Y. 1991. Examples of exo⁻ DNA polymerase mutants include those with a single mutation in Motif I and/or II (Motifs are as described, e.g., in U.S. Pat. No. 8,921,043, e.g., at FIG. 2), or a double mutation in Motif I (such as D141A and E143A, the position numbering corresponds to Pfu polymerase, SEQ ID NO: 1), that reportedly abolishes detectible exonuclease activity (see for example, VENT® (*Thermococcus litoralis*) (Kong et al. *J. Biol. Chem.* 268(3):1965-1975) (New England Biolabs, Inc. (NEB), Ipswich, Mass.); *Thermococcus* JDF-3 (U.S. Pat. No. 6,946,273, U.S. 2005/0069908); KODI (*Thermococcus kodakaraensis*) (U.S. Pat. No. 6,008,025); Pfu (*Pyrococcus furiosus*) (U.S. Pat. Nos. 5,489,523, 7,704, 712, and U.S. Pat. No. 7,659,100); and 9° N (*Thermococcus* sp.) (U.S. 2005/0123940 and Southworth et al. *Proc Natl Acad Sci USA* 93:5281-5285 (1996)); see also U.S. Pat. No. 8,921,043. In some embodiments, the exonuclease domain has a D141A, E143A, D215A, D315A, D141A/E143A, D141A/D315A, E143A/D315A, D215A/D315A, or D141A/E143A/D315A mutation. In some embodiments, the exonuclease domain has an A, N, S, T, or E residue at the position corresponding to position 141 of SEQ ID NO: 1. In some embodiments, the exonuclease domain has an A at the position corresponding to position 141 of SEQ ID NO: 1. In some embodiments, the exonuclease domain has an A at the position corresponding to position 143 of SEQ ID NO: 1.

In some embodiments, the DNA polymerase comprises a sequence non-specific DNA-binding domain. In some embodiments, the sequence non-specific DNA-binding domain is C-terminal to the DNA polymerase catalytic domain. In some embodiments, the sequence non-specific DNA-binding domain is a 7 kD DNA-binding domain. In some embodiments, the DNA binding domain is an archaeal DNA binding domain. In some embodiments, the DNA binding domain is a 7 kD DNA-binding domain, which occurs in certain archaeal small basic DNA binding proteins (see, e.g., Choli et al., Biochimica et Biophysica Acta 950:193-203, 1988; Baumann et al., Structural Biol. 1:808-819, 1994; and Gao et al, Nature Struc. Biol. 5:782-786, 1998). Additional archaeal DNA binding domains are discussed in Hardy and Martin, Extremophiles 12:235-46 (2008). In some embodiments, the sequence non-specific DNA-binding domain is an Sso7d, Sac7d, or Sac7e domain. In some embodiments, the DNA binding domain is a Pae3192 domain. In some embodiments, the DNA binding domain is a Pae0384 domain. In some embodiments, the DNA binding domain is a Ape3192 domain. In some embodiments, the DNA binding domain is an archaeal histone domain. In some embodiments, the archaeal histone domain is an HMf family archaeal histone domain (see, e.g., Starich et al., J Molec. Biol. 255:187-203, 1996; Sandman et al., Gene 150:207-208, 1994). In some embodiments, the archaeal histone domain is an HMf family archaeal histone domain from *Methanothermus*. In some embodiments, the archaeal histone domain is an HMf family archaeal histone domain from *Pyrococcus*. In some embodiments, the archaeal histone domain is an HMf family archaeal histone domain from *Methanothermus fervidus*. In some embodiments, the archaeal histone domain is an HMf family archaeal histone domain from *Pyrococcus* strain GB-3a. In some embodiments, the archaeal histone domain is a *Methanothermus* HMfA archaeal histone domain. In some embodiments, the archaeal histone domain is a *Methanothermus* HMfB archaeal histone domain. In some embodiments, the archaeal histone domain is a *Pyrococcus* HpyA1 archaeal histone domain. In some embodiments, the archaeal histone domain is a *Pyrococcus* HpyA2 archaeal histone domain. In some embodiments, the DNA binding domain is a sliding clamp, such as an archaeal PCNA homolog. Sliding clamps can exist as trimers in solution, and can form a ring-like structure with a central passage capable of accommodating double-stranded DNA. The sliding clamp forms specific interactions with the amino acids located at the C terminus of particular DNA polymerases, and tethers those polymerases to the DNA template during replication. The sliding clamp in eukaryotes is referred to as the proliferating cell nuclear antigen (PCNA), while similar proteins in other domains are often referred to as PCNA homologs. These homologs have marked structural similarity but limited sequence similarity. PCNA homologs have been identified from thermophilic Archaea (e.g., *Sulfolobus solfataricus, Pyrococcus furiosus*, etc.). Some family B polymerases in Archaea have a C terminus containing a consensus PCNA-interacting amino acid sequence and are capable of using a PCNA homolog as a processivity factor (see, e.g., Cann et al., J. Bacteriol. 181:6591-6599, 1999 and De Felice et al., J Mol. Biol. 291:47-57, 1999). These PCNA homologs are useful sequence non-specific DNA binding domains. For example, a consensus PCNA-interacting sequence can be joined to a polymerase that does not naturally interact with a PCNA homolog, thereby allowing a PCNA homolog to serve as a processivity factor for the polymerase. By way of illustration, the PCNA-interacting sequence from *Pyrococcus furiosus* Pol II (a heterodimeric DNA polymerase containing two family B-like polypeptides) can be covalently joined to a sequence based on *Pyrococcus furiosus* Pol I (a monomeric family B polymerase that does not normally interact with a PCNA homolog). The resulting fusion protein can then be allowed to associate non-covalently with the *Pyrococcus furiosus* PCNA homolog to generate a heterologous protein with increased processivity.

Nucleic acids encoding the domains of a fusion protein invention can be obtained using recombinant genetics techniques. Basic texts disclosing the general methods for doing so include Sambrook et al., MOLECULAR CLONING, A LABORATORY MANUAL ($2^{nd}$ ed. 1989); Kriegler, GENE TRANSFER AND EXPRESSION: A LABORATORY MANUAL (1990); and CURRENT PROTOCOLS IN MOLECULAR BIOLOGY (Ausubel et al., eds., 1994)). In some embodiments, the sequence non-specific DNA-binding domain comprises an amino acid sequence having at least 90%, 95%, 98%, 99%, or 100% identity to a sequence selected from SEQ ID NOs: 42 to 51.

In some embodiments, the thermophilic DNA polymerase comprises an amino acid sequence having at least 90%, 95%, 98%, 99%, or 100% identity to a sequence selected from SEQ ID NOs: 7 to 9, 13 to 15, 20, and 21.

In some embodiments, catalytic and binding domains of the polymerase are joined by a linker domain, e.g., a polypeptide sequence of 1 to about 200 amino acids in length, such as 1 to about 100, 50, 25, or 10 amino acids. In some embodiments, proline residues are incorporated into the linker to prevent the formation of significant secondary structural elements by the linker. Linkers can often be flexible amino acid subsequences that are synthesized as part of a recombinant fusion protein. For a discussion of linkers, see, e.g., US 2011/0086406 A1 including at paragraphs 83-89 thereof.

In some embodiments, the amino acid residue at the position of the family B polymerase catalytic domain amino acid sequence that aligns to position 25 of SEQ ID NO: 4 is a serine. In some embodiments, the amino acid residue at the position of the family B polymerase catalytic domain amino acid sequence that corresponds to position 25 of SEQ ID NO: 4 is a serine. In some embodiments, the thermophilic DNA polymerase comprises: (a) the consecutive amino acid residues LDFR<u>S</u>, (b) the consecutive amino acid residues FR<u>S</u>LY, or (c) the consecutive amino acid residues <u>S</u>LYPS, wherein the underlined serine residue is within 30 amino acid residues of the N-terminus of the family B polymerase catalytic domain. In some embodiments, the thermophilic DNA polymerase comprises: (a) the consecutive amino acid residues LDFRS*, (b) the consecutive amino acid residues FRS*LY, or (c) the consecutive amino acid residues S*LYPS, wherein the serine residue immediately followed by an asterisk is within 30 amino acid residues of the N-terminus of the family B polymerase catalytic domain. The asterisk is included solely to designate the serine that is within 30 amino acid residues of the N-terminus of the family B polymerase catalytic domain and does not signify a structural difference. In some embodiments, the N-terminus of the family B polymerase catalytic domain is the residue immediately preceding the conserved tyrosine shown as the second residue in the multiple sequence alignment in FIG. 2. In some embodiments, the N-terminus of the family B polymerase catalytic domain is the position immediately preceding the position corresponding to the first tyrosine in SEQ ID NO: 4. In some embodiments, the N-terminus of the family B polymerase catalytic domain is the position that aligns to position 1 of SEQ ID NO: 4. In some embodiments, the N-terminus of the family B polymerase catalytic domain is the position corresponding to the position immediately preceding a tyrosine selected from the tyrosines shown as the second residues in FIG. 2. In some embodiments, the N-terminus of the family B polymerase catalytic domain is the position immediately preceding the position that aligns to a tyrosine selected from the tyrosines shown as the second residues in FIG. 2. In some embodiments, the N-terminus of the family B polymerase catalytic domain is the position immediately preceding the position corresponding to a tyrosine selected from the tyrosines shown as the second residues in FIG. 2. The N-terminal residue in any of the foregoing embodiments can be a serine. The N-terminal residue in any of the foregoing embodiments can be a threonine. The N-terminal residue in any of the foregoing embodiments can be a glycine. The N-terminal residue in any of the foregoing embodiments can be a proline.

As will be apparent from various aspects of the discussion above, family B polymerases are well-characterized in general and are known to tolerate mutations at a number of positions. Furthermore, the following is a non-exhaustive list of patents and published applications that discuss mutations in family B polymerases and the properties of mutated family B polymerases: U.S. Pat. Nos. 8,435,775; 8,557,554; WO2007/016702; US 2003/0180741; WO 2004/011605; WO 2003/060144; and U.S. Pat. No. 9,023,633. In some embodiments, the thermophilic DNA polymerase comprises an amino acid sequence comprising at least one difference from SEQ ID NO: 1 at a position corresponding to position 15, 72, 93, 141, 143, 247, 265, 337, 385, 387, 388, 399, 400, 405, 407, 410, 485, 542, 546, 593, or 595 of SEQ ID NO: 1. In some embodiments, the thermophilic DNA polymerase comprises an amino acid sequence comprising at least one missing residue corresponding to position 92, 93, 94, or 381 of SEQ ID NO: 1. In some embodiments, the at least one difference or missing residue is in the exonuclease domain. In some embodiments, the at least one difference or missing residue is in the polymerase catalytic domain.

In some embodiments, the polymerase with the at least one difference or missing residue has an expanded substrate range relative to a polymerase without the difference or in which the residue is not missing. In some embodiments, the at least one difference comprises a G or D at the position corresponding to position 400 of SEQ ID NO: 1. In some embodiments, the at least one difference comprises an I at the position corresponding to position 407 of SEQ ID NO: 1. In some embodiments, the at least one difference comprises an I at the position corresponding to position 337 of SEQ ID NO: 1. In some embodiments, the at least one difference comprises a D at the position corresponding to position 399 of SEQ ID NO: 1. In some embodiments, the at least one difference comprises an H at the position corresponding to position 546 of SEQ ID NO: 91.

In some embodiments, the polymerase with the at least one difference or missing residue incorporates a nucleotide analog to a greater extent than a polymerase without the difference or in which the residue is not missing. In some embodiments, the at least one difference comprises an L at the position corresponding to position 410 of SEQ ID NO: 1. In some embodiments, the at least one difference comprises a T at the position corresponding to position 485 of SEQ ID NO: 1.

In some embodiments, the polymerase with the at least one difference or missing residue has reduced uracil sensitivity relative to a polymerase without the difference or in which the residue is not missing. In some embodiments, the at least one missing residue comprises a missing residue at the position corresponding to position 93 of SEQ ID NO: 1. In some embodiments, the at least one missing residue comprises a missing residue at the position corresponding to position 94 of SEQ ID NO: 1. In some embodiments, the at least one missing residue comprises a missing residue at the position corresponding to position 92 of SEQ ID NO: 1. In some embodiments, the at least one difference comprises a Q, R, E, A, K, N, or G at the position corresponding to position 93 of SEQ ID NO: 1. In some embodiments, the at least one difference comprises a Q or R at the position corresponding to position 93 of SEQ ID NO: 1. In some embodiments, an at least one difference or missing residue as discussed above in this paragraph is accompanied by at least one difference or missing residue that offsets a loss of activity. In some embodiments, the at least one difference that offsets a loss of activity comprises an R at the position corresponding to position 247 of SEQ ID NO: 1. In some embodiments, the at least one difference that offsets a loss of activity comprises an R at the position corresponding to position 265 of SEQ ID NO: 1. In some embodiments, the at least one difference that offsets a loss of activity comprises an R at the position corresponding to position 485 of SEQ ID NO: 1. In some embodiments, the at least one missing residue that offsets a loss of activity comprises a missing residue at the position corresponding to position 381 of SEQ ID NO: 1.

In some embodiments, the at least one difference comprises an R at the position corresponding to position 247 of SEQ ID NO: 1. In some embodiments, the at least one difference comprises an R at the position corresponding to position 265 of SEQ ID NO: 1. In some embodiments, the at least one difference comprises an R at the position corresponding to position 485 of SEQ ID NO: 1. In some embodiments, the at least one missing residue comprises a missing residue at the position corresponding to position 381 of SEQ ID NO: 1. In some embodiments, the at least one difference comprises an I at the position corresponding to position 15 of SEQ ID NO: 1. In some embodiments, the at least one difference comprises an R at the position corresponding to position 72 of SEQ ID NO: 1.

In some embodiments, the polymerase with the at least one difference or missing residue has an altered proofreading spectrum relative to a polymerase without the difference or in which the residue is not missing. In some embodiments, the at least one difference comprises a P or S at the position corresponding to position 387 of SEQ ID NO: 1. In some embodiments, the at least one difference comprises an E at the position corresponding to position 405 of SEQ ID NO: 1. In some embodiments, the at least one difference comprises an F at the position corresponding to position 410 of SEQ ID NO: 1. In some embodiments, the at least one difference comprises a P at the position corresponding to position 542 of SEQ ID NO: 1. In some embodiments, the at least one difference comprises a T at the position corresponding to position 593 of SEQ ID NO: 1. In some embodiments, the at least one difference comprises an S at the position corresponding to position 595 of SEQ ID NO: 1. In some embodiments, the at least one difference comprises a Q, S, N, L, or H at the position corresponding to position 385 of SEQ ID NO: 1. In some embodiments, the at least one difference comprises a P at the position corresponding to position 388 of SEQ ID NO: 1.

In some embodiments, the thermophilic DNA polymerase comprises an amino acid sequence having at least 90%, 95%, 98%, 99%, or 100% identity to a sequence selected from SEQ ID NOs: 7 to 9, 13 to 15, 20, and 21.

In some embodiments, the polymerase comprises an affinity purification tag. In some embodiments, the affinity purification tag comprises a sequence of histidines, such as 6, 7, 8, 9, or 10 consecutive histidines. The affinity purification tag can be located, e.g., at the N or C terminus of a polypeptide of the polymerase.

Exemplary Assays to Determine Polymerase Processivity, Yield, Sensitivity, and Specificity Polymerase processivity may be measured using various methods known in the art. In some embodiments, processivity refers to the number of nucleotides incorporated during a single binding event of polymerase to a primed template. As a nonlimiting example, a detectably labeled primer may be annealed to circular or linearized DNA to form a primed nucleic acid template. In measuring processivity, the primed nucleic acid template may be present in significant molar excess to the polymerase to reduce the likelihood that any one primed template will be extended more than once by a polymerase. A "significant molar excess" may be, for example, a ratio of 500:1, or 1000:1, or 2000:1, or 4000:1, or 5000:1 (primed DNA:DNA polymerase), etc., in the presence of suitable buffers and dNTPs. Nucleic acid synthesis may be initiated by adding, for example, $MgCl_2$. Nucleic acid synthesis reactions are quenched at various times after initiation, and analyzed by any appropriate method to determine the length of the product. At a polymerase concentration where the median product length does not change with time or polymerase concentration, the length corresponds to the processivity of the enzyme.

In some embodiments, yield can be demonstrated by measuring the ability of a polymerase to produce product.

In some embodiments, long PCR may be used to determine enhanced processivity and yield. For example, an enzyme with enhanced processivity typically allows the amplification of a longer amplicons (>5 kb) in shorter extension times compared to an enzyme with relatively lower processivity.

Other methods of assessing efficiency of the polymerases of the invention can be determined by those of ordinary skill in the art using standard assays of the enzymatic activity of a given modification enzyme.

The sensitivity of a polymerase may be determined by measuring the yield of nucleic acid synthesis product in a series of reactions with differing copy numbers of nucleic acid template. The lower the template copy number at which the polymerase produces detectable product, the more sensitive the polymerase.

In some embodiments, specificity of a polymerase may be measured by determining the ability of the polymerase to discriminate between matched primer/template duplexes and mismatched primer/template duplexes. In some embodiments, specificity is a measure of the difference in the relative yield of two reactions, one of which employs a matched primer, and one of which employs a mismatched primer. In some embodiments, an enzyme with increased discrimination will have a higher relative yield with the matched primer than with the mismatched primer. In some embodiments, a ratio of the yield with the matched primer versus the mismatched primer is determined. In some embodiments, the ratio can be compared to the yield obtained under the same reaction conditions using the parental polymerase.

DNA Synthesis Methods; Kits, Compositions, Systems, and Apparatuses.

Provided herein are methods of synthesizing or amplifying DNA and related kits, compositions, systems, and apparatuses involving a hot start composition comprising at least one antibody described herein and at least one polymerase. In some embodiments, reagents for nucleic acid synthesis are provided. In some embodiments, reagents for nucleic acid synthesis include any one or any combination of target polynucleotides, particles attached with capture primers, solution-phase primers, fusion primers, other additional primers, enzymes (e.g., polymerases), accessory proteins (e.g., recombinase, recombinase loading protein, single-stranded binding protein, helicase or topoisomerase), nucleotides, divalent cations, binding partners, co-factors and/or buffer. In some embodiments, reagents for nucleic acid synthesis include a dUTPase as an accessory protein.

In some embodiments, the disclosure relates generally to compositions, as well as related systems, methods, kits and apparatuses, comprising one or more nucleotides. In some embodiments, the compositions (and related methods, systems, kits and apparatuses) includes one type, or a mixture of different types of nucleotides. A nucleotide comprises any compound that can bind selectively to, or can be polymerized by, a polymerase. Typically, but not necessarily, selective binding of the nucleotide to the polymerase is followed by polymerization of the nucleotide into a nucleic acid strand by the polymerase. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In some embodiments, one or more phosphorus atoms in the chain can be part of a phosphate group having P and O. In some embodiments, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In some embodiments, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281.

Some examples of nucleotides that can be used in the disclosed compositions (and related methods, systems, kits and apparatuses) include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof. In some embodiments, a nucleotide can include a purine or pyrimidine base, including adenine, guanine, cytosine, thymine, uracil or inosine. In some embodiments, a nucleotide includes dATP, dGTP, dCTP, dTTP and/or dUTP.

In some embodiments, the nucleotide is unlabeled. In some embodiments, the nucleotide comprises a label and referred to herein as a "labeled nucleotide". In some embodiments, the label can be in the form of a fluorescent dye attached to any portion of a nucleotide including a base, sugar or any intervening phosphate group or a terminal phosphate group, i.e., the phosphate group most distal from the sugar.

In some embodiments, the disclosure relates generally to compositions, as well as related systems, methods, kits and apparatuses, comprising any one or any combination of capture primers, reverse solution-phase primers, fusion primers, target polynucleotides and/or nucleotides that are non-labeled or attached to at least one label. In some embodiments, the label comprises a detectable moiety. In some embodiments, the label can generate, or cause to generate, a detectable signal. In some embodiments, the detectable signal can be generated from a chemical or physical change (e.g., heat, light, electrical, pH, salt concentration, enzymatic activity, or proximity events). For example, a proximity event can include two reporter moieties approaching each other, or associating with each other, or binding each other. In some embodiments, the detectable signal can be detected optically, electrically, chemically, enzymatically, thermally, or via mass spectroscopy or Raman spectroscopy. In some embodiments, the label can include compounds that are luminescent, photoluminescent, electroluminescent, bioluminescent, chemiluminescent, fluorescent, phosphorescent or electrochemical. In some embodiments, the label can include compounds that are fluorophores, chromophores, radioisotopes, haptens, affinity tags, atoms or enzymes. In some embodiments, the label comprises a moiety not typically present in naturally occurring nucleotides. For example, the label can include fluorescent, luminescent or radioactive moieties.

In some embodiments, the nucleic acid synthesis reaction includes a cycled amplification reaction, such as a polymerase chain reaction (PCR) (U.S. Pat. Nos. 4,683,195 and 4,683,202 both granted to Mullis). Multiple examples of PCR according to this disclosure are provided below. In some embodiments, the nucleic acid synthesis reaction includes an isothermal reaction, such as an isothermal self-sustained sequence reaction (Kwoh 1989 Proceedings National Academy of Science USA 86:1173-1177; WO 1988/10315; and U.S. Pat. Nos. 5,409,818, 5,399,491, and 5,194,370), or a recombinase polymerase amplification (RPA) (U.S. Pat. No. 5,223,414 to Zarling, U.S. Pat. Nos. 5,273,881 and 5,670,316 both to Sena, and U.S. Pat. Nos. 7,270,981, 7,399,590, 7,435,561, 7,666,598, 7,763,427, 8,017,339, 8,030,000, 8,062,850, and 8,071,308). In some embodiments, an antibody described herein that is bound to the polymerase is first un-bound from the polymerase, for example, by denaturation, prior to nucleic acid synthesis (such as amplification). In some embodiments, the antibody is un-bound by the application of heat, e.g., as a first step in the cycled amplification reaction.

PCR is a nucleic acid synthesis reaction in which the reaction mixture is subjected to reaction cycles, each reaction cycle comprising a denaturation period and at least one annealing and/or extension period, resulting if successful in synthesis of copies of a nucleic acid template in at least the initial cycles, and copies of the copies in at least the later cycles, generally resulting in exponential amplification of the template pair of primers are provided that bind at each end of a target region, on opposite strands such that they each prime synthesis toward the other primer. The reaction is thermocycled so as to drive denaturation of the substrate in a high temperature step, annealing of the primers at a lower temperature step, and extension at a temperature which may be but is not necessarily higher than that of the annealing step. Exponential amplification occurs because the products of one cycle can serve as template in the next cycle. As noted above, in some embodiments, an antibody described herein that is bound to the polymerase is first un-bound from the polymerase, for example, by denaturation, prior to PCR. In some embodiments, the antibody is un-bound by the application of heat, e.g., as a first step in the cycled amplification reaction.

An embodiment of isothermal self-sustained sequence reaction, also sometimes referred to as transcription-mediated amplification or TMA, involves synthesizing single-stranded RNA, single-stranded DNA and double-stranded DNA. The single-stranded RNA is a first template for a first primer, the single-stranded DNA is a second template for a second primer, and the double stranded DNA is a third template for synthesis of a plurality of copies of the first template. A sequence of the first primer or the second primer is complementary to a sequence of a target nucleic acid and a sequence of the first primer or the second primer is homologous to a sequence of the target nucleic acid. In an embodiment of an isothermal self-sustained sequence reaction, a first cDNA strand is synthesized by extension of the first primer along the target by an enzyme with RNA-dependent DNA polymerase activity, such as a reverse transcriptase. The first primer comprises a polymerase binding sequence (PBS) such as a PBS for a DNA-dependent RNA polymerase, such as T7, T3, or SP6 RNA polymerase. The first primer comprising a PBS is sometimes referred to as a promoter-primer. The first cDNA strand is rendered single-stranded, such as by denaturation or by degradation of the RNA, such as by an RNase H. The second primer then anneals to the first cDNA strand and is extended to form a second cDNA strand by a DNA polymerase activity. Forming the second cDNA strand renders the cDNA double-stranded, including the PBS. RNA can then be synthesized from the cDNA, which comprises the PBS, by a DNA-dependent RNA polymerase, such as T7, T3, or SP6 RNA polymerase, thereby providing a template for further events (extension of the first primer, rendering the product single-stranded, extension of the second primer, and RNA synthesis). Exponential amplification occurs because the RNA product can subsequently serve as a template and also because RNA products can be generated repeatedly from a cDNA comprising the PBS.

An embodiment of RPA can be performed isothermally and employs a recombinase to promote strand invasion of a double-stranded template by forward and reverse primers. The 3' ends of the primers are extended, displacing template strands at least in part. Subsequent strand invasion/annealing events, including to previously produced extension products, occur and are followed by extension, resulting in amplification. In some embodiments, recombinase activity is supported by the presence of one or more recombinase accessory proteins, such as a recombinase loading protein and/or single-stranded binding protein.

In some embodiments, the disclosure relates generally to compositions, and related methods, systems, kits and apparatuses, comprising a nucleic acid synthesis reaction (synthesis condition) that can be conducted under thermocycling or isothermal conditions, or a combination of both types of conditions. For example, the synthesis condition can include alternating between thermocycling and isothermal synthesis conditions, in any order.

In some embodiments thermocycling synthesis conditions comprise a nucleic acid synthesis reaction mixture that is subjected to an elevated temperature for a period of time that is sufficient to denature at least about 30-95% of the double-stranded target nucleic acids, and then subjected to a lower temperature for a period of time that is sufficient to permit hybridization between the single-stranded target nucleic acids and any of the primers (e.g., capture primer, reverse solution-phase primer, or fusion primer). In some embodiments, the increase and decrease temperature cycle is repeated at least once.

In some embodiments isothermal synthesis conditions comprise a nucleic acid synthesis reaction mixture that is subjected to a temperature variation which is constrained within a limited range during at least some portion of the synthesis, including for example a temperature variation is within about 20° C., or about 10° C., or about 5° C., or about 1-5° C., or about 0.1-1° C., or less than about 0.1° C.

In some embodiments, an isothermal nucleic acid synthesis reaction can be conducted for about 2, 5, 10, 15, 20, 30, 40, 50, 60 or 120 minutes, or longer. In some embodiments, an isothermal nucleic acid synthesis reaction can be conducted for at least about 2 minutes. In some embodiments, an isothermal nucleic acid synthesis reaction can be conducted for about 120 minutes or less. In some embodiments, an isothermal nucleic acid synthesis reaction can be conducted for about 2 to about 120 minutes. In some embodiments, an isothermal nucleic acid synthesis reaction can be conducted for about 2 to about 60 minutes. In some embodiments, an isothermal nucleic acid synthesis reaction can be conducted for about 60 to about 120 minutes. In some embodiments, an isothermal nucleic acid synthesis reaction can be conducted for about 2 to about 5 minutes. In some embodiments, an isothermal nucleic acid synthesis reaction can be conducted for about 5 to about 10 minutes. In some embodiments, an isothermal nucleic acid synthesis reaction can be conducted for about 10 to about 15 minutes. In some embodiments, an isothermal nucleic acid synthesis reaction can be conducted for about 10 to about 15 minutes. In some embodiments, an isothermal nucleic acid synthesis reaction can be conducted for about 10 to about 15 minutes. In some embodiments, an isothermal nucleic acid synthesis reaction can be conducted for about 15 to about 20 minutes. In some embodiments, an isothermal nucleic acid synthesis reaction can be conducted for about 20 to about 30 minutes. In some embodiments, an isothermal nucleic acid synthesis reaction can be conducted for about 30 to about 40 minutes. In some embodiments, an isothermal nucleic acid synthesis reaction can be conducted for about 40 to about 50 minutes. In some embodiments, an isothermal nucleic acid synthesis reaction can be conducted for about 50 to about 60 minutes.

In some embodiments, an isothermal nucleic acid synthesis reaction can be conducted at about 15-30° C., or about 30-45° C., or about 45-60° C., or about 60-75° C., or about 75-90° C., or about 90-93° C., or about 93-99° C.

In some embodiments, the disclosure relates generally to methods, and related compositions, systems, kits and apparatuses, that further include an enrichment step. In some embodiments, an enrichment step comprises a pre-amplification reaction. See, e.g., U.S. Pat. No. 8,815,546 B2. As a nonlimiting example, a pre-amplification reaction may comprise random primers to amplify a portion, even a substantial portion, of the nucleic acid template in a sample. In this manner, the overall amount of nucleic acid template may be increased prior to a sequence-specific nucleic acid synthesis reaction.

In some embodiments, an amplified population of nucleic acids can include an affinity moiety. For example, in conducting any of the nucleic acid synthesis methods according to the present teachings, a solution-phase/reverse primer that is attached to an affinity moiety (e.g., biotin) can be used to conduct a synthesis reaction to produce an amplified population of nucleic acids that are attached to the affinity moiety. In some embodiments, the enrichment step comprises forming a enrichment complex by binding the affinity moiety (which is attached to the amplified population of nucleic acids) with a purification particle (e.g., paramagnetic bead) that is attached to a receptor moiety (e.g., streptavidin). An example of purification particles include MyOne™ Beads from Dynabeads, which are paramagnetic beads attached to streptavidin. In some embodiments, a magnet can be used to separate/remove the enrichment complex from amplified population of nucleic acids that lack the affinity moiety. In some embodiments, the enrichment step can be repeated at least once. In some embodiment, the enrichment step is followed by one or more washing step.

In some embodiments, the disclosure relates generally to methods, and related compositions, systems, kits and apparatuses that further include at least one washing step. The washing step can be conducted at any time during the workflow for nucleic acid synthesis. In some embodiments, a washing step can remove excess or unreacted components of the nucleic acid synthesis or enrichment reactions.

In some embodiments, any of the nucleic acid synthesis methods, or enrichment steps, according to the present teachings, can be conducted manually or by automation. In some embodiments, any one or any combination of the steps can be conducted manually or by automation, including: conducting a nucleic acid synthesis reaction, enriching, and/or washing. For example, any reagents for a nucleic acid synthesis, enrichment or washing, can be deposited into, or removed from, a reaction vessel via manual or automated modes.

In various embodiments, the disclosure relates to compositions comprising at least one antibody described herein. In various embodiments, the disclosure relates to compositions comprising at least one antibody described herein and at least one polymerase. In some embodiments, the composition is a hot start composition. In some such embodiments, the composition is a dual hot start composition. In some embodiments, the dual hot start composition comprises at least two different hot start mechanisms that are used to inhibit or substantially inhibit the polymerase activity at a first temperature. Such hot start mechanisms include, but are not limited to, antibodies or combinations of antibodies that block DNA polymerase activity at lower temperatures, antibody mimetics or combinations of antibody mimetics that block DNA polymerase activity at lower temperatures (such as, for example, Affibodies®), oligonucleotides that block DNA polymerase activity at lower temperatures (such as, for example, aptamers), reversible chemical modifications of the DNA polymerase that dissociate at elevated temperatures, amino acid modifications of the DNA polymerase that provide reduced activity at lower temperatures, fusion proteins that include hyperstable DNA binding domains and topoisomerase, other temperature dependent ligands that inhibit the DNA polymerase, single stranded binding proteins that sequester primers at lower temperatures, modified primers or modified dNTPs. Hot start compositions, in some embodiments, comprise at least one polymerase with or without a hot start chemical modification, at least one antibody described herein, at least one hot start aptamer, and/or at least one hot start Affibody®. In some embodiments, a hot start composition comprises at least one polymerase with or without a hot start chemical modification, at least one antibody described herein and at least one hot start aptamer or at least one hot start Affibody®. In some embodiments, a hot start composition comprises at least one polymerase with or without a hot start chemical modification, at least one hot start Affibody® and at least one antibody described herein. In some embodiments, a hot start composition comprises a polymerase with or without a hot start chemical modification, at least one antibody described herein, and a hot start aptamer or a hot start Affibody®. In some embodiments, a hot start composition comprises a polymerase with or without a hot start chemical modification, a hot start Affibody®, and at least one antibody described herein. In some embodiments, a hot start composition comprises a polymerase with or without a hot start chemical modification, at least one antibody described herein, and a hot start Affibody®. In some embodiments, a hot start composition comprises a polymerase with or without a hot start chemical modification, at least one antibody described herein, and a hot start aptamer.

In some embodiments, a composition comprises one or more detergents, one or more protein stabilizers, and/or at least one UTPase. In some embodiments, a composition comprises one or more detergents, one or more protein stabilizers, and at least one UTPase. In some embodiments, a composition comprises at least one monovalent cationic salt, at least one divalent cationic salt, and/or at least one dNTP. In some embodiments, a composition further comprises at least one dye. In some embodiments, a composition comprises additional stabilizers that increase the density of the composition.

Nonlimiting exemplary detergents that may be used in the compositions provided herein include nonionic, ionic (anionic, cationic) and zwitterionic detergents. Exemplary such detergents include, but are not limited to, Hecameg (6-O—(N-Heptylcarbamoyl)-methyl-α-D-glucopyranoside), Triton X-200, Brij-58, CHAPS, n-Dodecyl-b-D-maltoside, NP-40, sodium dodecyl sulphate (SDS), TRITON® X-15, TRITON® X-35, TRITON® X-45, TRITON® X-100, TRITON® X-102, TRITON® X-114, TRITON® X-165, TRITON® X-305, TRITON® X-405, TRITON® X-705, Tween® 20 and/or ZWITTERGENT®. Other detergents may also be suitable, as may be determined by one of skill in the art. See, e.g., U.S. Pat. No. 7,972,828B2, U.S. Pat. No. 8,980,333B2 U.S. Publication No. 2008/0145910; U.S. Publication No. 2008/0064071; U.S. Pat. Nos. 6,242,235; 5,871,975; and U.S. Pat. No. 6,127,155 for exemplary detergents.

Nonlimiting exemplary protein stabilizers that may be used in the compositions provided herein include BSA, inactive polymerases (such as inactivated Taq polymerase; see, e.g., US Publication No. 2011/0059490), and apotransferrin. Further nonlimiting exemplary stabilizers that may be used in the compositions provided herein include glycerol, trehalose, lactose, maltose, galactose, glucose, sucrose, dimethyl sulfoxide (DMSO), polyethylene glycol, and sorbitol.

Nonlimiting exemplary UTPases that may be used in the compositions provided herein include UTPases from thermophilic bacteria. See, e.g., *PNAS*, 2002, 99: 596-601.

Nonlimiting exemplary dyes that may be used in the compositions provided herein include xylene cyanol FF, tartrazine, phenol red, quinoline yellow, zylene cyanol, Brilliant Blue, Patent Blue, indigocarmine, acid red 1, m-cresol purple, cresol red, neutral red, bromocresol green, acid violet 5, bromo phenol blue, and orange G (see, e.g., U.S. Pat. No. 8,663,925 B2). Additional nonlimiting exemplary dyes are described, e.g., in U.S. Pat. No. 6,942,964. One skilled in the art will appreciate that any dye that does not inhibit nucleic acid synthesis by the polymerases described herein may be used.

In some embodiments, a storage composition is provided comprising at least one antibody provided herein, at least one polymerase, at least one protein stabilizer, and at least one UTPase, in a buffer suitable for storage. In some embodiments, a storage composition is provided comprising at least one antibody provided herein, at least one polymerase, at least one Affibody®, at least one protein stabilizer, and at least one UTPase, in a buffer suitable for storage. In some embodiments, a storage composition is provided comprising two antibodies described herein, at least one polymerase, a polymerase, a protein stabilizer, and a UTPase, in a buffer suitable for storage. In some embodiments, the storage buffer comprises a buffering agent (such as Tris HCl), a salt (such as KCl or NaCl), a stabilizer (such as glycerol), a reducing agent (such as DTT), a divalent cation chelating agent (such as EDTA), and a detergent (such as hecameg and/or Triton X-200 and/or NP-40 and/or Tween-20, etc.). In some embodiments, the storage composition comprises 0.5 to 5 units (U), or 0.5 to 3 U, or 1 to 3 U, or 2 U of polymerase per µl. In some embodiments, the storage composition comprises 0.05 to 1 mg/ml, or 0.05 to 0.5 mg/ml, or 0.1 to 0.5 mg/ml, or 0.1 to 0.3 mg/ml of each antibody. In some embodiments, the storage composition comprises 0.1 to 10 mg/ml, or 0.1 to 5 mg/ml, or 0.5 to 5 mg/ml, or 0.5 to 2 mg/ml of each hot start Affibody®. In some embodiments, the storage composition comprises 0.5 to 5 mg/ml, or 1 to 5 mg/ml, or 1 to 3 mg/ml of each protein stabilizer.

In some embodiments, a reaction composition is provided, comprising at least one polymerase bound to an antibody described herein, at least one buffering agent (such as Tris HCl), at least one monovalent cationic salt (such as KCl or NaCl), at least one divalent cationic salt (such as $MgCl_2$), at least one detergent (such as hecameg and/or Triton X-200 and/or NP-40 and/or Tween-20, etc.), and at least one dNTP. In some embodiments, the composition comprises dATP, dCTP, dGTP, and dTTP. In some embodiments, the reaction composition further comprises at least one dye. In some embodiments, for example when the composition is to be loaded on a gel, the reaction composition comprises additional stabilizers that increase the density of the composition, such as polyethylene glycol (e.g., PEG 4000) and/or sucrose. PEG 4000 may be included, in some embodiments, at a concentration of 0.5-2%, or about 1%; and sucrose may be included, in some embodiments, at a concentration of 1-5%, or 1-3%, or about 2% (or 2-10%, or 2-6%, or about 4% for a 2× reaction composition). In some embodiments, the buffering agent (such as Tris HCl) is present at a concentration of 5-50 mM, or 5-30 mM, or 5-20 mM (or 10-100 mM, or 10-60 mM, or 10-40 mM for a 2× reaction composition). In some embodiments, the monovalent cation (such as K+ or Na+) is present at a concentration of 50-300 mM, or 50-200 mM, or 75-150 mM, or about 110 mM (or 100-600 mM, or 100-400 mM, or 150-300 mM, or about 220 mM for a 2× reaction composition). In some embodiments, a detergent (such as hecameg) is present at a concentration of 0.05-0.3%, or 0.1-0.2%, or about 0.15% (or 0.01-0.6%, or 0.2-0.4%, or about 0.3% for a 2× reaction composition). In some embodiments, the $Mg^{2-}$ or $Mn^{2+}$ is present at a concentration of 0.5-5 mM, or 0.5-3 mM, or about 1.5 mM (or 1-10 mM, or 1-6 mM, or about 3 mM for a 2× reaction composition). In some embodiments, each dNTP is present at a concentration of 0.05-1 mM, or 0.1-0.8 mM, or 0.1-0.6 mM, or 0.1-0.4 mM, or about 0.2 mM (or 0.1-2 mM, or 0.2-1.6 mM, or 0.2-1.2 mM, or 0.2-0.8 mM, or about 0.4 mM for a 2× reaction composition).

PCR enhancing factors may also be used to improve efficiency of the amplification. As used herein, a "PCR enhancing factor" or a "Polymerase Enhancing Factor" (PEF) refers to a complex or protein possessing polynucleotide polymerase enhancing activity (Hogrefe et al., 1997, Strategies 10:93-96; and U.S. Pat. No. 6,183,997, both of which are hereby incorporated by references). For Pfu DNA polymerase, for example, PEF may comprise either P45 in native form (as a complex of P50 and P45) or as a recombinant protein. In the native complex of Pfu P50 and P45, only P45 exhibits PCR enhancing activity. The P50 protein is similar in structure to a bacterial flavoprotein. The P45 protein is similar in structure to dCTP deaminase and dUTPase, but it functions only as a dUTPase converting dUTP to dUMP and pyrophosphate. PEF, according to the present disclosure, may also be selected from the group consisting of: an isolated or purified naturally occurring polymerase enhancing protein obtained from an archaeabacteria source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, supra).

In some embodiments, a reaction composition further comprises ingredients that enhance nucleic acid synthesis from high GC-content templates. In some such embodiments, the reaction composition comprises glycerol, DMSO, and/or ammonium sulphate. In some embodiments, the reaction composition comprises glycerol, DMSO, and ammonium sulphate. In some embodiments, glycerol is present in the reaction composition at a concentration of 5-20%, or 5-15%, or about 10%. In some embodiments, DMSO is present in the reaction composition at a concentration of 1-10%, or 3-10%, or 3-7%, or about 5%. In some embodiments, ammonium sulphate is present in the reaction composition at 10-50 mM, or 15-40 mM, or 20-30 mM, or about 25 mM.

In some embodiments, a reaction composition is provided at 2×, 5×, 10×, etc. concentration, in which case, the concentrations discussed herein are multiplied (e.g., as noted above; doubled for 2×). A 2× reaction composition is typically diluted by 2-fold, for example, when the template nucleic acid and/or primers are added to the composition.

In some embodiments, a reaction composition comprises nucleic acid template and at least one primer for nucleic acid synthesis. In some embodiments, each primer is included in the reaction composition at a concentration of 0.1-0.8 μM, or 0.1-0.5 μM, or 0.2-0.4 μM, or about 0.3 μM. One skilled in the art will appreciate that the template nucleic acid may be provided at a wide range of concentrations, which lower limit, in some embodiments, may be determined by the sensitivity of the polymerase.

In some embodiments, the composition comprises at least one PCR inhibitor. In some embodiments, the PCR inhibitor comprises xylan, heparin, humic acid, or SDS. In some embodiments, methods according to the disclosure comprise amplifying DNA in the presence of at least one PCR inhibitor. In some embodiments, the PCR inhibitor comprises xylan. In some embodiments, the PCR inhibitor comprises heparin.

In various embodiments, the composition may be an aqueous composition. In various embodiments, the composition may be a lyophilized composition. In some embodiments, the composition comprises a cryoprotectant and/or a preservative and/or other additives known to those skilled in the art. Nonlimiting exemplary cryoprotectants and preservatives include, for example, the stabilizers and reducing agents described herein.

Nucleic Acids; Vectors; Host Cells; Methods of Production and/or Purification.

Provided herein are nucleic acids comprising a sequence encoding a heavy chain and/or a light chain of an antibody described herein. In some embodiments, the nucleic acid is operably linked to a promoter. In some embodiments, the promoter is a promoter for a bacteriophage RNA polymerase, such as a T7 promoter. In some embodiments, the nucleic acid is codon-optimized for expression in a host cell, such as a microorganism, e.g., a bacterium, such as *E. coli*, or a eukaryotic cell, such as a CHO cell.

Also provided herein are vectors comprising any of the nucleic acids encoding a heavy chain and/or light chain of an antibody described herein. In some embodiments, the vector is a plasmid. In some embodiments, the vector is an expression vector. In some embodiments, the vector contains a selectable marker. In some embodiments, the vector is capable of being propagated in a microorganism, e.g., a bacterium, such as *E. coli*, or a eukaryotic cell, such as a CHO cell.

Also provided herein are host cells comprising any of the nucleic acids discussed above. Also provided herein are host cells comprising any of the vectors comprising a sequence encoding a polymerase according to this disclosure discussed above. In some embodiments, the host cell is a microorganism, e.g., a bacterium, such as *E. coli*. In some embodiments, the host cell is a eukaryotic cell, such as a CHO cell. In some embodiments, the host cell further comprises a nucleic acid encoding a heterologous RNA polymerase. In some embodiments, the heterologous RNA polymerase is a bacteriophage RNA polymerase, such as bacteriophage T7 RNA polymerase. In some embodiments, the heterologous RNA polymerase is operably linked to a promoter, such as an inducible promoter, e.g., a lac-inducible promoter. In some embodiments, the host cell is of a protease-deficient strain. In some embodiments, the host cell is *E. coli* BL-21. In some embodiments, the host cell, such as BL-21, is modified to carry tRNA genes encoding tRNAs with rarer anticodons (for example, argU, ileY, leuW, and proL tRNA genes).

Also provided herein are hybridomas cells that express an antibody described herein.

Also provided herein are methods of producing and/or purifying an antibody according to this disclosure. In some embodiments, such a method comprises culturing at least one host cell that expresses the antibody. In some embodiments, such a method comprises isolating the antibody from the host cells. In some embodiments, the isolating comprises lysing the host cells. In some embodiments, denatured host proteins are removed, e.g., by centrifugation. In some embodiments, the isolating comprises isolating secreted antibody from the media in which the host cells are cultured. In some embodiments, the antibody is purified via chromatography, such as protein A and/or protein G chromatography.

EXAMPLES

The following examples are provided to illustrate certain disclosed embodiments and are not to be construed as limiting the scope of this disclosure in any way.

Example 1. Generation of Hybridomas Cell Lines Producing Monoclonal Antibodies Against *Pyrococcus* DNA Polymerase BALB/c mice were immunized with *Pyrococcus* DNA polymerase with a sequence non-specific DNA binding domain (*Pyrococcus* DNA polymerase-DBD, SEQ ID NO: 13) by injecting subcutaneously 50 µg of the antigen mixed with complete Freund's adjuvant. Four weeks later mice were boosted in a similar way with 50 µg of the antigen in incomplete Freund's adjuvant. Four weeks later mice were boosted again with 50 µg of the antigen without an adjuvant. During immunization, the titers of antibodies specific to the antigen were tested by an enzyme-linked immunosorbent assay (ELISA). On day 3 after the last boost the hybridization was performed.

Spleen cells of the immunized mice were fused with mouse myeloma Sp 2/0 cells lacking an enzyme hypoxanthine phosphoribosyl transferase, non-proliferating in a selective HAT medium with hypoxanthine-aminopterin-thymidine ($10^{-4}$M hypoxanthine, $1,6 \times 10^{-5}$M thymidine, $4 \times 10^{-7}$M aminopterin), non-producing hybridomas lines nor their chains. Before fusion, the cells are in a logarithmic growth phase. The fusion was performed by incubating the cells for 2 min with 50% polyethylene glycol solution (PEG-4000) in Dulbecco modified Eagle's medium (DMEM) with 10% dimethylsulfoxide (DMSO). The ratio of myeloma and spleen cells during fusion was 1:4.75. After fusion, the cells were washed with serum-free DMEM, resuspended in a selective HAT medium and seeded into hybridoma plates at a density $5 \times 10^5$ cells per well. Hybrid clones appeared on days 5-10 after fusion. Growth medium was tested by an indirect ELISA for the antibodies specific to *Pyrococcus* DNA polymerase-DBD (SEQ ID NO: 13). Every 4-5 days one-half of the growth medium was changed. For a first time HAT medium was changed to HT medium containing hypoxanthine-thymidine ($10^{-4}$M hypoxanthine and $1,6 \times 10^{-4}$M thymidine). Later on, HT medium was changed stepwise to normal growth medium. Hybrid clones producing antibodies specific to *Pyrococcus* DNA polymerase-DBD were cloned by limiting dilution assay. The clones appeared on days 4-7 after cloning. They were monitored microscopically and tested by an indirect ELISA. Selected positive clones were propagated in vitro and then frozen for a long-term storage in liquid nitrogen. In total, 46 stable hybridomas clones producing monoclonal antibodies against *Pyrococcus* DNA polymerase-DBD were generated.

Example 2. Determination of the Specificity and Isotypes of Monoclonal Antibodies The specificity of monoclonal antibodies produced by 46 hybridoma clones was tested by enzyme-linked immunoassays (ELISA) and Western blot. Immunoglobulin isotypes were determined by ELISA using antibody isotyping kit (Sigma, USA).

It was determined by using these assays that all monoclonal antibodies are of IgG isotype and specifically recognize *Pyrococcus* DNA polymerase-DBD (SEQ ID NO: 13) both in ELISA and Western blot.

The antibody subtypes are listed in Table 1.

TABLE 1

List of monoclonal antibodies generated against *Pyrococcus* DNA polymerase-DBD

| Clone | IgG subtype |
|---|---|
| 1B6 | IgG1 |
| 1D10 | IgG1 |
| 1G11 | IgG1 |
| 1A12 | IgG1 |
| 1E4 | IgG1 |
| 2D1 | IgG1 |
| 2A7 | IgG1 |
| 3F7 | IgG1 |
| 3E2 | IgG2a |
| 3H11 | IgG1 |
| 4B5 | IgG1 |
| 4B1 | IgG1 |
| 4D7 | IgG1 |
| 4G6 | IgG1 |
| 4E3 | IgG1 |
| 5D3 | IgG1 |
| 5G4 | IgG1 |
| 6C10 | IgG1 |
| 6G10 | IgG1 |
| 6F3 | IgG1 |
| 6A12 | IgG2b |
| 7B3 | IgG1 |
| 7F6 | IgG1 |
| 8D9 | IgG1 |
| 9C3 | IgG1 |
| 10C2 | IgG1 |
| 10F6 | IgG1 |
| 10C12 | IgG1 |
| 10B12 | IgG1 |
| 11B6 | IgG1 |
| 11F10 | IgG2a |
| 11H12 | IgG1 |
| 11H3 | IgG1 |
| 12F6 | IgG1 |
| 12C3 | IgG1 |
| 13B2 | IgG1 |
| 13F3 | IgG1 |
| 13G5 | IgG2a |
| 13C7 | IgG1 |
| 14G12 | IgG1 |
| 14A10 | IgG2b |
| 14A11 | IgG1 |
| 14H10 | IgG1 |
| 15D2 | IgG1 |
| 15E1 | IgG1 |
| 15E7 | IgG2a |
| 15G6 | IgG1 |
| 15B12 | IgG1 |
| 16A6 | IgG1 |

TABLE 1-continued

List of monoclonal antibodies generated
against *Pyrococcus* DNA polymerase-DBD

| Clone | IgG subtype |
|---|---|
| 16B11 | IgG1 |
| 17F6 | IgG1 |
| 17D1 | IgG1 |
| 18G1 | IgG1 |
| 18E12 | IgG2b |
| 18A2 | IgG1 |
| 18B7 | IgG1 |

Example 3. Purification of Monoclonal Antibodies by Affinity Chromatography

Hybridoma growth medium was collected and subjected to affinity chromatography using recombinant protein A-Sepharose Fast Flow (GE Healthcare). The purified antibodies were eluted pH 3.0.

Concentrations of purified antibodies were determined spectrophotometrically by absorbance at 280 nm. The yield of monoclonal antibodies varied in a range of 10-20 micrograms from 1 ml of hybridoma growth medium.

Purified monoclonal antibodies were dialyzed against phosphate-buffered saline (PBS) and neutralizing activity determined as described below.

Example 4. Investigation of the Fine Specificity, Affinity and Neutralizing Activity of Monoclonal Antibodies The affinity of monoclonal antibodies was determined by measuring their apparent dissociation constants (kD) by an indirect ELISA (Table 2).

The neutralizing activity of the purified monoclonal antibodies was determined as follows. DNaseAlert test (AM1970) was used to determine inhibition of exonuclease activity. A primer extension assay was used to determine inhibition of polymerase activity. Briefly, the primer extension assay used substrate prepared by annealing a primer (sequence 5'-GCCAGGGTTTTCCCAGTCACGA-3', SEQ ID NO: 72) to single-stranded M13 DNA. Reactions contained 5 μM of the substrate, dNTPs (0.2 mM each) and 5 μM of EvaGreen dye. The extension of the substrate by the polymerase at 52° C. was evaluated by fluorescence measurement every 4 seconds (200 cycles) using a Rotor-Gene Q instrument (BioRad). In total, 23 neutralizing antibodies were identified (Table 2). The molar ratio of enzyme: antibody at which inhibition was achieved is indicated.

The neutralizing monoclonal antibodies (n=23) were tested for their reactivity with the DNA-binding domain (Sso7d) of *Pyrococcus* DNA polymerase-DBD (SEQ ID NO: 42) by Western blotting. As a positive control, *Pyrococcus* DNA polymerase-DBD (SEQ ID NO: 13) was used (FIG. 3).

TABLE 2

The affinity, domain specificity and neutralizing activity of monoclonal antibodies.

| Clone | Reactivity with Sso7d | Inhibition of polymerase activity | Inhibition of exonuclease activity | Apparent Kd, M |
|---|---|---|---|---|
| 1B6 | − | 1:100 | 1:100 | $1.0 \cdot 10^{-10}$ |
| 2A7 | − | 1:100 | 1:100 | $1.3 \cdot 10^{-10}$ |
| 5D3 | − | 1:20 | 1:71 | $2.9 \cdot 10^{-10}$ |
| 8D9 | − | 1:20 | 1:100 | $3.0 \cdot 10^{-9}$ |
| 13G5 | − | 1:20 | 1:100 | $2.8 \cdot 10^{-11}$ |
| 6A12 | − | 1:100 | 1:100 | $8.0 \cdot 10^{-9}$ |
| 12C3 | − | 1:75 | 1:75 | $2.8 \cdot 10^{-10}$ |
| 17F6 | − | 1:100 | 1:100 | $3.3 \cdot 10^{-10}$ |
| 6G10 | − | 1:80 | — | $2.7 \cdot 10^{-10}$ |
| 4G6 | − | 1:100 | −+(1:100) | $3.4 \cdot 10^{-10}$ |
| 10F6 | − | 1:50 | −+(1:54) | $7.9 \cdot 10^{-10}$ |
| 6C10 | − | — | 1:73 | $2.1 \cdot 10^{-10}$ |
| 1A12 | − | — | 1:100 | $7.9 \cdot 10^{-10}$ |
| 4B5 | − | — | 1:100 | $1.0 \cdot 10^{-9}$ |
| 4D7 | − | — | 1:100 | $3.2 \cdot 10^{-10}$ |
| 14A10 | − | — | 1:100 | $5.2 \cdot 10^{-10}$ |
| 15E1 | − | — | 1:100 | $2.3 \cdot 10^{-10}$ |
| 10B12 | + | 1:60 | 1:60 | $3.6 \cdot 10^{-10}$ |
| 10C12 | + | 1:100 | 1:100 | $7.5 \cdot 10^{-10}$ |
| 18B7 | + | 1:100 | 1:100 | $2.3 \cdot 10^{-10}$ |
| 4B1 | + | — | 1:100 | $2.0 \cdot 10^{-10}$ |
| 4E3 | + | — | 1:100 | $3.2 \cdot 10^{-10}$ |
| 7B3 | + | — | 1:100 | $4.2 \cdot 10^{-10}$ |

Antibodies 2A7 and 5D3 were selected for sequencing. The sequences of the light chain and heavy chain variable regions, as well as the predicted CDRs, are shown in the table of sequences, below.

```
                       Table of Sequences

SEQ
ID
NO    Description               Sequence

1     Pfu DNA polymerase (GenBank    MILDVDYITE EGKPVIRLFK KENGKFKIEH DRTFRPYIYA
      Acc.No. WP_011011325.1)        LLRDDSKIEE VKKITGERHG KIVRIVDVEK VEKKFLGKPI
      amino acid sequence            TVWKLYLEHP QDVPTIREKV REHPAVVDIF EYDIPFAKRY
                                     LIDKGLIPME GEEELKILAF DIETLYHEGE EFGKGPIIMI
                                     SYADENEAKV ITWKNIDLPY VEVVSSEREM IKRFLRIIRE
                                     KDPDIIVTYN GDSFDFPYLA KRAEKLGIKL TIGRDGSEPK
                                     MQRIGDMTAV EVKGRIHFDL YHVITRTINL PTYTLEAVYE
                                     AIFGKPKEKV YADEIAKAWE SGENLERVAK YSMEDAKATY
                                     ELGKEFLPME IQLSRLVGQP LWDVSRSSTG NLVEWFLLRK
                                     AYERNEVAPN KPSEEEYQRR LRESYTGGFV KEPEKGLWEN
                                     IVYLDFRALY PSIIITHNVS PDTLNLEGCK NYDIAPQVGH
                                     KFCKDIPGFI PSLLGHLLEE RQKIKTKMKE TQDPIEKILL
                                     DYRQKAIKLL ANSFYGYYGY AKARWYCKEC AESVTAWGRK
                                     YIELVWKELE EKFGFKVLYI DTDGLYATIP GGESEEIKKK
                                     ALEFVKYINS KLPGLLELEY EGFYKRGFFV TKKRYAVIDE
                                     EGKVITRGLE IVRRDWSEIA KETQARVLET ILKHGDVEEA
                                     VRIVKEVIQK LANYEIPPEK LAIYEQITRP LHEYKAIGPH
```

| SEQ ID NO | Description | Sequence |
|---|---|---|
| | | VAVAKKLAAK GVKIKPGMVI GYIVLRGDGP ISNRAILAEE YDPKKHKYDA EYYIENQVLP AVLRILEGFG YRKEDLRYQK TRQVGLTSWL NIKKS |
| 2 | Pfu GenBank WP_011011325.1 R762Q amino acid sequence | MILDVDYITE EGKPVIRLFK KENGKFKIEH DRTFRPYIYA LLRDDSKIEE VKKITGERHG KIVRIVDVEK VEKKFLGKPI TVWKLYLEHP QDVPTIREKV REHPAVVDIF EYDIPFAKRY LIDKGLIPME GEEELKILAF DIETLYHEGE EFGKGPIIMI SYADENEAKV ITWKNIDLPY VEVVSSEREM IKRFLRIIRE KDPDIIVTYN GDSFDFPYLA KRAEKLGIKL TIGRDGSEPK MQRIGDMTAV EVKGRIHFDL YHVITRTINL PTYTLEAVYE AIFGKPKEKV YADEIAKAWE SGENLERVAK YSMEDAKATY ELGKEFLPME IQLSRLVGQP LWDVSRSSTG NLVEWFLLRK AYERNEVAPN KPSEEEYQRR LRESYTGGFV KEPEKGLWEN IVYLDFRALY PSIIITHNVS PDTLNLEGCK NYDIAPQVGH KFCKDIPGFI PSLLGHLLEE RQKIKTKMKE TQDPIEKILL DYRQKAIKLL ANSFYGYYGY AKARWYCKEC AESVTAWGRK YIELVWKELE EKFGFKVLYI DTDGLYATIP GGESEEIKKK ALEFVKYINS KLPGLLELEY EGFYKRGFFV TKKRYAVIDE EGKVITRGLE IVRRDWSEIA KETQARVLET ILKHGDVEEA VRIVKEVIQK LANYEIPPEK LAIYEQITRP LHEYKAIGPH VAVAKKLAAK GVKIKPGMVI GYIVLRGDGP ISNRAILAEE YDPKKHKYDA EYYIENQVLP AVLRILEGFG YRKEDLRYQK TQQVGLTSWL NIKKS |
| 3 | Pfu GenBank WP_011011325.1 A408S R762Q amino acid sequence | MILDVDYITE EGKPVIRLFK KENGKFKIEH DRTFRPYIYA LLRDDSKIEE VKKITGERHG KIVRIVDVEK VEKKFLGKPI TVWKLYLEHP QDVPTIREKV REHPAVVDIF EYDIPFAKRY LIDKGLIPME GEEELKILAF DIETLYHEGE EFGKGPIIMI SYADENEAKV ITWKNIDLPY VEVVSSEREM IKRFLRIIRE KDPDIIVTYN GDSFDFPYLA KRAEKLGIKL TIGRDGSEPK MQRIGDMTAV EVKGRIHFDL YHVITRTINL PTYTLEAVYE AIFGKPKEKV YADEIAKAWE SGENLERVAK YSMEDAKATY ELGKEFLPME IQLSRLVGQP LWDVSRSSTG NLVEWFLLRK AYERNEVAPN KPSEEEYQRR LRESYTGGFV KEPEKGLWEN IVYLDFRSLY PSIIITHNVS PDTLNLEGCK NYDIAPQVGH KFCKDIPGFI PSLLGHLLEE RQKIKTKMKE TQDPIEKILL DYRQKAIKLL ANSFYGYYGY AKARWYCKEC AESVTAWGRK YIELVWKELE EKFGFKVLYI DTDGLYATIP GGESEEIKKK ALEFVKYINS KLPGLLELEY EGFYKRGFFV TKKRYAVIDE EGKVITRGLE IVRRDWSEIA KETQARVLET ILKHGDVEEA VRIVKEVIQK LANYEIPPEK LAIYEQITRP LHEYKAIGPH VAVAKKLAAK GVKIKPGMVI GYIVLRGDGP ISNRAILAEE YDPKKHKYDA EYYIENQVLP AVLRILEGFG YRKEDLRYQK TQQVGLTSWL NIKKS |
| 4 | Pfu DNA polymerase (GenBank Acc. No. WP_011011325.1), catalytic domain amino acid sequence | SYTGGFV KEPEKGLWEN IVYLDFRALY PSIIITHNVS PDTLNLEGCK NYDIAPQVGH KFCKDIPGFI PSLLGHLLEE RQKIKTKMKE TQDPIEKILL DYRQKAIKLL ANSFYGYYGY AKARWYCKEC AESVTAWGRK YIELVWKELE EKFGFKVLYI DTDGLYATIP GGESEEIKKK ALEFVKYINS KLPGLLELEY EGFYKRGFFV TKKRYAVIDE EGKVITRGLE IVRRDWSEIA KETQARVLET ILKHGDVEEA VRIVKEVIQK LANYEIPPEK LAIYEQITRP LHEYKAIGPH VAVAKKLAAK GVKIKPGMVI GYIVLRGDGP ISNRAILAEE YDPKKHKYDA EYYIENQVLP AVLRILEGFG YRKEDLRYQK TRQVGL |
| 5 | Pfu DNA polymerase (GenBank Acc. No. WP_011011325.1) catalytic domain R762Q amino acid sequence | SYTGGFV KEPEKGLWEN IVYLDFRALY PSIIITHNVS PDTLNLEGCK NYDIAPQVGH KFCKDIPGFI PSLLGHLLEE RQKIKTKMKE TQDPIEKILL DYRQKAIKLL ANSFYGYYGY AKARWYCKEC AESVTAWGRK YIELVWKELE EKFGFKVLYI DTDGLYATIP GGESEEIKKK ALEFVKYINS KLPGLLELEY EGFYKRGFFV TKKRYAVIDE EGKVITRGLE IVRRDWSEIA KETQARVLET ILKHGDVEEA VRIVKEVIQK LANYEIPPEK LAIYEQITRP LHEYKAIGPH VAVAKKLAAK GVKIKPGMVI GYIVLRGDGP ISNRAILAEE YDPKKHKYDA EYYIENQVLP AVLRILEGFG YRKEDLRYQK TQQVGL |
| 6 | Pfu DNA polymerase (GenBank Acc. No. WP_011011325.1) catalytic domain A408S R762Q amino acid sequence | SYTGGFV KEPEKGLWEN IVYLDFRSLY PSIIITHNVS PDTLNLEGCK NYDIAPQVGH KFCKDIPGFI PSLLGHLLEE RQKIKTKMKE TQDPIEKILL DYRQKAIKLL ANSFYGYYGY AKARWYCKEC AESVTAWGRK YIELVWKELE EKFGFKVLYI DTDGLYATIP GGESEEIKKK ALEFVKYINS KLPGLLELEY |

Table of Sequences

| SEQ ID NO | Description | Sequence |
|---|---|---|
| | | EGFYKRGFFV TKKRYAVIDE EGKVITRGLE IVRRDWSEIA KETQARVLET ILKHGDVEEA VRIVKEVIQK LANYEIPPEK LAIYEQITRP LHEYKAIGPH VAVAKKLAAK GVKIKPGMVI GYIVLRGDGP ISNRAILAEE YDPKKHKYDA EYYIENQVLP AVLRILEGFG YRKEDLRYQK TQQVGL |
| 7 | Pfu GenBank WP_011011325.1 with DNA binding domain amino acid sequence | miLDVDYITE EGKPVIRLFK KENGKFKIEH DRTFRPYIYA LLRDDSKIEE VKKITGERHG KIVRIVDVEK VEKKFLGKPI TVWKLYLEHP QDVPTIREKV REHPAVVDIF EYDIPFAKRY LIDKGLIPME GEEELKILAF DIETLYHEGE EFGKGPIIMI SYADENEAKV ITWKNIDLPY VEVVSSEREM IKRFLRIIRE KDPDIIVTYN GDSFDFPYLA KRAEKLGIKL TIGRDGSEPK MQRIGDMTAV EVKGRIHFDL YHVITRTINL PTYTLEAVYE AIFGKPKEKV YADEIAKAWE SGENLERVAK YSMEDAKATY ELGKEFLPME IQLSRLVGQP LWDVSRSSTG NLVEWFLLRK AYERNEVAPN KPSEEEYQRR LRESYTGGFV KEPEKGLWEN IVYLDFRALY PSIIITHNVS PDTLNLEGCK NYDIAPQVGH KFCKDIPGFI PSLLGHLLEE RQKIKTKMKE TQDPIEKILL DYRQKAIKLL ANSFYGYYGY AKARWYCKEC AESVTAWGRK YIELVWKELE EKFGFKVLYI DTDGLYATIP GGESEEIKKK ALEFVKYINS KLPGLLELEY EGFYKRGFFV TKKRYAVIDE EGKVITRGLE IVRRDWSEIA KETQARVLET ILKHGDVEEA VRIVKEVIQK LANYEIPPEK LAIYEQITRP LHEYKAIGPH VAVAKKLAAK GVKIKPGMVI GYIVLRGDGP ISNRAILAEE YDPKKHKYDA EYYIENQVLP AVLRILEGFG YRKEDLRYQK TRQVGLTSWL NIKKSGTGGG GATVKFKYKG EEKEVDISKI KKVWRVGKMI SFTYDEGGGK TGRGAVSEKD APKELLQMLE KQKK |
| 8 | Pfu GenBank WP_011011325.1 R762Q with DNA binding domain amino acid sequence | MILDVDYITE EGKPVIRLFK KENGKFKIEH DRTFRPYIYA LLRDDSKIEE VKKITGERHG KIVRIVDVEK VEKKFLGKPI TVWKLYLEHP QDVPTIREKV REHPAVVDIF EYDIPFAKRY LIDKGLIPME GEEELKILAF DIETLYHEGE EFGKGPIIMI SYADENEAKV ITWKNIDLPY VEVVSSEREM IKRFLRIIRE KDPDIIVTYN GDSFDFPYLA KRAEKLGIKL TIGRDGSEPK MQRIGDMTAV EVKGRIHFDL YHVITRTINL PTYTLEAVYE AIFGKPKEKV YADEIAKAWE SGENLERVAK YSMEDAKATY ELGKEFLPME IQLSRLVGQP LWDVSRSSTG NLVEWFLLRK AYERNEVAPN KPSEEEYQRR LRESYTGGFV KEPEKGLWEN IVYLDFRALY PSIIITHNVS PDTLNLEGCK NYDIAPQVGH KFCKDIPGFI PSLLGHLLEE RQKIKTKMKE TQDPIEKILL DYRQKAIKLL ANSFYGYYGY AKARWYCKEC AESVTAWGRK YIELVWKELE EKFGFKVLYI DTDGLYATIP GGESEEIKKK ALEFVKYINS KLPGLLELEY EGFYKRGFFV TKKRYAVIDE EGKVITRGLE IVRRDWSEIA KETQARVLET ILKHGDVEEA VRIVKEVIQK LANYEIPPEK LAIYEQITRP LHEYKAIGPH VAVAKKLAAK GVKIKPGMVI GYIVLRGDGP ISNRAILAEE YDPKKHKYDA EYYIENQVLP AVLRILEGFG YRKEDLRYQK TQQVGLTSWL NIKKSGTGGG GATVKFKYKG EEKEVDISKI KKVWRVGKMI SFTYDEGGGK TGRGAVSEKD APKELLQMLE KQKK |
| 9 | Pfu GenBank WP_011011325.1 A408S R762Q with DNA binding domain amino acid sequence | MILDVDYITE EGKPVIRLFK KENGKFKIEH DRTFRPYIYA LLRDDSKIEE VKKITGERHG KIVRIVDVEK VEKKFLGKPI TVWKLYLEHP QDVPTIREKV REHPAVVDIF EYDIPFAKRY LIDKGLIPME GEEELKILAF DIETLYHEGE EFGKGPIIMI SYADENEAKV ITWKNIDLPY VEVVSSEREM IKRFLRIIRE KDPDIIVTYN GDSFDFPYLA KRAEKLGIKL TIGRDGSEPK MQRIGDMTAV EVKGRIHFDL YHVITRTINL PTYTLEAVYE AIFGKPKEKV YADEIAKAWE SGENLERVAK YSMEDAKATY ELGKEFLPME IQLSRLVGQP LWDVSRSSTG NLVEWFLLRK AYERNEVAPN KPSEEEYQRR LRESYTGGFV KEPEKGLWEN IVYLDFRSLY PSIIITHNVS PDTLNLEGCK NYDIAPQVGH KFCKDIPGFI PSLLGHLLEE RQKIKTKMKE TQDPIEKILL DYRQKAIKLL ANSFYGYYGY AKARWYCKEC AESVTAWGRK YIELVWKELE EKFGFKVLYI DTDGLYATIP GGESEEIKKK ALEFVKYINS KLPGLLELEY EGFYKRGFFV TKKRYAVIDE EGKVITRGLE IVRRDWSEIA KETQARVLET ILKHGDVEEA VRIVKEVIQK LANYEIPPEK LAIYEQITRP LHEYKAIGPH VAVAKKLAAK GVKIKPGMVI GYIVLRGDGP ISNRAILAEE YDPKKHKYDA EYYIENQVLP AVLRILEGFG YRKEDLRYQK TQQVGLTSWL NIKKSGTGGG GATVKFKYKG EEKEVDISKI KKVWRVGKMI SFTYDEGGGK TGRGAVSEKD APKELLQMLE |

Table of Sequences

| SEQ ID NO | Description | Sequence |
|---|---|---|
| | | KQKK |
| 10 | *Pyrococcus* catalytic domain amino acid sequence | SYAGGFVKEP EKGLWENIVS LDFRALYPSI IITHNVSPDT<br>LNREGCRNYD VAPEVGHKFC KDFPGFIPSL LKRLLDERQK<br>IKTKMKASQD PIEKIMLDYR QRAIKILANS YYGYYGYAKA<br>RWYCKECAES VTAWGREYIE FVWKELEEKF GFKVLYIDTD<br>GLYATIPGGK SEEIKKKALE FVDYINAKLP GLLELEYEGF<br>YKRGFFVTKK KYALIDEEGK IITRGLEIVR RDWSEIAKET<br>QARVLEAILK HGNVEEAVRI VKEVTQKLSK YEIPPEKLAI<br>YEQITRPLHE YKAIGPHVAV AKRLAAKGVK IKPGMVIGYI<br>VLRGDGPISN RAILAEEYDP RKHKYDAEYY IENQVLPAVL<br>RILEGFGYRK EDLRWQKTKQ TGL |
| 11 | *Pyrococcus* K762Q catalytic domain amino acid sequence | SYAGGFVKEP EKGLWENIVS LDFRALYPSI IITHNVSPDT<br>LNREGCRNYD VAPEVGHKFC KDFPGFIPSL LKRLLDERQK<br>IKTKMKASQD PIEKIMLDYR QRAIKILANS YYGYYGYAKA<br>RWYCKECAES VTAWGREYIE FVWKELEEKF GFKVLYIDTD<br>GLYATIPGGK SEEIKKKALE FVDYINAKLP GLLELEYEGF<br>YKRGFFVTKK KYALIDEEGK IITRGLEIVR RDWSEIAKET<br>QARVLEAILK HGNVEEAVRI VKEVTQKLSK YEIPPEKLAI<br>YEQITRPLHE YKAIGPHVAV AKRLAAKGVK IKPGMVIGYI<br>VLRGDGPISN RAILAEEYDP RKHKYDAEYY IENQVLPAVL<br>RILEGFGYRK EDLRWQKTQQ TGL |
| 12 | *Pyrococcus* A408S K762Q catalytic domain amino acid sequence | SYAGGFVKEP EKGLWENIVS LDFRSLYPSI IITHNVSPDT<br>LNREGCRNYD VAPEVGHKFC KDFPGFIPSL LKRLLDERQK<br>IKTKMKASQD PIEKIMLDYR QRAIKILANS YYGYYGYAKA<br>RWYCKECAES VTAWGREYIE FVWKELEEKF GFKVLYIDTD<br>GLYATIPGGK SEEIKKKALE FVDYINAKLP GLLELEYEGF<br>YKRGFFVTKK KYALIDEEGK IITRGLEIVR RDWSEIAKET<br>QARVLEAILK HGNVEEAVRI VKEVTQKLSK YEIPPEKLAI<br>YEQITRPLHE YKAIGPHVAV AKRLAAKGVK IKPGMVIGYI<br>VLRGDGPISN RAILAEEYDP RKHKYDAEYY IENQVLPAVL<br>RILEGFGYRK EDLRWQKTQQ TGL |
| 69 | *Pyrococcus* DNA polymerase sequence including exonuclease domain and catalytic domain | MILDADYITE EGKPVIRLFK KENGEFKIEH DRTFRPYIYA<br>LLKDDSKIEE VKKITAERHG KIVRIVDAEK VEKKFLGRPI<br>TVWRLYFEHP QDVPTIREKI REHSAVVDIF EYDIPFAKRY<br>LIDKGLIPME GDEELKLLAF DIETLYHEGE EFGKGPIIMI<br>SYADEEEAKV ITWKKIDLPY VEVVSSEREM IKRFLKIIRE<br>KDPDIIITYN GDSFDLPYLA KRAEKLGIKL TIGRDGSEPK<br>MQRIGDMTAV EVKGRIHFDL YHVIRRTINL PTYTLEAVYE<br>AIFGKPKEKV YADEIAKAWE TGEGLERVAK YSMEDAKATY<br>ELGKEFFPME AQLSRLVGQP LWDVSRSSTG NLVEWFLLRK<br>AYERNELAPN KPDEREYERR LRESYAGGFV KEPEKGLWEN<br>IVSLDFRALY PSIIITHNVS PDTLNREGCR NYDVAPEVGH<br>KFCKDFPGFI PSLLKRLLDE RQKIKTKMKA SQDPIEKIML<br>DYRQRAIKIL ANSYYGYYGY AKARWYCKEC AESVTAWGRE<br>YIEFVWKELE EKFGFKVLYI DTDGLYATIP GGKSEEIKKK<br>ALEFVDYINA KLPGLLELEY EGFYKRGFFV TKKKYALIDE<br>EGKIITRGLE IVRRDWSEIA KETQARVLEA ILKHGNVEEA<br>VRIVKEVTQK LSKYEIPPEK LAIYEQITRP LHEYKAIGPH<br>VAVAKRLAAK GVKIKPGMVI GYIVLRGDGP ISNRAILAEE<br>YDPRKHKYDA EYYIENQVLP AVLRILEGFG YRKEDLRWQK<br>TKQTGL |
| 70 | *Pyrococcus* DNA polymerase sequence including exonuclease domain and catalytic domain, K762Q | MILDADYITE EGKPVIRLFK KENGEFKIEH DRTFRPYIYA<br>LLKDDSKIEE VKKITAERHG KIVRIVDAEK VEKKFLGRPI<br>TVWRLYFEHP QDVPTIREKI REHSAVVDIF EYDIPFAKRY<br>LIDKGLIPME GDEELKLLAF DIETLYHEGE EFGKGPIIMI<br>SYADEEEAKV ITWKKIDLPY VEVVSSEREM IKRFLKIIRE<br>KDPDIIITYN GDSFDLPYLA KRAEKLGIKL TIGRDGSEPK<br>MQRIGDMTAV EVKGRIHFDL YHVIRRTINL PTYTLEAVYE<br>AIFGKPKEKV YADEIAKAWE TGEGLERVAK YSMEDAKATY<br>ELGKEFFPME AQLSRLVGQP LWDVSRSSTG NLVEWFLLRK<br>AYERNELAPN KPDEREYERR LRESYAGGFV KEPEKGLWEN<br>IVSLDFRALY PSIIITHNVS PDTLNREGCR NYDVAPEVGH<br>KFCKDFPGFI PSLLKRLLDE RQKIKTKMKA SQDPIEKIML<br>DYRQRAIKIL ANSYYGYYGY AKARWYCKEC AESVTAWGRE<br>YIEFVWKELE EKFGFKVLYI DTDGLYATIP GGKSEEIKKK<br>ALEFVDYINA KLPGLLELEY EGFYKRGFFV TKKKYALIDE<br>EGKIITRGLE IVRRDWSEIA KETQARVLEA ILKHGNVEEA<br>VRIVKEVTQK LSKYEIPPEK LAIYEQITRP LHEYKAIGPH |

Table of Sequences

| SEQ ID NO | Description | Sequence |
|---|---|---|
| | | VAVAKRLAAK GVKIKPGMVI GYIVLRGDGP ISNRAILAEE YDPRKHKYDA EYYIENQVLP AVLRILEGFG YRKEDLRWQK TQQTGL |
| 71 | *Pyrococcus* DNA polymerase sequence including exonuclease domain and catalytic domain, A408S K762Q | MILDADYITE EGKPVIRLFK KENGEFKIEH DRTFRPYIYA LLKDDSKIEE VKKITAERHG KIVRIVDAEK VEKKFLGRPI TVWRLYFEHP QDVPTIREKI REHSAVVDIF EYDIPFAKRY LIDKGLIPME GDEELKLLAF DIETLYHEGE EFGKGPIIMI SYADEEEAKV ITWKKIDLPY VEVVSSEREM IKRFLKIIRE KDPDIIITYN GDSFDLPYLA KRAEKLGIKL TIGRDGSEPK MQRIGDMTAV EVKGRIHFDL YHVIRRTINL PTYTLEAVYE AIFGKPKEKV YADEIAKAWE TGEGLERVAK YSMEDAKATY ELGKEFFPME AQLSRLVGQP LWDVSRSSTG NLVEWFLLRK AYERNELAPN KPDEREYERR LRESYAGGFV KEPEKGLWEN IVSLDFRSLY PSIIITHNVS PDTLNREGCR NYDVAPEVGH KFCKDFPGFI PSLLKRLLDE RQKIKTKMKA SQDPIEKIML DYRQRAIKIL ANSYYGYYGY AKARWYCKEC AESVTAWGRE YIEFVWKELE EKFGFKVLYI DTDGLYATIP GGKSEEIKKK ALEFVDYINA KLPGLLELEY EGFYKRGFFV TKKKYALIDE EGKIITRGLE IVRRDWSEIA KETQARVLEA ILKHGNVEEA VRIVKEVTQK LSKYEIPPEK LAIYEQITRP LHEYKAIGPH VAVAKRLAAK GVKIKPGMVI GYIVLRGDGP ISNRAILAEE YDPRKHKYDA EYYIENQVLP AVLRILEGFG YRKEDLRWQK TQQTGL |
| 13 | *Pyrococcus* DNA polymerase sequence including exonuclease domain and DNA binding domain | MILDADYITE EGKPVIRLFK KENGEFKIEH DRTFRPYIYA LLKDDSKIEE VKKITAERHG KIVRIVDAEK VEKKFLGRPI TVWRLYFEHP QDVPTIREKI REHSAVVDIF EYDIPFAKRY LIDKGLIPME GDEELKLLAF DIETLYHEGE EFGKGPIIMI SYADEEEAKV ITWKKIDLPY VEVVSSEREM IKRFLKIIRE KDPDIIITYN GDSFDLPYLA KRAEKLGIKL TIGRDGSEPK MQRIGDMTAV EVKGRIHFDL YHVIRRTINL PTYTLEAVYE AIFGKPKEKV YADEIAKAWE TGEGLERVAK YSMEDAKATY ELGKEFFPME AQLSRLVGQP LWDVSRSSTG NLVEWFLLRK AYERNELAPN KPDEREYERR LRESYAGGFV KEPEKGLWEN IVSLDFRALY PSIIITHNVS PDTLNREGCR NYDVAPEVGH KFCKDFPGFI PSLLKRLLDE RQKIKTKMKA SQDPIEKIML DYRQRAIKIL ANSYYGYYGY AKARWYCKEC AESVTAWGRE YIEFVWKELE EKFGFKVLYI DTDGLYATIP GGKSEEIKKK ALEFVDYINA KLPGLLELEY EGFYKRGFFV TKKKYALIDE EGKIITRGLE IVRRDWSEIA KETQARVLEA ILKHGNVEEA VRIVKEVTQK LSKYEIPPEK LAIYEQITRP LHEYKAIGPH VAVAKRLAAK GVKIKPGMVI GYIVLRGDGP ISNRAILAEE YDPRKHKYDA EYYIENQVLP AVLRILEGFG YRKEDLRWQK TKQTGLTSWL NIKKSGTGGG GATVKFKYKG EEKEVDISKI KKVWRVGKMI SFTYDEGGGK TGRGAVSEKD APKELLQMLE KQKK |
| 14 | *Pyrococcus* DNA polymerase sequence including exonuclease domain and DNA binding domain, K762Q | MILDADYITE EGKPVIRLFK KENGEFKIEH DRTFRPYIYA LLKDDSKIEE VKKITAERHG KIVRIVDAEK VEKKFLGRPI TVWRLYFEHP QDVPTIREKI REHSAVVDIF EYDIPFAKRY LIDKGLIPME GDEELKLLAF DIETLYHEGE EFGKGPIIMI SYADEEEAKV ITWKKIDLPY VEVVSSEREM IKRFLKIIRE KDPDIIITYN GDSFDLPYLA KRAEKLGIKL TIGRDGSEPK MQRIGDMTAV EVKGRIHFDL YHVIRRTINL PTYTLEAVYE AIFGKPKEKV YADEIAKAWE TGEGLERVAK YSMEDAKATY ELGKEFFPME AQLSRLVGQP LWDVSRSSTG NLVEWFLLRK AYERNELAPN KPDEREYERR LRESYAGGFV KEPEKGLWEN IVSLDFRALY PSIIITHNVS PDTLNREGCR NYDVAPEVGH KFCKDFPGFI PSLLKRLLDE RQKIKTKMKA SQDPIEKIML DYRQRAIKIL ANSYYGYYGY AKARWYCKEC AESVTAWGRE YIEFVWKELE EKFGFKVLYI DTDGLYATIP GGKSEEIKKK ALEFVDYINA KLPGLLELEY EGFYKRGFFV TKKKYALIDE EGKIITRGLE IVRRDWSEIA KETQARVLEA ILKHGNVEEA VRIVKEVTQK LSKYEIPPEK LAIYEQITRP LHEYKAIGPH VAVAKRLAAK GVKIKPGMVI GYIVLRGDGP ISNRAILAEE YDPRKHKYDA EYYIENQVLP AVLRILEGFG YRKEDLRWQK TQQTGLTSWL NIKKSGTGGG GATVKFKYKG EEKEVDISKI KKVWRVGKMI SFTYDEGGGK TGRGAVSEKD APKELLQMLE KQKK |
| 15 | *Pyrococcus* DNA polymerase sequence including exonuclease | MILDADYITE EGKPVIRLFK KENGEFKIEH DRTFRPYIYA LLKDDSKIEE VKKITAERHG KIVRIVDAEK VEKKFLGRPI |

Table of Sequences

| SEQ ID NO | Description | Sequence |
|---|---|---|
| | domain and sequence non-specific DNA binding domain, A408S K762Q | TVWRLYFEHP QDVPTIREKI REHSAVVDIF EYDIPFAKRY LIDKGLIPME GDEELKLLAF DIETLYHEGE EFGKGPIIMI SYADEEEAKV ITWKKIDLPY VEVVSSEREM IKRFLKIIGL KDPDIIITYN GDSFDLPYLA KRAEKLGIKL TIGRDGSEPK MQRIGDMTAV EVKGRIHFDL YHVIRRTINL PTYTLEAVYE AIFGKPKEKV YADEIAKAWE TGEGLERVAK YSMEDAKATY ELGKEFFPME AQLSRLVGQP LWDVSRSSTG NLVEWFLLRK AYERNELAPN KPDEREYERR LRESYAGGFV KEPEKGLWEN IVSLDFRSLY PSIIITHNVS PDTLNREGCR NYDVAPEVGH KFCKDFPGFI PSLLKRLLDE RQKIKTKMKA SQDPIEKIML DYRQRAIKIL ANSYYGYYGY AKARWYCKEC AESVTAWGRE YIEFVWKELE EKFGFKVLYI DTDGLYATIP GGKSEEIKKK ALEFVDYINA KLPGLLELEY EGFYKRGFFV TKKKYALIDE EGKIITRGLE IVRRDWSEIA KETQARVLEA ILKHGNVEEA VRIVKEVTQK LSKYEIPPEK LAIYEQITRP LHEYKAIGPH VAVAKRLAAK GVKIKPGMVI GYIVLRGDGP ISNRAILAEE YDPRKHKYDA EYYIENQVLP AVLRILEGFG YRKEDLRWQK TQQTGLTSWL NIKKSGTGGG GATVKFKYKG EEKEVDISKI KKVWRVGKMI SFTYDEGGGK TGRGAVSEKD APKELLQMLE KQKK |
| 16 | Deep Vent DNA polymerase | MILDADYITE DGKPIIRIFK KENGEFKVEY DRNFRPYIYA LLKDDSQIDE VRKITAERHG KIVRIIDAEK VRKKFLGRPI EVWRLYFEHP QDVPAIRDKI REHSAVIDIF EYDIPFAKRY LIDKGLIPME GDEELKLLAF DIETLYHEGE EFAKGPIIMI SYADEEEAKV ITWKKIDLPY VEVVSSEREM IKRFLKVIRE KDPDVIITYN GDSFDLPYLV KRAEKLGIKL PLGRDGSEPK MQRLGDMTAV EIKGRIHFDL YHVIRRTINL PTYTLEAVYE AIFGKPKEKV YAHEIAEAWE TGKGLERVAK YSMEDAKVTY ELGREFFPME AQLSRLVGQP LWDVSRSSTG NLVEWYLLRK AYERNELAPN KPDEREYERR LRESYAGGYV KEPEKGLWEG LVSLDFRSLY PSIIITHNVS PDTLNREGCR EYDVAPEVGH KFCKDFPGFI PSLLKRLLDE RQEIKRKMKA SKDPIEKKML DYRQRAIKIL ANSYYGYYGY AKARWYCKEC AESVTAWGRE YIEFVRKELE EKFGFKVLYI DTDGLYATIP GAKPEEIKKK ALEFVDYINA KLPGLLELEY EGFYVRGFFV TKKKYALIDE EGKIITRGLE IVRRDWSEIA KETQAKVLEA ILKHGNVEEA VKIVKEVTEK LSKYEIPPEK LVIYEQITRP LHEYKAIGPH VAVAKRLAAR GVKVRPGMVI GYIVLRGDGP ISKRAILAEE FDLRKHKYDA EYYIENQVLP AVLRILEAFG YRKEDLRWQK TKQTGLTAWL NIKKK |
| 17 | K762Q variant of Deep Vent DNA polymerase amino acid sequence | MILDADYITE DGKPIIRIFK KENGEFKVEY DRNFRPYIYA LLKDDSQIDE VRKITAERHG KIVRIIDAEK VRKKFLGRPI EVWRLYFEHP QDVPAIRDKI REHSAVIDIF EYDIPFAKRY LIDKGLIPME GDEELKLLAF DIETLYHEGE EFAKGPIIMI SYADEEEAKV ITWKKIDLPY VEVVSSEREM IKRFLKVIRE KDPDVIITYN GDSFDLPYLV KRAEKLGIKL PLGRDGSEPK MQRLGDMTAV EIKGRIHFDL YHVIRRTINL PTYTLEAVYE AIFGKPKEKV YAHEIAEAWE TGKGLERVAK YSMEDAKVTY ELGREFFPME AQLSRLVGQP LWDVSRSSTG NLVEWYLLRK AYERNELAPN KPDEREYERR LRESYAGGYV KEPEKGLWEG LVSLDFRSLY PSIIITHNVS PDTLNREGCR EYDVAPEVGH KFCKDFPGFI PSLLKRLLDE RQEIKRKMKA SKDPIEKKML DYRQRAIKIL ANSYYGYYGY AKARWYCKEC AESVTAWGRE YIEFVRKELE EKFGFKVLYI DTDGLYATIP GAKPEEIKKK ALEFVDYINA KLPGLLELEY EGFYVRGFFV TKKKYALIDE EGKIITRGLE IVRRDWSEIA KETQAKVLEA ILKHGNVEEA VKIVKEVTEK LSKYEIPPEK LVIYEQITRP LHEYKAIGPH VAVAKRLAAR GVKVRPGMVI GYIVLRGDGP ISKRAILAEE FDLRKHKYDA EYYIENQVLP AVLRILEAFG YRKEDLRWQK TQQTGLTAWL NIKKK |
| 18 | Deep Vent DNA polymerase catalytic domain amino acid sequence | SYAGGYV KEPEKGLWEG LVSLDFRSLY PSIIITHNVS PDTLNREGCR EYDVAPEVGH KFCKDFPGFI PSLLKRLLDE RQEIKRKMKA SKDPIEKKML DYRQRAIKIL ANSYYGYYGY AKARWYCKEC AESVTAWGRE YIEFVRKELE EKFGFKVLYI DTDGLYATIP GAKPEEIKKK ALEFVDYINA KLPGLLELEY EGFYVRGFFV TKKKYALIDE EGKIITRGLE IVRRDWSEIA KETQAKVLEA ILKHGNVEEA VKIVKEVTEK LSKYEIPPEK LVIYEQITRP LHEYKAIGPH VAVAKRLAAR GVKVRPGMVI GYIVLRGDGP ISKRAILAEE FDLRKHKYDA EYYIENQVLP AVLRILEAFG YRKEDLRWQK TKQTGL |

Table of Sequences

| SEQ ID NO | Description | Sequence |
|---|---|---|
| 19 | K762Q variant of Deep Vent DNA polymerase catalytic domain amino acid sequence | SYAGGYV KEPEKGLWEG LVSLDFRSLY PSIIITHNVS PDTLNREGCR EYDVAPEVGH KFCKDFPGFI PSLLKRLLDE RQEIKRKMKA SKDPIEKKML DYRQRAIKIL ANSYYGYYGY AKARWYCKEC AESVTAWGRE YIEFVRKELE EKFGFKVLYI DTDGLYATIP GAKPEEIKKK ALEFVDYINA KLPGLLELEY EGFYVRGFFV TKKKYALIDE EGKIITRGLE IVRRDWSEIA KETQAKVLEA ILKHGNVEEA VKIVKEVTEK LSKYEIPPEK LVIYEQITRP LHEYKAIGPH VAVAKRLAAR GVKVRPGMVI GYIVLRGDGP ISKRAILAEE FDLRKHKYDA EYYIENQVLP AVLRILEAFG YRKEDLRWQK TQQTGL |
| 20 | Deep Vent DNA polymerase amino acid sequence with DNA binding domain | MILDADYITE DGKPIIRIFK KENGEFKVEY DRNFRPYIYA LLKDDSQIDE VRKITAERHG KIVRIIDAEK VRKKFLGRPI EVWRLYFEHP QDVPAIRDKI REHSAVIDIF EYDIPFAKRY LIDKGLIPME GDEELKLLAF DIETLYHEGE EFAKGPIIMI SYADEEEAKV ITWKKIDLPY VEVVSSEREM IKRFLKVIRE KDPDVIITYN GDSFDLPYLV KRAEKLGIKL PLGRDGSEPK MQRLGDMTAV EIKGRIHFDL YHVIRRTINL PTYTLEAVYE AIFGKPKEKV YAHEIAEAWE TGKGLERVAK YSMEDAKVTY ELGREFFPME AQLSRLVGQP LWDVSRSSTG NLVEWYLLRK AYERNELAPN KPDEREYERR LRESYAGGYV KEPEKGLWEG LVSLDFRSLY PSIIITHNVS PDTLNREGCR EYDVAPEVGH KFCKDFPGFI PSLLKRLLDE RQEIKRKMKA SKDPIEKKML DYRQRAIKIL ANSYYGYYGY AKARWYCKEC AESVTAWGRE YIEFVRKELE EKFGFKVLYI DTDGLYATIP GAKPEEIKKK ALEFVDYINA KLPGLLELEY EGFYVRGFFV TKKKYALIDE EGKIITRGLE IVRRDWSEIA KETQAKVLEA ILKHGNVEEA VKIVKEVTEK LSKYEIPPEK LVIYEQITRP LHEYKAIGPH VAVAKRLAAR GVKVRPGMVI GYIVLRGDGP ISKRAILAEE FDLRKHKYDA EYYIENQVLP AVLRILEAFG YRKEDLRWQK TKQTGLTAWL NIKKKGTGGG GATVKFKYKG EEKEVDISKI KKVWRVGKMI SFTYDEGGGK TGRGAVSEKD APKELLQMLE KQKK |
| 21 | K762Q variant of Deep Vent DNA polymerase amino acid sequence with DNA binding domain | MILDADYITE DGKPIIRIFK KENGEFKVEY DRNFRPYIYA LLKDDSQIDE VRKITAERHG KIVRIIDAEK VRKKFLGRPI EVWRLYFEHP QDVPAIRDKI REHSAVIDIF EYDIPFAKRY LIDKGLIPME GDEELKLLAF DIETLYHEGE EFAKGPIIMI SYADEEEAKV ITWKKIDLPY VEVVSSEREM IKRFLKVIRE KDPDVIITYN GDSFDLPYLV KRAEKLGIKL PLGRDGSEPK MQRLGDMTAV EIKGRIHFDL YHVIRRTINL PTYTLEAVYE AIFGKPKEKV YAHEIAEAWE TGKGLERVAK YSMEDAKVTY ELGREFFPME AQLSRLVGQP LWDVSRSSTG NLVEWYLLRK AYERNELAPN KPDEREYERR LRESYAGGYV KEPEKGLWEG LVSLDFRSLY PSIIITHNVS PDTLNREGCR EYDVAPEVGH KFCKDFPGFI PSLLKRLLDE RQEIKRKMKA SKDPIEKKML DYRQRAIKIL ANSYYGYYGY AKARWYCKEC AESVTAWGRE YIEFVRKELE EKFGFKVLYI DTDGLYATIP GAKPEEIKKK ALEFVDYINA KLPGLLELEY EGFYVRGFFV TKKKYALIDE EGKIITRGLE IVRRDWSEIA KETQAKVLEA ILKHGNVEEA VKIVKEVTEK LSKYEIPPEK LVIYEQITRP LHEYKAIGPH VAVAKRLAAR GVKVRPGMVI GYIVLRGDGP ISKRAILAEE FDLRKHKYDA EYYIENQVLP AVLRILEAFG YRKEDLRWQK TQQTGLTAWL NIKKKGTGGG GATVKFKYKG EEKEVDISKI KKVWRVGKMI SFTYDEGGGK TGRGAVSEKD APKELLQMLE KQKK |
| 22 | *Thermococcus litoralis* DNA polymerase | MILDTDYITK DGKPIIRIFK KENGEFKIEL DPHFQPYIYA LLKDDSAIEE IKAIKGERHG KTVRVLDAVK VRKKFLGREV EVWKLIFEHP QDVPAMRGKI REHPAVVDIY EYDIPFAKRY LIDKGLIPME GDEELKLLAF DIETFYHEGD EFGKGEIIMI SYADEEEARV ITWKNIDLPY VDVVSNEREM IKRFVQVVKE KDPDVIITYN GDNFDLPYLI KRAEKLGVRL VLGRDKEHPE PKIQRMGDSF AVEIKGRIHF DLFPVVRRTI NLPTYTLEAV YEAVLGKTKS KLGAEEIAAI WETEESMKKL AQYSMEDARA TYELGKEFFP MEAELAKLIG QSVWDVSRSS TGNLVEWYLL RVAYARNELA PNKPDEEEYK RRLRTTYLGG YVKEPEKGLW ENIIYLDFRS LYPSIIVTHN VSPDTLKEKG CKNYDVAPIV GYRFCKDFPG FIPSILGDLI AMRQDIKKKM KSTIDPIEKK MLDYRQRAIK LLANSYYGYM GYPKARWYSK ECAESVTAWG RHYIEMTIRE IEEKFGFKVL YADTGFYAT IPGEKPELIK KKAKEFLNYI NSKLPGLLEL EYEGFYLRGF FVTKKRYAVI |

Table of Sequences

| SEQ ID NO | Description | Sequence |
|---|---|---|
| | | DEEGRITTRG LEVVRRDWSE IAKETQAKVL EAILKEGSVE KAVEVVRDVV EKIAKYRVPL EKLVIHEQIT RDLKDYKAIG PHVAIAKRLA ARGIKVKPGT IISYIVLKGS GKISDRVILL TEYDPRKHKY DPDYYIENQV LPAVLRILEA FGYRKEDLRY QSSKQTGLDA WLKR |
| 23 | K764Q variant of *Thermococcus litoralis* DNA polymerase | MILDTDYITK DGKPIIRIFK KENGEFKIEL DPHFQPYIYA LLKDDSAIEE IKAIKGERHG KTVRVLDAVK VRKKFLGREV EVWKLIFEHP QDVPAMRGKI REHPAVVDIY EYDIPFAKRY LIDKGLIPME GDEELKLLAF DIETFYHEGD EFGKGEIIMI SYADEEEARV ITWKNIDLPY VDVVSNEREM IKRFVQVVKE KDPDVIITYN GDNFDLPYLI KRAEKLGVRL VLGRDKEHPE PKIQRMGDSF AVEIKGRIHF DLFPVVRRTI NLPTYTLEAV YEAVLGKTKS KLGAEEIAAI WETEESMKKL AQYSMEDARA TYELGKEFFP MEAELAKLIG QSVWDVSRSS TGNLVEWYLL RVAYARNELA PNKPDEEEYK RRLRTTYLGG YVKEPEKGLW ENIIYLDFRS LYPSIIVTHN VSPDTLEKEG CKNYDVAPIV GYRFCKDFPG FIPSILGDLI AMRQDIKKKM KSTIDPIEKK MLDYRQRAIK LLANSYYGYM GYPKARWYSK ECAESVTAWG RHYIEMTIRE IEEKFGFKVL YADTDGFYAT IPGEKPELIK KKAKEFLNYI NSKLPGLLEL EYEGFYLRGF FVTKKRYAVI DEEGRITTRG LEVVRRDWSE IAKETQAKVL EAILKEGSVE KAVEVVRDVV EKIAKYRVPL EKLVIHEQIT RDLKDYKAIG PHVAIAKRLA ARGIKVKPGT IISYIVLKGS GKISDRVILL TEYDPRKHKY DPDYYIENQV LPAVLRILEA FGYRKEDLRY QSSQQTGLDA WLKR |
| 24 | *Thermococcus litoralis* DNA polymerase catalytic domain amino acid sequence | TYLGG YVKEPEKGLW ENIIYLDFRS LYPSIIVTHN VSPDTLEKEG CKNYDVAPIV GYRFCKDFPG FIPSILGDLI AMRQDIKKKM KSTIDPIEKK MLDYRQRAIK LLANSYYGYM GYPKARWYSK ECAESVTAWG RHYIEMTIRE IEEKFGFKVL YADTDGFYAT IPGEKPELIK KKAKEFLNYI NSKLPGLLEL EYEGFYLRGF FVTKKRYAVI DEEGRITTRG LEVVRRDWSE IAKETQAKVL EAILKEGSVE KAVEVVRDVV EKIAKYRVPL EKLVIHEQIT RDLKDYKAIG PHVAIAKRLA ARGIKVKPGT IISYIVLKGS GKISDRVILL TEYDPRKHKY DPDYYIENQV LPAVLRILEA FGYRKEDLRY QSSKQTGL |
| 25 | K764Q variant of *Thermococcus litoralis* DNA polymerase catalytic domain amino acid sequence | TYLGG YVKEPEKGLW ENIIYLDFRS LYPSIIVTHN VSPDTLEKEG CKNYDVAPIV GYRFCKDFPG FIPSILGDLI AMRQDIKKKM KSTIDPIEKK MLDYRQRAIK LLANSYYGYM GYPKARWYSK ECAESVTAWG RHYIEMTIRE IEEKFGFKVL YADTDGFYAT IPGEKPELIK KKAKEFLNYI NSKLPGLLEL EYEGFYLRGF FVTKKRYAVI DEEGRITTRG LEVVRRDWSE IAKETQAKVL EAILKEGSVE KAVEVVRDVV EKIAKYRVPL EKLVIHEQIT RDLKDYKAIG PHVAIAKRLA ARGIKVKPGT IISYIVLKGS GKISDRVILL TEYDPRKHKY DPDYYIENQV LPAVLRILEA FGYRKEDLRY QSSQQTGL |
| 26 | *Thermococcus litoralis* DNA polymerase, sequence 2 (acc. ADK47977.1) | MILDTDYITK DGKPIIRIFK KENGEFKIEL DPHFQPYIYA LLKDDSAIEE IKAIKGERHG KSVRVVDAVK VKKKFLGREV EVWKLIFEHP QDVPAMRDKI KEHPAVIDIY EYDIPFAKRY LIDKGLIPME GDEELKLLAF DIETFYHEGD EFGKGEIIMI SYADEEEARV ITWKNIDLPY VDVVSNEREM IKRFVQVVKE KDPDVIITYN GDNFDLPYLI KRAEKLGVRL VLGRDKENPE PKIQRMGDSF AVEIKGRIHF DLFPVVRRTI NLPTYTLEAV YEAVLGKTKS KLGAEEIAAI WETEESMKKL AQYSMEDARA TYELGKEFFP MEAELAKLIG QSVWDVSRSS TGNLVEWYLL RVAYERNELA PNKPDEEEYK RRLRTTYLGG YVKEPEKGLW ENIIYLDFRS LYPSIIVTHN VSPDTLEKEG CENYDIAPIV SYRFCKDFPG FIPSILGDLI AMRQEIKKKM KATIDPVERK MLDYRQRAVK LLANSYYGYM GYPKARWYSK ECAESVTAWG RHYIEMTIKE IEEKFGFKVL YADTDGFYAT ISGEKPEIIK KKAREFLNYI NSKLPGLLEL EYEGFYLRGF FVTKKRYAVI DEEGRITTRG LEVVRRDWSE IAKETQAKVL EAILKDGSVE KAVEIVRDVL EKIAKYRVPL EKLVIHEQIT RDLKDYKAIG PHVAIAKRLA ARGIKVKPGT IISYIVLKGS GKISDRVILL TEYDPEKHKY DPDYYIENQV LPAVLRILEA FGYRKEDLRY QSSKQTGLDA WLKR |
| 27 | K764Q variant of *Thermococcus litoralis* DNA polymerase, sequence 2 (ace. ADK47977.1) | MILDTDYITK DGKPIIRIFK KENGEFKIEL DPHFQPYIYA LLKDDSAIEE IKAIKGERHG KSVRVVDAVK VKKKFLGREV EVWKLIFEHP QDVPAMRDKI KEHPAVIDIY EYDIPFAKRY |

| | Table of Sequences | |
|---|---|---|
| SEQ ID NO | Description | Sequence |
| | | LIDKGLIPME GDEELKLLAF DIETFYHEGD EFGKGEIIMI SYADEEEARV ITWKNIDLPY VDVVSNEREM IKRFVQVVKE KDPDVIITYN GDNFDLPYLI KRAEKLGVRL VLGRDKENPE PKIQRMGDSF AVEIKGRIHF DLFPVVRRTI NLPTYTLEAV YEAVLGKTKS KLGAEEIAAI WETEESMKKL AQYSMEDARA TYELGKEFFP MEAELAKLIG QSVWDVSRSS TGNLVEWYLL RVAYERNELA PNKPDEEEYK RRLRTTYLGG YVKEPEKGLW ENIIYLDFRS LYPSIIVTHN VSPDTLEKEG CENYDIAPIV SYRFCKDFPG FIPSILGDLI AMRQEIKKKM KATIDPVERK MLDYRQRAVK LLANSYYGYM GYPKARWYSK ECAESVTAWG RHYIEMTIKE IEEKFGFKVL YADTDGFYAT ISGEKPEIIK KKAREFLNYI NSKLPGLLEL EYEGFYLRGF FVTKKRYAVI DEEGRITTRG LEVVRRDWSE IAKETQAKVL EAILKDGSVE KAVEIVRDVL EKIAKYRVPL EKLVIHEQIT RDLKDYKAIG PHVAIAKRLA ARGIKVKPGT IISYIVLKGS GKISDRVILL TEYDPEKHKY DPDYYIENQV LPAVLRILEA FGYRKEDLRY QSSQQTGLDA WLKR |
| 28 | *Thermococcus litoralis* DNA polymerase, sequence 2 (acc. ADK47977.1), catalytic domain amino acid sequence | TYLGG YVKEPEKGLW ENIIYLDFRS LYPSIIVTHN VSPDTLEKEG CENYDIAPIV SYRFCKDFPG FIPSILGDLI AMRQEIKKKM KATIDPVERK MLDYRQRAVK LLANSYYGYM GYPKARWYSK ECAESVTAWG RHYIEMTIKE IEEKFGFKVL YADTDGFYAT ISGEKPEIIK KKAREFLNYI NSKLPGLLEL EYEGFYLRGF FVTKKRYAVI DEEGRITTRG LEVVRRDWSE IAKETQAKVL EAILKDGSVE KAVEIVRDVL EKIAKYRVPL EKLVIHEQIT RDLKDYKAIG PHVAIAKRLA ARGIKVKPGT IISYIVLKGS GKISDRVILL TEYDPEKHKY DPDYYIENQV LPAVLRILEA FGYRKEDLRY QSSKQTGL |
| 29 | K764Q variant of *Thermococcus litoralis* DNA polymerase, sequence 2 (acc. ADK47977.1), catalytic domain amino acid sequence | TYLGG YVKEPEKGLW ENIIYLDFRS LYPSIIVTHN VSPDTLEKEG CENYDIAPIV SYRFCKDFPG FIPSILGDLI AMRQEIKKKM KATIDPVERK MLDYRQRAVK LLANSYYGYM GYPKARWYSK ECAESVTAWG RHYIEMTIKE IEEKFGFKVL YADTDGFYAT ISGEKPEIIK KKAREFLNYI NSKLPGLLEL EYEGFYLRGF FVTKKRYAVI DEEGRITTRG LEVVRRDWSE IAKETQAKVL EAILKDGSVE KAVEIVRDVL EKIAKYRVPL EKLVIHEQIT RDLKDYKAIG PHVAIAKRLA ARGIKVKPGT IISYIVLKGS GKISDRVILL TEYDPEKHKY DPDYYIENQV LPAVLRILEA FGYRKEDLRY QSSQQTGL |
| 30 | *Thermococcus gorgonarius* DNA polymerase | MILDTDYITE DGKPVIRIFK KENGEFKIDY DRNFEPYIYA LLKDDSAIED VKKITAERHG TTVRVVRAEK VKKKFLGRPI EVWKLYFTHP QDVPAIRDKI KEHPAVVDIY EYDIPFAKRY LIDKGLIPME GDEELKMLAF DIETLYHEGE EFAEGPILMI SYADEEGARV ITWKNIDLPY VDVVSTEKEM IKRFLKVVKE KDPDVLITYN GDNFDFAYLK KRSEKLGVKF ILGREGSEPK IQRMGDRFAV EVKGRIHFDL YPVIRRTINL PTYTLEAVYE AIFGQPKEKV YAEEIAQAWE TGEGLERVAR YSMEDAKVTY ELGKEFFPME AQLSRLVGQS LWDVSRSSTG NLVEWFLLRK AYERNELAPN KPDERELARR RESYAGGYVK EPERGLWENI VYLDFRSLYP SIIITHNVSP DTLNREGCEE YDVAPQVGHK FCKDFPGFIP SLLGDLLEER QKVKKKMKAT IDPIEKKLLD YRQRAIKILA NSFYGYYGYA KARWYCKECA ESVTAWGRQY IETTIREIEE KFGFKVLYAD TDGFFATIPG ADAETVKKKA KEFLDYINAK LPGLLELEYE GFYKRGFFVT KKKYAVIDEE DKITTRGLEI VRRDWSEIAK ETQARVLEAI LKHGDVEEAV RIVKEVTEKL SKYEVPPEKL VIYEQITRDL KDYKATGPHV AVAKRLAARG IKIRPGTVIS YIVLKGSGRI GDRAIPFDEF DPAKHKYDAE YYIENQVLPA VERILRAFGY RKEDLRYQKT RQVGLGAWLK PKT |
| 31 | R761Q variant of *Thermococcus gorgonarius* DNA polymerase | MILDTDYITE DGKPVIRIFK KENGEFKIDY DRNFEPYIYA LLKDDSAIED VKKITAERHG TTVRVVRAEK VKKKFLGRPI EVWKLYFTHP QDVPAIRDKI KEHPAVVDIY EYDIPFAKRY LIDKGLIPME GDEELKMLAF DIETLYHEGE EFAEGPILMI SYADEEGARV ITWKNIDLPY VDVVSTEKEM IKRFLKVVKE KDPDVLITYN GDNFDFAYLK KRSEKLGVKF ILGREGSEPK IQRMGDRFAV EVKGRIHFDL YPVIRRTINL PTYTLEAVYE AIFGQPKEKV YAEEIAQAWE TGEGLERVAR YSMEDAKVTY ELGKEFFPME AQLSRLVGQS LWDVSRSSTG NLVEWFLLRK AYERNELAPN KPDERELARR RESYAGGYVK EPERGLWENI VYLDFRSLYP SIIITHNVSP DTLNREGCEE YDVAPQVGHK FCKDFPGFIP SLLGDLLEER QKVKKKMKAT IDPIEKKLLD |

Table of Sequences

| SEQ ID NO | Description | Sequence |
|---|---|---|
| | | YRQRAIKILA NSFYGYYGYA KARWYCKECA ESVTAWGRQY IETTIREIEE KFGFKVLYAD TDGFFATIPG ADAETVKKKA KEFLDYINAK LPGLLELEYE GFYKRGFFVT KKKYAVIDEE DKITTRGLEI VRRDWSEIAK ETQARVLEAI LKHGDVEEAV RIVKEVTEKL SKYEVPPEKL VIYEQITRDL KDYKATGPHV AVAKRLAARG IKIRPGTVIS YIVLKGSGRI GDRAIPFDEF DPAKHKYDAE YYIENQVLPA VERILRAFGY RKEDLRYQKT QQVGLGAWLK PKT |
| 32 | *Thermococcus gorgonarius* DNA polymerase, catalytic domain amino acid sequence | SYAGGYVK EPERGLWENI VYLDFRSLYP SIIITHNVSP DTLNREGCEE YDVAPQVGHK FCKDFPGFIP SLLGDLLEER QKVKKKMKAT IDPIEKKLLD YRQRAIKILA NSFYGYYGYA KARWYCKECA ESVTAWGRQY IETTIREIEE KFGFKVLYAD TDGFFATIPG ADAETVKKKA KEFLDYINAK LPGLLELEYE GFYKRGFFVT KKKYAVIDEE DKITTRGLEI VRRDWSEIAK ETQARVLEAI LKHGDVEEAV RIVKEVTEKL SKYEVPPEKL VIYEQITRDL KDYKATGPHV AVAKRLAARG IKIRPGTVIS YIVLKGSGRI GDRAIPFDEF DPAKHKYDAE YYIENQVLPA VERILRAFGY RKEDLRYQKT RQVGL |
| 33 | R761Q variant of *Thermococcus gorgonarius* DNA polymerase, catalytic domain amino acid sequence | SYAGGYVK EPERGLWENI VYLDFRSLYP SIIITHNVSP DTLNREGCEE YDVAPQVGHK FCKDFPGFIP SLLGDLLEER QKVKKKMKAT IDPIEKKLLD YRQRAIKILA NSFYGYYGYA KARWYCKECA ESVTAWGRQY IETTIREIEE KFGFKVLYAD TDGFFATIPG ADAETVKKKA KEFLDYINAK LPGLLELEYE GFYKRGFFVT KKKYAVIDEE DKITTRGLEI VRRDWSEIAK ETQARVLEAI LKHGDVEEAV RIVKEVTEKL SKYEVPPEKL VIYEQITRDL KDYKATGPHV AVAKRLAARG IKIRPGTVIS YIVLKGSGRI GDRAIPFDEF DPAKHKYDAE YYIENQVLPA VERILRAFGY RKEDLRYQKT QQVGL |
| 34 | *Thermococcus kodakarensis* DNA polymerase | MILDTDYITE DGKPVIRIFK KENGEFKIEY DRTFEPYFYA LLKDDSAIEE VKKITAERHG TVVTVKRVEK VQKKFLGRPV EVWKLYFTHP QDVPAIRDKI REHPAVIDIY EYDIPFAKRY LIDKGLVPME GDEELKMLAF DIETLYHEGE EFAEGPILMI SYADEEGARV ITWKNVDLPY VDVVSTEREM IKRFLRVVKE KDPDVLITYN GDNFDFAYLK KRCEKLGINF ALGRDGSEPK IQRMGDRFAV EVKGRIHFDL YPVIRRTINL PTYTLEAVYE AVFGQPKEKV YAEEITTAWE TGENLERVAR YSMEDAKVTY ELGKEFLPME AQLSRLIGQS LWDVSRSSTG NLVEWFLLRK AYERNELAPN KPDEKELARR RQSYEGGYVK EPERGLWENI VYLDFRSLYP SIIITHNVSP DTLNREGCKE YDVAPQVGHR FCKDFPGFIP SLLGDLLEER QKIKKKMKAT IDPIERKLLD YRQRAIKILA NSYYGYYGYA RARWYCKECA ESVTAWGREY ITMTIKEIEE KYGFKVIYSD TDGFFATIPG ADAETVKKKA MEFLKYINAK LPGALELEYE GFYKRGFFVT KKKYAVIDEE GKITTRGLEI VRRDWSEIAK ETQARVLEAL LKDGDVEKAV RIVKEVTEKL SKYEVPPEKL VIHEQITRDL KDYKATGPHV AVAKRLAARG VKIRPGTVIS YIVLKGSGRI GDRAIPFDEF DPTKHKYDAE YYIENQVLPA VERILRAFGY RKEDLRYQKT RQVGLSAWLK PKGT |
| 35 | R761Q variant of *Thermococcus kodakarensis* DNA polymerase | MILDTDYITE DGKPVIRIFK KENGEFKIEY DRTFEPYFYA LLKDDSAIEE VKKITAERHG TVVTVKRVEK VQKKFLGRPV EVWKLYFTHP QDVPAIRDKI REHPAVIDIY EYDIPFAKRY LIDKGLVPME GDEELKMLAF DIETLYHEGE EFAEGPILMI SYADEEGARV ITWKNVDLPY VDVVSTEREM IKRFLRVVKE KDPDVLITYN GDNFDFAYLK KRCEKLGINF ALGRDGSEPK IQRMGDRFAV EVKGRIHFDL YPVIRRTINL PTYTLEAVYE AVFGQPKEKV YAEEITTAWE TGENLERVAR YSMEDAKVTY ELGKEFLPME AQLSRLIGQS LWDVSRSSTG NLVEWFLLRK AYERNELAPN KPDEKELARR RQSYEGGYVK EPERGLWENI VYLDFRSLYP SIIITHNVSP DTLNREGCKE YDVAPQVGHR FCKDFPGFIP SLLGDLLEER QKIKKKMKAT IDPIERKLLD YRQRAIKILA NSYYGYYGYA RARWYCKECA ESVTAWGREY ITMTIKEIEE KYGFKVIYSD TDGFFATIPG ADAETVKKKA MEFLKYINAK LPGALELEYE GFYKRGFFVT KKKYAVIDEE GKITTRGLEI VRRDWSEIAK ETQARVLEAL LKDGDVEKAV RIVKEVTEKL SKYEVPPEKL VIHEQITRDL KDYKATGPHV AVAKRLAARG VKIRPGTVIS YIVLKGSGRI GDRAIPFDEF DPTKHKYDAE YYIENQVLPA VERILRAFGY RKEDLRYQKT QQVGLSAWLK PKGT |

| SEQ ID NO | Description | Sequence |
|---|---|---|
| 36 | *Thermococcus kodakarensis* DNA polymerase, catalytic domain amino acid sequence | SYEGGYVK EPERGLWENI VYLDFRSLYP SIIITHNVSP DTLNREGCKE YDVAPQVGHR FCKDFPGFIP SLLGDLLEER QKIKKKMKAT IDPIERKLLD YRQRAIKILA NSYYGYYGYA RARWYCKECA ESVTAWGREY ITMTIKEIEE KYGFKVIYSD TDGFFATIPG ADAETVKKKA MEFLKYINAK LPGALELEYE GFYKRGFFVT KKKYAVIDEE GKITTRGLEI VRRDWSEIAK ETQARVLEAL LKDGDVEKAV RIVKEVTEKL SKYEVPPEKL VIHEQITRDL KDYKATGPHV AVAKRLAARG VKIRPGTVIS YIVLKGSGRI GDRAIPFDEF DPTKHKYDAE YYIENQVLPA VERILRAFGY RKEDLRYQKT RQVGL |
| 37 | R761Q variant of *Thermococcus kodakarensis* DNA polymerase, catalytic domain amino acid sequence | SYEGGYVK EPERGLWENI VYLDFRSLYP SIIITHNVSP DTLNREGCKE YDVAPQVGHR FCKDFPGFIP SLLGDLLEER QKIKKKMKAT IDPIERKLLD YRQRAIKILA NSYYGYYGYA RARWYCKECA ESVTAWGREY ITMTIKEIEE KYGFKVIYSD TDGFFATIPG ADAETVKKKA MEFLKYINAK LPGALELEYE GFYKRGFFVT KKKYAVIDEE GKITTRGLEI VRRDWSEIAK ETQARVLEAL LKDGDVEKAV RIVKEVTEKL SKYEVPPEKL VIHEQITRDL KDYKATGPHV AVAKRLAARG VKIRPGTVIS YIVLKGSGRI GDRAIPFDEF DPTKHKYDAE YYIENQVLPA VERILRAFGY RKEDLRYQKT QQVGL |
| 38 | *Thermococcus* species 90 N-7 DNA polymerase, catalytic domain amino acid sequence | GYAGGYVK EPERGLWDNI VYLDFRSLYP SIIITHNVSP DTLNREGCKE YDVAPEVGHK FCKDFPGFIP SLLGDLLEER QKIKRKMKAT VDPLEKKLLD YRQRAIKILA NSFYGYYGYA KARWYCKECA ESVTAWGREY IEMVIRELEE KFGFKVLYAD TDGLHATIPG ADAETVKKKA KEFLKYINPK LPGLLELEYE GFYVRGFFVT KKKYAVIDEE GKITTRGLEI VRRDWSEIAK ETQARVLEAI LKHGDVEEAV RIVKEVTEKL SKYEVPPEKL VIHEQITRDL RDYKATGPHV AVAKRLAARG VKIRPGTVIS YIVLKGSGRI GDRAIPADEF DPTKHRYDAE YYIENQVLPA VERILKAFGY RKEDLRYQKT KQVGL |
| 39 | K761Q variant of *Thermococcus* species 90 N-7 DNA polymerase, catalytic domain amino acid sequence | GYAGGYVK EPERGLWDNI VYLDFRSLYP SIIITHNVSP DTLNREGCKE YDVAPEVGHK FCKDFPGFIP SLLGDLLEER QKIKRKMKAT VDPLEKKLLD YRQRAIKILA NSFYGYYGYA KARWYCKECA ESVTAWGREY IEMVIRELEE KFGFKVLYAD TDGLHATIPG ADAETVKKKA KEFLKYINPK LPGLLELEYE GFYVRGFFVT KKKYAVIDEE GKITTRGLEI VRRDWSEIAK ETQARVLEAI LKHGDVEEAV RIVKEVTEKL SKYEVPPEKL VIHEQITRDL RDYKATGPHV AVAKRLAARG VKIRPGTVIS YIVLKGSGRI GDRAIPADEF DPTKHRYDAE YYIENQVLPA VERILKAFGY RKEDLRYQKT QQVGL |
| 40 | *Thermococcus* species 90 N-7 DNA polymerase | MILDTDYITE NGKPVIRVFK KENGEFKIEY DRTFEPYFYA LLKDDSAIED VKKVTAKRHG TVVKVKRAEK VQKKFLGRPI EVWKLYFNHP QDVPAIRDRI RAHPAVVDIY EYDIPFAKRY LIDKGLIPME GDEELTMLAF DIETLYHEGE EFGTGPILMI SYADGSEARV ITWKKIDLPY VDVVSTEKEM IKRFLRVVRE KDPDVLITYN GDNFDFAYLK KRCEELGIKF TLGRDGSEPK IQRMGDRFAV EVKGRIHFDL YPVIRRTINL PTYTLEAVYE AVFGKPKEKV YAEEIAQAWE SGEGLERVAR YSMEDAKVTY ELGREFFPME AQLSRLIGQS LWDVSRSSTG NLVEWFLLRK AYKRNELAPN KPDERELARR RGGYAGGYVK EPERGLWDNI VYLDFRSLYP SIIITHNVSP DTLNREGCKE YDVAPEVGHK FCKDFPGFIP SLLGDLLEER QKIKRKMKAT VDPLEKKLLD YRQRAIKILA NSFYGYYGYA KARWYCKECA ESVTAWGREY IEMVIRELEE KFGFKVLYAD TDGLHATIPG ADAETVKKKA KEFLKYINPK LPGLLELEYE GFYVRGFFVT KKKYAVIDEE GKITTRGLEI VRRDWSEIAK ETQARVLEAI LKHGDVEEAV RIVKEVTEKL SKYEVPPEKL VIHEQITRDL RDYKATGPHV AVAKRLAARG VKIRPGTVIS YIVLKGSGRI GDRAIPADEF DPTKHRYDAE YYIENQVLPA VERILKAFGY RKEDLRYQKT KQVGLGAWLK VKGKK |
| 41 | K761Q variant of *Thermococcus* species 90 N-7 DNA polymerase | MILDTDYITE NGKPVIRVFK KENGEFKIEY DRTFEPYFYA LLKDDSAIED VKKVTAKRHG TVVKVKRAEK VQKKFLGRPI EVWKLYFNHP QDVPAIRDRI RAHPAVVDIY EYDIPFAKRY LIDKGLIPME GDEELTMLAF DIETLYHEGE EFGTGPILMI SYADGSEARV ITWKKIDLPY VDVVSTEKEM IKRFLRVVRE KDPDVLITYN GDNFDFAYLK KRCEELGIKF TLGRDGSEPK IQRMGDRFAV EVKGRIHFDL YPVIRRTINL PTYTLEAVYE AVFGKPKEKV YAEEIAQAWE SGEGLERVAR YSMEDAKVTY |

-continued

Table of Sequences

| SEQ ID NO | Description | Sequence |
|---|---|---|
| | | ELGREFFPME AQLSRLIGQS LWDVSRSSTG NLVEWFLLRK AYKRNELAPN KPDERELARR RGGYAGGYVK EPERGLWDNI VYLDFRSLYP SIIITHNVSP DTLNREGCKE YDVAPEVGHK FCKDFPGFIP SLLGDLLEER QKIKRKMKAT VDPLEKKLLD YRQRAIKILA NSFYGYYGYA KARWYCKECA ESVTAWGREY IEMVIRELEE KFGFKVLYAD TDGLHATIPG ADAETVKKKA KEFLKYINPK LPGLLELEYE GFYVRGFFVT KKKYAVIDEE GKITTRGLEI VRRDWSEIAK ETQARVLEAI LKHGDVEEAV RIVKEVTEKL SKYEVPPEKL VIHEQITRDL RDYKATGPHV AVAKRLAARG VKIRPGTVIS YIVLKGSGRI GDRAIPADEF DPTKHRYDAE YYIENQVLPA VERILKAFGY RKEDLRYQKT QQVGLGAWLK VKGKK |
| 42 | Sso7d SNS-dsDBD amino acid sequence of *Sulfolobus solfataricus* (see US 6,627,424) | ATVKFKYKGE EKEVDISKIK KVWRVGKMIS FTYDEGGGKT GRGAVSEKDA PKELLQMLEK QKK |
| 43 | Sac7d SNS-dsDBD amino acid sequence of *Sulfolobus acidocaldarius* | VKVKFKYKGE EKEVDTSKIK KVWRVGKMVS FTYDDNGKTG RGAVSEKDAP KELLDMLARA EREKK |
| 44 | *Pyrobaculum aerophilum* Pae3192 amino acid sequence | SKKQKLKFYD IKAKQAFETD QYEVIEKQTA RGPMMFAVAK SPYTGIKVYR LLGKKK |
| 45 | *Pyrobaculum aerophilum* Pae0384 amino acid sequence | AKQKLKFYDI KAKQSFETDK YEVIEKETAR GPMLFAVATS PYTGIKVYRL LGKKK |
| 46 | *Aeropyrum pernix* Ape3192 amino acid sequence | PKKEKIKFFD LVAKKYYETD NYEVEIKETK RGKFRFAKAK SPYTGKIFYR VLGKA |
| 47 | HmfA HMf family archaeal histone amino acid sequence of *Methanothermus fervidus* | GELPIAPIGR IIKNAGAERV SDDARIALAK VLEEMGEEIA SEAVKLAKHA GRKTIKAED |
| 48 | HMff1 HMf family archaeal histone amino acid sequence of *Methanothermus fervidus* | ELPIAPIGRI IKDAGAERVS DDARITLAKI LEEMGRDIAS EAIKLARHAG RKTIKAEDI |
| 49 | HpyA1 HMf family archaeal histone amino acid sequence of *Pyrococcus* strain GB-3a | GELPIAPVDR LIRKAGAERV SEEAAKILAE YLEEYAIEVS KKAVEFARHA GRKTVKAED |
| 50 | HpyA2 HMf family archaeal histone amino acid sequence of *Pyrococcus* strain GB-3a | AELPIAPVDR LIRKAGAQRV SEQAAKLLAE HLEEKALEIA RKAVDLAKHA GRKTVKAED |
| 51 | Sso7d sequence non-specific DNA-binding domain amino acid sequence | ATVKFKYKGE EKEVDISKIK KVWRVGKMIS FTYDEGGGKT GRGAVSEKDA PKELLQMLEK QK |
| 52 | *Pyrococcus* 3'-5' exonuclease domain amino acid sequence | EELKLLAFDI ETLYHEGEEF GKGPIIMISY ADEEEAKVIT WKKIDLPYVE VVSSEREMIK RFLKIIREKD PDIIITYNGD SFDLPYLAKR AEKLGIKLTI GRDGSEPKMQ RIGDMTAVEV KGRIHFDLYH VIRRTINLPT YTLEAVYEAI FGKPKEKVYA DEIAKAWETG EGLERVAKYS MEDAKATYEL GKEF TQSPASLAVS LGQRATISYR ASKSVSTSGY SYMHWNQQKP |
| 53 | 2A7 antibody light chain variable region | GQPPRLLIYL VSNLESGVPA RFSGSGSGTD FTLNIHPVEE EDAATYYCQH IRELTRSEGG PSW |
| 54 | 2A7 antibody heavy chain variable region | GPGLVAPSQS LSITCTVSGF SLTDYGVSWV RQSPGQGLEW LGIIWGDGST DYHSSLISRL RISKDNSKSQ VFLKLNSLQT DDTATYYCAR PVIGNYAMDY WGQG |
| 55 | 5D3 antibody light chain variable region | TQSPASLAVS LGQRATISCR ASESVEYYGT RLMQWYQQKP GKAPKLLIYG ASNVESGVPA RFSGSGSGTD FSLNIHPVEE DDFAMYFCQQ SRKVPWTFGG G |
| 56 | 5D3 antibody heavy chain variable region | SGPGLVAPSQ SLSITCTVSG FSLTDYGVSW VRQSPGQGLE WLGIIWGDGS TDYHSSLISR LRISKDNSKS QVFLKLNSLQ TDDTATYYCA RPVIGNYAMD YWGQG |

Table of Sequences

| SEQ ID NO | Description | Sequence |
|---|---|---|
| 57 | 2A7 antibody light chain CDR-L1 | RASKSVSTSGYSYMH |
| 58 | 2A7 antibody light chain CDR-L2 | LVSNLES |
| 59 | 2A7 antibody light chain CDR-L3 | QHIRELTRS |
| 60 | 2A7 antibody heavy chain CDR-H1 | FSLTDYGVS |
| 61 | 2A7 antibody heavy chain CDR-H2 | IIWGDGSTDYHSSLISRL |
| 62 | 2A7 antibody heavy chain CDR-H3 | PVIGNYAMDY |
| 63 | 5D3 antibody light chain CDR-L1 | RASESVEYYGTRLMQ |
| 64 | 5D3 antibody light chain CDR-L2 | GASNVEs |
| 65 | 5D3 antibody light chain CDR-L3 | QQSRKVPWT |
| 66 | 5D3 antibody heavy chain CDR-H1 | FSLTDYGVS |
| 67 | 5D3 antibody heavy chain CDR-H2 | IIWGDGSTDYHSSLISRL |
| 68 | 5D3 antibody heavy chain CDR-H3 | PVIGNYAMDY |

What is claimed is:

1. A monoclonal antibody that binds a protein comprising a DNA polymerase catalytic domain, wherein the antibody comprises:

a) a light chain comprising a CDR1 of SEQ ID NO: 57, a CDR2 of SEQ ID NO: 58, and a CDR3 of SEQ ID NO: 59, and a heavy chain comprising a CDR1 of SEQ ID NO: 60, a CDR2 of SEQ ID NO: 61, and a CDR3 of SEQ ID NO: 62; or b) a light chain comprising a CDR1 of SEQ ID NO: 63, a CDR2 of SEQ ID NO: 64, and a CDR3 of SEQ ID NO:65 and a heavy chain comprising a CDR1 of SEQ ID NO: 66, a CDR2 of SEQ ID NO: 67, and a CDR3 of SEQ ID NO: 68.

2. The monoclonal antibody of claim 1, wherein the antibody comprises:

a) a light chain variable region comprising the sequence of SEQ ID NO: 53 and a heavy chain variable region comprising the sequence of SEQ ID NO: 54; or b) a light chain variable region comprising the sequence of SEQ ID NO: 55 and a heavy chain variable region comprising the sequence of SEQ ID NO: 56.

3. The monoclonal antibody of claim 1, wherein the antibody is an antibody fragment.

4. The monoclonal antibody of claim 3, wherein the antibody fragment is selected from a Fab fragment, a Fab' fragment, a (Fab')2 fragment, an Fv fragment, and an scFv fragment.

5. The monoclonal antibody of claim 1, wherein the antibody is an IgG antibody.

6. The monoclonal antibody of claim 5, wherein the antibody is an IgG1, IgG2, IgG3, or IgG4 antibody.

7. A composition comprising at least one monoclonal antibody of claim 1 and a protein comprising a DNA polymerase catalytic domain to which said antibody of claim 1 binds.

8. The composition of claim 7, wherein the DNA polymerase catalytic domain is a thermophilic DNA polymerase catalytic domain.

9. The composition of claim 8, wherein the thermophilic DNA polymerase catalytic domain is a family B DNA polymerase catalytic domain.

10. The composition of claim 7, wherein the protein further comprises a 3' to 5' exonuclease domain.

11. The composition of claim 10, wherein the 3' to 5' exonuclease domain is N-terminal to the DNA polymerase catalytic domain.

12. The composition of claim 10, wherein the 3' to 5' exonuclease domain is a DEDDy archaeal exonuclease domain.

13. The composition of claim 10, wherein the 3' to 5' exonuclease domain comprises an amino acid sequence having at least 90%, 95%, 98%, 99%, or 100% identity to SEQ ID NO: 52.

14. The composition of claim 7, wherein the protein further comprises a sequence non-specific DNA-binding domain.

15. The composition of claim 14, wherein the sequence non-specific DNA-binding domain is C-terminal to the DNA polymerase catalytic domain.

16. The composition of claim 14, wherein the sequence non-specific DNA-binding domain is a 7 kD DNA-binding domain.

* * * * *

SEQUENCE LISTING

```
<160> NUMBER OF SEQ ID NOS: 72

<210> SEQ ID NO 1
<211> LENGTH: 775
<212> TYPE: PRT
<213> ORGANISM: Pyrococcus furiosus

<400> SEQUENCE: 1

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
        50                  55                  60

Ile Val Asp Val Glu Lys Val Glu Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
                100                 105                 110
```

-continued

```
Asp Ile Pro Phe Ala Lys Arg Tyr Leu Ile Asp Lys Gly Leu Ile Pro
            115                 120                 125
Met Glu Gly Glu Glu Leu Lys Ile Leu Ala Phe Asp Ile Glu Thr
    130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Val Ser Ser Glu Arg Glu Met Ile Lys
            180                 185                 190
Arg Phe Leu Arg Ile Ile Arg Glu Lys Asp Pro Asp Ile Ile Val Thr
        195                 200                 205
Tyr Asn Gly Asp Ser Phe Asp Phe Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Ser Gly Glu Asn
    290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Glu Tyr Gln Arg Arg Leu Arg Glu Ser
    370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
        435                 440                 445
Phe Ile Pro Ser Leu Leu Gly His Leu Leu Glu Glu Arg Gln Lys Ile
    450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
```

```
                530             535             540
Leu Tyr Ala Thr Ile Pro Gly Gly Glu Ser Glu Ile Lys Lys Lys
545                 550             555             560

Ala Leu Glu Phe Val Lys Tyr Ile Asn Ser Lys Leu Pro Gly Leu
                565             570             575

Glu Leu Glu Tyr Glu Gly Phe Tyr Arg Gly Phe Phe Val Thr Lys
                580             585             590

Lys Arg Tyr Ala Val Ile Asp Glu Glu Gly Lys Val Ile Thr Arg Gly
                595             600             605

Leu Glu Ile Val Arg Arg Asp Trp Ser Glu Ile Ala Lys Glu Thr Gln
                610             615             620

Ala Arg Val Leu Glu Thr Ile Leu Lys His Gly Asp Val Glu Glu Ala
625                 630             635             640

Val Arg Ile Val Lys Glu Val Ile Gln Lys Leu Ala Asn Tyr Glu Ile
                645             650             655

Pro Pro Glu Lys Leu Ala Ile Tyr Glu Gln Ile Thr Arg Pro Leu His
                660             665             670

Glu Tyr Lys Ala Ile Gly Pro His Val Ala Val Ala Lys Lys Leu Ala
                675             680             685

Ala Lys Gly Val Lys Ile Lys Pro Gly Met Val Ile Gly Tyr Ile Val
690                 695             700

Leu Arg Gly Asp Gly Pro Ile Ser Asn Arg Ala Ile Leu Ala Glu Glu
705                 710             715             720

Tyr Asp Pro Lys Lys His Lys Tyr Asp Ala Glu Tyr Tyr Ile Glu Asn
                725             730             735

Gln Val Leu Pro Ala Val Leu Arg Ile Leu Glu Gly Phe Gly Tyr Arg
                740             745             750

Lys Glu Asp Leu Arg Tyr Gln Lys Thr Arg Gln Val Gly Leu Thr Ser
                755             760             765

Trp Leu Asn Ile Lys Lys Ser
        770             775

<210> SEQ ID NO 2
<211> LENGTH: 775
<212> TYPE: PRT
<213> ORGANISM: Artificial sequence
<220> FEATURE:
<223> OTHER INFORMATION: Pfu GenBank WP_011011325.1 R762Q amino acid
      sequence

<400> SEQUENCE: 2

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
                35                  40                  45

Glu Glu Val Lys Lys Ile Thr Gly Glu Arg His Gly Lys Ile Val Arg
            50                  55                  60

Ile Val Asp Val Glu Lys Val Glu Lys Lys Phe Leu Gly Lys Pro Ile
65              70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
                100                 105                 110
```

```
Asp Ile Pro Phe Ala Lys Arg Tyr Leu Ile Asp Lys Gly Leu Ile Pro
            115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
    195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
    275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
    355                 360                 365

Pro Asn Lys Pro Ser Glu Glu Glu Tyr Gln Arg Arg Leu Arg Glu Ser
370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
    435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
    515                 520                 525

Leu Glu Glu Lys Phe Gly Phe Lys Val Leu Tyr Ile Asp Thr Asp Gly
```

Leu Tyr Ala Thr Ile Pro Gly Gly Glu Ser Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Tyr Gln Lys Thr Gln Gln Val Gly Leu Thr Ser
            755                 760                 765

Trp Leu Asn Ile Lys Lys Ser
        770                 775

<210> SEQ ID NO 3
<211> LENGTH: 775
<212> TYPE: PRT
<213> ORGANISM: Artificial sequence
<220> FEATURE:
<223> OTHER INFORMATION: Pfu GenBank WP_011011325.1 A408S R762Q amino
      acid sequence

<400> SEQUENCE: 3

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
                100                 105                 110

-continued

```
Asp Ile Pro Phe Ala Lys Arg Tyr Leu Ile Asp Lys Gly Leu Ile Pro
            115                 120                 125
Met Glu Gly Glu Glu Leu Lys Ile Leu Ala Phe Asp Ile Glu Thr
    130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Val Ser Ser Arg Glu Met Ile Lys
            180                 185                 190
Arg Phe Leu Arg Ile Ile Arg Glu Lys Asp Pro Asp Ile Ile Val Thr
    195                 200                 205
Tyr Asn Gly Asp Ser Phe Asp Phe Pro Tyr Leu Ala Lys Arg Ala Glu
210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
            245                 250                 255
His Phe Asp Leu Tyr His Val Ile Thr Arg Thr Ile Asn Leu Pro Thr
    260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Ser Gly Glu Asn
            290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
            325                 330                 335
Val Gly Gln Pro Leu Trp Asp Val Ser Arg Ser Ser Thr Gly Asn Leu
        340                 345                 350
Val Glu Trp Phe Leu Leu Arg Lys Ala Tyr Glu Arg Asn Glu Val Ala
    355                 360                 365
Pro Asn Lys Pro Ser Glu Glu Glu Tyr Gln Arg Arg Leu Arg Glu Ser
370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ser Leu Tyr Pro Ser Ile Ile Ile Thr
            405                 410                 415
His Asn Val Ser Pro Asp Thr Leu Asn Leu Glu Gly Cys Lys Asn Tyr
        420                 425                 430
Asp Ile Ala Pro Gln Val Gly His Lys Phe Cys Lys Asp Ile Pro Gly
    435                 440                 445
Phe Ile Pro Ser Leu Leu Gly His Leu Leu Glu Glu Arg Gln Lys Ile
    450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
            485                 490                 495
Tyr Tyr Gly Tyr Ala Lys Ala Arg Trp Tyr Cys Lys Glu Cys Ala Glu
        500                 505                 510
Ser Val Thr Ala Trp Gly Arg Lys Tyr Ile Glu Leu Val Trp Lys Glu
    515                 520                 525
Leu Glu Glu Lys Phe Gly Phe Lys Val Leu Tyr Ile Asp Thr Asp Gly
```

-continued

```
                530                 535                 540
Leu Tyr Ala Thr Ile Pro Gly Gly Glu Ser Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
                580                 585                 590

Lys Arg Tyr Ala Val Ile Asp Glu Glu Gly Lys Val Ile Thr Arg Gly
                595                 600                 605

Leu Glu Ile Val Arg Arg Asp Trp Ser Glu Ile Ala Lys Glu Thr Gln
                610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
                675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Tyr Gln Lys Thr Gln Gln Val Gly Leu Thr Ser
                755                 760                 765

Trp Leu Asn Ile Lys Lys Ser
                770                 775

<210> SEQ ID NO 4
<211> LENGTH: 383
<212> TYPE: PRT
<213> ORGANISM: Artificial sequence
<220> FEATURE:
<223> OTHER INFORMATION: Pfu DNA polymerase (GenBank Acc. No.
      WP_011011325.1), catalytic domain amino acid sequence

<400> SEQUENCE: 4

Ser Tyr Thr Gly Gly Phe Val Lys Glu Pro Glu Lys Gly Leu Trp Glu
1               5                   10                  15

Asn Ile Val Tyr Leu Asp Phe Arg Ala Leu Tyr Pro Ser Ile Ile Ile
                20                  25                  30

Thr His Asn Val Ser Pro Asp Thr Leu Asn Leu Glu Gly Cys Lys Asn
                35                  40                  45

Tyr Asp Ile Ala Pro Gln Val Gly His Lys Phe Cys Lys Asp Ile Pro
                50                  55                  60

Gly Phe Ile Pro Ser Leu Leu Gly His Leu Leu Glu Glu Arg Gln Lys
65                  70                  75                  80

Ile Lys Thr Lys Met Lys Glu Thr Gln Asp Pro Ile Glu Lys Ile Leu
                85                  90                  95

Leu Asp Tyr Arg Gln Lys Ala Ile Lys Leu Leu Ala Asn Ser Phe Tyr
                100                 105                 110
```

```
Gly Tyr Tyr Gly Tyr Ala Lys Ala Arg Trp Tyr Cys Lys Glu Cys Ala
            115                 120                 125

Glu Ser Val Thr Ala Trp Gly Arg Lys Tyr Ile Glu Leu Val Trp Lys
    130                 135                 140

Glu Leu Glu Glu Lys Phe Gly Phe Lys Val Leu Tyr Ile Asp Thr Asp
145                 150                 155                 160

Gly Leu Tyr Ala Thr Ile Pro Gly Gly Glu Ser Glu Ile Lys Lys
                165                 170                 175

Lys Ala Leu Glu Phe Val Lys Tyr Ile Asn Ser Lys Leu Pro Gly Leu
                180                 185                 190

Leu Glu Leu Glu Tyr Glu Gly Phe Tyr Lys Arg Gly Phe Phe Val Thr
        195                 200                 205

Lys Lys Arg Tyr Ala Val Ile Asp Glu Glu Gly Lys Val Ile Thr Arg
    210                 215                 220

Gly Leu Glu Ile Val Arg Arg Asp Trp Ser Glu Ile Ala Lys Glu Thr
225                 230                 235                 240

Gln Ala Arg Val Leu Glu Thr Ile Leu Lys His Gly Asp Val Glu Glu
                245                 250                 255

Ala Val Arg Ile Val Lys Glu Val Ile Gln Lys Leu Ala Asn Tyr Glu
            260                 265                 270

Ile Pro Pro Glu Lys Leu Ala Ile Tyr Glu Gln Ile Thr Arg Pro Leu
        275                 280                 285

His Glu Tyr Lys Ala Ile Gly Pro His Val Ala Val Ala Lys Lys Leu
    290                 295                 300

Ala Ala Lys Gly Val Lys Ile Lys Pro Gly Met Val Ile Gly Tyr Ile
305                 310                 315                 320

Val Leu Arg Gly Asp Gly Pro Ile Ser Asn Arg Ala Ile Leu Ala Glu
                325                 330                 335

Glu Tyr Asp Pro Lys Lys His Lys Tyr Asp Ala Glu Tyr Tyr Ile Glu
            340                 345                 350

Asn Gln Val Leu Pro Ala Val Leu Arg Ile Leu Glu Gly Phe Gly Tyr
        355                 360                 365

Arg Lys Glu Asp Leu Arg Tyr Gln Lys Thr Arg Gln Val Gly Leu
    370                 375                 380

<210> SEQ ID NO 5
<211> LENGTH: 383
<212> TYPE: PRT
<213> ORGANISM: Artificial sequence
<220> FEATURE:
<223> OTHER INFORMATION: Pfu DNA polymerase (GenBank Acc. No.
      WP_011011325.1) catalytic domain R762Q amino acid sequence

<400> SEQUENCE: 5

Ser Tyr Thr Gly Gly Phe Val Lys Glu Pro Glu Lys Gly Leu Trp Glu
1               5                   10                  15

Asn Ile Val Tyr Leu Asp Phe Arg Ala Leu Tyr Pro Ser Ile Ile Ile
            20                  25                  30

Thr His Asn Val Ser Pro Asp Thr Leu Asn Leu Glu Gly Cys Lys Asn
        35                  40                  45

Tyr Asp Ile Ala Pro Gln Val Gly His Lys Phe Cys Lys Asp Ile Pro
    50                  55                  60

Gly Phe Ile Pro Ser Leu Leu Gly His Leu Leu Glu Glu Arg Gln Lys
65                  70                  75                  80

Ile Lys Thr Lys Met Lys Glu Thr Gln Asp Pro Ile Glu Lys Ile Leu
                85                  90                  95
```

Leu Asp Tyr Arg Gln Lys Ala Ile Lys Leu Leu Ala Asn Ser Phe Tyr
                100                 105                 110

Gly Tyr Tyr Gly Tyr Ala Lys Ala Arg Trp Tyr Cys Lys Glu Cys Ala
            115                 120                 125

Glu Ser Val Thr Ala Trp Gly Arg Lys Tyr Ile Glu Leu Val Trp Lys
130                 135                 140

Glu Leu Glu Glu Lys Phe Gly Phe Lys Val Leu Tyr Ile Asp Thr Asp
145                 150                 155                 160

Gly Leu Tyr Ala Thr Ile Pro Gly Gly Glu Ser Glu Ile Lys Lys
                165                 170                 175

Lys Ala Leu Glu Phe Val Lys Tyr Ile Asn Ser Lys Leu Pro Gly Leu
            180                 185                 190

Leu Glu Leu Glu Tyr Glu Gly Phe Tyr Lys Arg Gly Phe Phe Val Thr
                195                 200                 205

Lys Lys Arg Tyr Ala Val Ile Asp Glu Glu Gly Lys Val Ile Thr Arg
210                 215                 220

Gly Leu Glu Ile Val Arg Arg Asp Trp Ser Glu Ile Ala Lys Glu Thr
225                 230                 235                 240

Gln Ala Arg Val Leu Glu Thr Ile Leu Lys His Gly Asp Val Glu Glu
                245                 250                 255

Ala Val Arg Ile Val Lys Glu Val Ile Gln Lys Leu Ala Asn Tyr Glu
            260                 265                 270

Ile Pro Pro Glu Lys Leu Ala Ile Tyr Glu Gln Ile Thr Arg Pro Leu
                275                 280                 285

His Glu Tyr Lys Ala Ile Gly Pro His Val Ala Val Ala Lys Lys Leu
            290                 295                 300

Ala Ala Lys Gly Val Lys Ile Lys Pro Gly Met Val Ile Gly Tyr Ile
305                 310                 315                 320

Val Leu Arg Gly Asp Gly Pro Ile Ser Asn Arg Ala Ile Leu Ala Glu
                325                 330                 335

Glu Tyr Asp Pro Lys Lys His Lys Tyr Asp Ala Glu Tyr Tyr Ile Glu
            340                 345                 350

Asn Gln Val Leu Pro Ala Val Leu Arg Ile Leu Glu Gly Phe Gly Tyr
                355                 360                 365

Arg Lys Glu Asp Leu Arg Tyr Gln Lys Thr Gln Gln Val Gly Leu
            370                 375                 380

<210> SEQ ID NO 6
<211> LENGTH: 383
<212> TYPE: PRT
<213> ORGANISM: Artificial sequence
<220> FEATURE:
<223> OTHER INFORMATION: Pfu DNA polymerase (GenBank Acc. No.
      WP_011011325.1) catalytic domain A408S R762Q amino acid sequence

<400> SEQUENCE: 6

Ser Tyr Thr Gly Gly Phe Val Lys Glu Pro Glu Lys Gly Leu Trp Glu
1               5                   10                  15

Asn Ile Val Tyr Leu Asp Phe Arg Ser Leu Tyr Pro Ser Ile Ile Ile
            20                  25                  30

Thr His Asn Val Ser Pro Asp Thr Leu Asn Leu Glu Gly Cys Lys Asn
        35                  40                  45

Tyr Asp Ile Ala Pro Gln Val Gly His Lys Phe Cys Lys Asp Ile Pro
    50                  55                  60

Gly Phe Ile Pro Ser Leu Leu Gly His Leu Leu Glu Glu Arg Gln Lys

```
                65                  70                  75                  80
        Ile Lys Thr Lys Met Lys Glu Thr Gln Asp Pro Ile Glu Lys Ile Leu
                        85                  90                  95

Leu Asp Tyr Arg Gln Lys Ala Ile Lys Leu Ala Asn Ser Phe Tyr
                       100                 105                 110

Gly Tyr Tyr Gly Tyr Ala Lys Ala Arg Trp Tyr Cys Lys Glu Cys Ala
                       115                 120                 125

Glu Ser Val Thr Ala Trp Gly Arg Lys Tyr Ile Glu Leu Val Trp Lys
                130                 135                 140

Glu Leu Glu Glu Lys Phe Gly Phe Lys Val Leu Tyr Ile Asp Thr Asp
        145                 150                 155                 160

Gly Leu Tyr Ala Thr Ile Pro Gly Gly Glu Ser Glu Ile Lys Lys
                        165                 170                 175

Lys Ala Leu Glu Phe Val Lys Tyr Ile Asn Ser Lys Leu Pro Gly Leu
                        180                 185                 190

Leu Glu Leu Glu Tyr Glu Gly Phe Tyr Lys Arg Gly Phe Phe Val Thr
                        195                 200                 205

Lys Lys Arg Tyr Ala Val Ile Asp Glu Glu Gly Lys Val Ile Thr Arg
                210                 215                 220

Gly Leu Glu Ile Val Arg Arg Asp Trp Ser Glu Ile Ala Lys Glu Thr
        225                 230                 235                 240

Gln Ala Arg Val Leu Glu Thr Ile Leu Lys His Gly Asp Val Glu Glu
                        245                 250                 255

Ala Val Arg Ile Val Lys Glu Val Ile Gln Lys Leu Ala Asn Tyr Glu
                        260                 265                 270

Ile Pro Pro Glu Lys Leu Ala Ile Tyr Glu Gln Ile Thr Arg Pro Leu
                        275                 280                 285

His Glu Tyr Lys Ala Ile Gly Pro His Val Ala Val Ala Lys Lys Leu
                        290                 295                 300

Ala Ala Lys Gly Val Lys Ile Lys Pro Gly Met Val Ile Gly Tyr Ile
        305                 310                 315                 320

Val Leu Arg Gly Asp Gly Pro Ile Ser Asn Arg Ala Ile Leu Ala Glu
                        325                 330                 335

Glu Tyr Asp Pro Lys Lys His Lys Tyr Asp Ala Glu Tyr Tyr Ile Glu
                        340                 345                 350

Asn Gln Val Leu Pro Ala Val Leu Arg Ile Leu Glu Gly Phe Gly Tyr
                        355                 360                 365

Arg Lys Glu Asp Leu Arg Tyr Gln Lys Thr Gln Gln Val Gly Leu
                370                 375                 380

<210> SEQ ID NO 7
<211> LENGTH: 844
<212> TYPE: PRT
<213> ORGANISM: Artificial sequence
<220> FEATURE:
<223> OTHER INFORMATION: Pfu GenBank WP_011011325.1 with DNA binding
      domain amino acid sequence

<400> SEQUENCE: 7

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
                35                  40                  45
```

-continued

Glu Glu Val Lys Lys Ile Thr Gly Glu Arg His Gly Lys Ile Val Arg
          50                  55                  60

Ile Val Asp Val Glu Lys Val Glu Lys Phe Leu Gly Lys Pro Ile
65                  70                  75                  80

Thr Val Trp Lys Leu Tyr Leu Glu His Pro Gln Asp Val Pro Thr Ile
              85                  90                  95

Arg Glu Lys Val Arg Glu His Pro Ala Val Val Asp Ile Phe Glu Tyr
              100                 105                 110

Asp Ile Pro Phe Ala Lys Arg Tyr Leu Ile Asp Lys Gly Leu Ile Pro
              115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
              165                 170                 175

Asp Leu Pro Tyr Val Glu Val Val Ser Ser Glu Arg Glu Met Ile Lys
              180                 185                 190

Arg Phe Leu Arg Ile Ile Arg Glu Lys Asp Pro Asp Ile Ile Val Thr
    195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
              245                 250                 255

His Phe Asp Leu Tyr His Val Ile Thr Arg Thr Ile Asn Leu Pro Thr
              260                 265                 270

Tyr Thr Leu Glu Ala Val Tyr Glu Ala Ile Phe Gly Lys Pro Lys Glu
    275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
              325                 330                 335

Val Gly Gln Pro Leu Trp Asp Val Ser Arg Ser Ser Thr Gly Asn Leu
    340                 345                 350

Val Glu Trp Phe Leu Leu Arg Lys Ala Tyr Glu Arg Asn Glu Val Ala
    355                 360                 365

Pro Asn Lys Pro Ser Glu Glu Glu Tyr Gln Arg Arg Leu Arg Glu Ser
370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
              405                 410                 415

His Asn Val Ser Pro Asp Thr Leu Asn Leu Glu Gly Cys Lys Asn Tyr
              420                 425                 430

Asp Ile Ala Pro Gln Val Gly His Lys Phe Cys Lys Asp Ile Pro Gly
              435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu

```
            465                 470                 475                 480

Asp Tyr Arg Gln Lys Ala Ile Lys Leu Leu Ala Asn Ser Phe Tyr Gly
                    485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Glu Ser Glu Ile Lys Lys
545                 550                 555                 560

Ala Leu Glu Phe Val Lys Tyr Ile Asn Ser Lys Leu Pro Gly Leu Leu
                    565                 570                 575

Glu Leu Glu Tyr Glu Gly Phe Tyr Lys Arg Gly Phe Phe Val Thr Lys
                580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
        610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                    645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                    725                 730                 735

Gln Val Leu Pro Ala Val Leu Arg Ile Leu Glu Gly Phe Gly Tyr Arg
                740                 745                 750

Lys Glu Asp Leu Arg Tyr Gln Lys Thr Arg Gln Val Gly Leu Thr Ser
            755                 760                 765

Trp Leu Asn Ile Lys Lys Ser Gly Thr Gly Gly Gly Ala Thr Val
        770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                    805                 810                 815

Gly Gly Gly Lys Thr Gly Arg Gly Ala Val Ser Glu Lys Asp Ala Pro
                820                 825                 830

Lys Glu Leu Leu Gln Met Leu Glu Lys Gln Lys Lys
            835                 840

<210> SEQ ID NO 8
<211> LENGTH: 844
<212> TYPE: PRT
<213> ORGANISM: Artificial sequence
<220> FEATURE:
<223> OTHER INFORMATION: Pfu GenBank WP_011011325.1 R762Q with DNA
      binding domain amino acid sequence
```

<400> SEQUENCE: 8

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
```

-continued

```
            405                 410                 415
His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
            450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                    485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                    565                 570                 575

Glu Leu Glu Tyr Glu Gly Phe Tyr Lys Arg Gly Phe Phe Val Thr Lys
                580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                    645                 650                 655

Pro Pro Glu Lys Leu Ala Ile Tyr Glu Gln Ile Thr Arg Pro Leu His
                    660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                    725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Gln Gln Val Gly Leu Thr Ser
                755                 760                 765

Trp Leu Asn Ile Lys Lys Ser Gly Thr Gly Gly Gly Ala Thr Val
            770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                    805                 810                 815

Gly Gly Gly Lys Thr Gly Arg Gly Ala Val Ser Glu Lys Asp Ala Pro
            820                 825                 830
```

<210> SEQ ID NO 9
<211> LENGTH: 844
<212> TYPE: PRT
<213> ORGANISM: Artificial sequence
<220> FEATURE:
<223> OTHER INFORMATION: Pfu GenBank WP_011011325.1 A408S R762Q with
      DNA binding domain amino acid sequence

<400> SEQUENCE: 9

```
Lys Glu Leu Leu Gln Met Leu Glu Lys Gln Lys Lys
        835                 840

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
```

-continued

```
                340                 345                 350
Val Glu Trp Phe Leu Leu Arg Lys Ala Tyr Glu Arg Asn Glu Val Ala
            355                 360                 365

Pro Asn Lys Pro Ser Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ser Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Gln Gln Val Gly Leu Thr Ser
            755                 760                 765
```

```
Trp Leu Asn Ile Lys Lys Ser Gly Thr Gly Gly Gly Ala Thr Val
        770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
                820                 825                 830

Lys Glu Leu Leu Gln Met Leu Glu Lys Gln Lys Lys
                835                 840

<210> SEQ ID NO 10
<211> LENGTH: 383
<212> TYPE: PRT
<213> ORGANISM: Artificial sequence
<220> FEATURE:
<223> OTHER INFORMATION: Pyrococcus catalytic domain amino acid sequence

<400> SEQUENCE: 10

Ser Tyr Ala Gly Gly Phe Val Lys Glu Pro Glu Lys Gly Leu Trp Glu
1               5                   10                  15

Asn Ile Val Ser Leu Asp Phe Arg Ala Leu Tyr Pro Ser Ile Ile Ile
                20                  25                  30

Thr His Asn Val Ser Pro Asp Thr Leu Asn Arg Glu Gly Cys Arg Asn
            35                  40                  45

Tyr Asp Val Ala Pro Glu Val Gly His Lys Phe Cys Lys Asp Phe Pro
    50                  55                  60

Gly Phe Ile Pro Ser Leu Leu Lys Arg Leu Leu Asp Glu Arg Gln Lys
65                  70                  75                  80

Ile Lys Thr Lys Met Lys Ala Ser Gln Asp Pro Ile Glu Lys Ile Met
                85                  90                  95

Leu Asp Tyr Arg Gln Arg Ala Ile Lys Ile Leu Ala Asn Ser Tyr Tyr
            100                 105                 110

Gly Tyr Tyr Gly Tyr Ala Lys Ala Arg Trp Tyr Cys Lys Glu Cys Ala
        115                 120                 125

Glu Ser Val Thr Ala Trp Gly Arg Glu Tyr Ile Glu Phe Val Trp Lys
130                 135                 140

Glu Leu Glu Glu Lys Phe Gly Phe Lys Val Leu Tyr Ile Asp Thr Asp
145                 150                 155                 160

Gly Leu Tyr Ala Thr Ile Pro Gly Gly Lys Ser Glu Glu Ile Lys Lys
                165                 170                 175

Lys Ala Leu Glu Phe Val Asp Tyr Ile Asn Ala Lys Leu Pro Gly Leu
            180                 185                 190

Leu Glu Leu Glu Tyr Glu Gly Phe Tyr Lys Arg Gly Phe Phe Val Thr
        195                 200                 205

Lys Lys Lys Tyr Ala Leu Ile Asp Glu Glu Gly Lys Ile Ile Thr Arg
    210                 215                 220

Gly Leu Glu Ile Val Arg Arg Asp Trp Ser Glu Ile Ala Lys Glu Thr
225                 230                 235                 240

Gln Ala Arg Val Leu Glu Ala Ile Leu Lys His Gly Asn Val Glu Glu
                245                 250                 255

Ala Val Arg Ile Val Lys Glu Val Thr Gln Lys Leu Ser Lys Tyr Glu
            260                 265                 270

Ile Pro Pro Glu Lys Leu Ala Ile Tyr Glu Gln Ile Thr Arg Pro Leu
        275                 280                 285
```

```
His Glu Tyr Lys Ala Ile Gly Pro His Val Ala Val Ala Lys Arg Leu
        290                 295                 300

Ala Ala Lys Gly Val Lys Ile Lys Pro Gly Met Val Ile Gly Tyr Ile
305                 310                 315                 320

Val Leu Arg Gly Asp Gly Pro Ile Ser Asn Arg Ala Ile Leu Ala Glu
                325                 330                 335

Glu Tyr Asp Pro Arg Lys His Lys Tyr Asp Ala Glu Tyr Tyr Ile Glu
                340                 345                 350

Asn Gln Val Leu Pro Ala Val Leu Arg Ile Leu Glu Gly Phe Gly Tyr
            355                 360                 365

Arg Lys Glu Asp Leu Arg Trp Gln Lys Thr Lys Gln Thr Gly Leu
370                 375                 380
```

<210> SEQ ID NO 11
<211> LENGTH: 383
<212> TYPE: PRT
<213> ORGANISM: Artificial sequence
<220> FEATURE:
<223> OTHER INFORMATION: Pyrococcus K762Q catalytic domain amino acid
      sequence

<400> SEQUENCE: 11

```
Ser Tyr Ala Gly Gly Phe Val Lys Glu Pro Glu Lys Gly Leu Trp Glu
1               5                   10                  15

Asn Ile Val Ser Leu Asp Phe Arg Ala Leu Tyr Pro Ser Ile Ile Ile
            20                  25                  30

Thr His Asn Val Ser Pro Asp Thr Leu Asn Arg Glu Gly Cys Arg Asn
        35                  40                  45

Tyr Asp Val Ala Pro Glu Val Gly His Lys Phe Cys Lys Asp Phe Pro
    50                  55                  60

Gly Phe Ile Pro Ser Leu Leu Lys Arg Leu Leu Asp Glu Arg Gln Lys
65                  70                  75                  80

Ile Lys Thr Lys Met Lys Ala Ser Gln Asp Pro Ile Glu Lys Ile Met
                85                  90                  95

Leu Asp Tyr Arg Gln Arg Ala Ile Lys Ile Leu Ala Asn Ser Tyr Tyr
            100                 105                 110

Gly Tyr Tyr Gly Tyr Ala Lys Ala Arg Trp Tyr Cys Lys Glu Cys Ala
        115                 120                 125

Glu Ser Val Thr Ala Trp Gly Arg Glu Tyr Ile Glu Phe Val Trp Lys
130                 135                 140

Glu Leu Glu Glu Lys Phe Gly Phe Lys Val Leu Tyr Ile Asp Thr Asp
145                 150                 155                 160

Gly Leu Tyr Ala Thr Ile Pro Gly Gly Lys Ser Glu Glu Ile Lys Lys
                165                 170                 175

Lys Ala Leu Glu Phe Val Asp Tyr Ile Asn Ala Lys Leu Pro Gly Leu
            180                 185                 190

Leu Glu Leu Glu Tyr Glu Gly Phe Tyr Lys Arg Gly Phe Phe Val Thr
        195                 200                 205

Lys Lys Lys Tyr Ala Leu Ile Asp Glu Glu Gly Lys Ile Ile Thr Arg
    210                 215                 220

Gly Leu Glu Ile Val Arg Arg Asp Trp Ser Glu Ile Ala Lys Glu Thr
225                 230                 235                 240

Gln Ala Arg Val Leu Glu Ala Ile Leu Lys His Gly Asn Val Glu Glu
                245                 250                 255

Ala Val Arg Ile Val Lys Glu Val Thr Gln Lys Leu Ser Lys Tyr Glu
```

```
            260                 265                 270
Ile Pro Pro Glu Lys Leu Ala Ile Tyr Glu Gln Ile Thr Arg Pro Leu
            275                 280                 285

His Glu Tyr Lys Ala Ile Gly Pro His Val Ala Val Ala Lys Arg Leu
        290                 295                 300

Ala Ala Lys Gly Val Lys Ile Lys Pro Gly Met Val Ile Gly Tyr Ile
305                 310                 315                 320

Val Leu Arg Gly Asp Gly Pro Ile Ser Asn Arg Ala Ile Leu Ala Glu
                325                 330                 335

Glu Tyr Asp Pro Arg Lys His Lys Tyr Asp Ala Glu Tyr Tyr Ile Glu
            340                 345                 350

Asn Gln Val Leu Pro Ala Val Leu Arg Ile Leu Glu Gly Phe Gly Tyr
        355                 360                 365

Arg Lys Glu Asp Leu Arg Trp Gln Lys Thr Gln Thr Gly Leu
    370                 375                 380

<210> SEQ ID NO 12
<211> LENGTH: 383
<212> TYPE: PRT
<213> ORGANISM: Artificial sequence
<220> FEATURE:
<223> OTHER INFORMATION: Pyrococcus A408S K762Q catalytic domain amino
      acid sequence

<400> SEQUENCE: 12

Ser Tyr Ala Gly Gly Phe Val Lys Glu Pro Glu Lys Gly Leu Trp Glu
1               5                   10                  15

Asn Ile Val Ser Leu Asp Phe Arg Ser Leu Tyr Pro Ser Ile Ile Ile
            20                  25                  30

Thr His Asn Val Ser Pro Asp Thr Leu Asn Arg Glu Gly Cys Arg Asn
        35                  40                  45

Tyr Asp Val Ala Pro Glu Val Gly His Lys Phe Cys Lys Asp Phe Pro
    50                  55                  60

Gly Phe Ile Pro Ser Leu Leu Lys Arg Leu Leu Asp Glu Arg Gln Lys
65                  70                  75                  80

Ile Lys Thr Lys Met Lys Ala Ser Gln Asp Pro Ile Glu Lys Ile Met
                85                  90                  95

Leu Asp Tyr Arg Gln Arg Ala Ile Lys Ile Leu Ala Asn Ser Tyr Tyr
            100                 105                 110

Gly Tyr Tyr Gly Tyr Ala Lys Ala Arg Trp Tyr Cys Lys Glu Cys Ala
        115                 120                 125

Glu Ser Val Thr Ala Trp Gly Arg Glu Tyr Ile Glu Phe Val Trp Lys
    130                 135                 140

Glu Leu Glu Glu Lys Phe Gly Phe Lys Val Leu Tyr Ile Asp Thr Asp
145                 150                 155                 160

Gly Leu Tyr Ala Thr Ile Pro Gly Gly Lys Ser Glu Glu Ile Lys Lys
                165                 170                 175

Lys Ala Leu Glu Phe Val Asp Tyr Ile Asn Ala Lys Leu Pro Gly Leu
            180                 185                 190

Leu Glu Leu Glu Tyr Glu Gly Phe Tyr Lys Arg Gly Phe Phe Val Thr
        195                 200                 205

Lys Lys Lys Tyr Ala Leu Ile Asp Glu Glu Gly Lys Ile Ile Thr Arg
    210                 215                 220

Gly Leu Glu Ile Val Arg Arg Asp Trp Ser Glu Ile Ala Lys Glu Thr
225                 230                 235                 240
```

```
Gln Ala Arg Val Leu Glu Ala Ile Leu Lys His Gly Asn Val Glu Glu
                245                 250                 255

Ala Val Arg Ile Val Lys Glu Val Thr Gln Lys Leu Ser Lys Tyr Glu
            260                 265                 270

Ile Pro Pro Glu Lys Leu Ala Ile Tyr Glu Gln Ile Thr Arg Pro Leu
        275                 280                 285

His Glu Tyr Lys Ala Ile Gly Pro His Val Ala Val Ala Lys Arg Leu
    290                 295                 300

Ala Ala Lys Gly Val Lys Ile Lys Pro Gly Met Val Ile Gly Tyr Ile
305                 310                 315                 320

Val Leu Arg Gly Asp Gly Pro Ile Ser Asn Arg Ala Ile Leu Ala Glu
                325                 330                 335

Glu Tyr Asp Pro Arg Lys His Lys Tyr Asp Ala Glu Tyr Tyr Ile Glu
            340                 345                 350

Asn Gln Val Leu Pro Ala Val Leu Arg Ile Leu Glu Gly Phe Gly Tyr
        355                 360                 365

Arg Lys Glu Asp Leu Arg Trp Gln Lys Thr Gln Gln Thr Gly Leu
    370                 375                 380

<210> SEQ ID NO 13
<211> LENGTH: 844
<212> TYPE: PRT
<213> ORGANISM: Artificial sequence
<220> FEATURE:
<223> OTHER INFORMATION: Pyrococcus DNA polymerase sequence including
      exonuclease domain and DNA binding domain

<400> SEQUENCE: 13

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
                20                  25                  30

Thr Phe Arg Pro Tyr Ile Tyr Ala Leu Leu Lys Asp Asp Ser Lys Ile
            35                  40                  45

Glu Glu Val Lys Lys Ile Thr Ala Glu Arg His Gly Lys Ile Val Arg
        50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Ile Ile Arg Glu Lys Asp Pro Asp Ile Ile Ile Thr
        195                 200                 205

Tyr Asn Gly Asp Ser Phe Asp Leu Pro Tyr Leu Ala Lys Arg Ala Glu
    210                 215                 220
```

```
Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Thr Gly Glu Gly
            290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
            325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
            405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Lys Ile
            450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
            485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
            565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Ala Ile Leu Lys His Gly Asn Val Glu Glu Ala
625                 630                 635                 640
```

```
Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
            755                 760                 765

Trp Leu Asn Ile Lys Lys Ser Gly Thr Gly Gly Gly Ala Thr Val
            770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
            835                 840

<210> SEQ ID NO 14
<211> LENGTH: 844
<212> TYPE: PRT
<213> ORGANISM: Artificial sequence
<220> FEATURE:
<223> OTHER INFORMATION: Pyrococcus DNA polymerase sequence including
      exonuclease domain and DNA binding domain, K762Q

<400> SEQUENCE: 14

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
            35                  40                  45

Glu Glu Val Lys Lys Ile Thr Ala Glu Arg His Gly Lys Ile Val Arg
50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
            130                 135                 140

Leu Tyr His Glu Gly Glu Glu Phe Gly Lys Gly Pro Ile Ile Met Ile
145                 150                 155                 160
```

-continued

```
Ser Tyr Ala Asp Glu Glu Ala Lys Val Ile Thr Trp Lys Lys Ile
                165                 170                 175
Asp Leu Pro Tyr Val Glu Val Val Ser Ser Arg Glu Met Ile Lys
            180                 185                 190
Arg Phe Leu Lys Ile Ile Arg Glu Lys Asp Pro Asp Ile Ile Thr
        195                 200                 205
Tyr Asn Gly Asp Ser Phe Asp Leu Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Thr Gly Glu Gly
    290                 295                 300
Leu Glu Arg Val Ala Lys Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
    370                 375                 380
Tyr Ala Gly Gly Phe Val Lys Glu Pro Glu Lys Gly Leu Trp Glu Asn
385                 390                 395                 400
Ile Val Ser Leu Asp Phe Arg Ala Leu Tyr Pro Ser Ile Ile Ile Thr
                405                 410                 415
His Asn Val Ser Pro Asp Thr Leu Asn Arg Glu Gly Cys Arg Asn Tyr
            420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Asp Glu Arg Gln Lys Ile
    450                 455                 460
Lys Thr Lys Met Lys Ala Ser Gln Asp Pro Ile Glu Lys Ile Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Trp Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Lys Ser Glu Glu Ile Lys Lys Lys
545                 550                 555                 560
Ala Leu Glu Phe Val Asp Tyr Ile Asn Ala Lys Leu Pro Gly Leu Leu
                565                 570                 575
```

```
Glu Leu Glu Tyr Glu Gly Phe Tyr Lys Arg Gly Phe Val Thr Lys
            580                 585                 590

Lys Lys Tyr Ala Leu Ile Asp Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Gln Thr Gly Leu Thr Ser
        755                 760                 765

Trp Leu Asn Ile Lys Lys Ser Gly Thr Gly Gly Gly Ala Thr Val
    770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
        835                 840

<210> SEQ ID NO 15
<211> LENGTH: 844
<212> TYPE: PRT
<213> ORGANISM: Artificial sequence
<220> FEATURE:
<223> OTHER INFORMATION: Pyrococcus DNA polymerase sequence including
      exonuclease domain and sequence non-specific DNA binding domain,
      A408S K762Q

<400> SEQUENCE: 15

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
```

```
                    85                  90                  95
Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
            130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
                180                 185                 190

Arg Phe Leu Lys Ile Ile Arg Glu Lys Asp Pro Asp Ile Ile Ile Thr
            195                 200                 205

Tyr Asn Gly Asp Ser Phe Asp Leu Pro Tyr Leu Ala Lys Arg Ala Glu
            210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Thr Gly Glu Gly
            290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
            370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Lys Ile
            450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510
```

Ser Val Thr Ala Trp Gly Arg Glu Tyr Ile Glu Phe Val Trp Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Gln Thr Gly Leu Thr Ser
        755                 760                 765

Trp Leu Asn Ile Lys Lys Ser Gly Thr Gly Gly Gly Ala Thr Val
    770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
        835                 840

<210> SEQ ID NO 16
<211> LENGTH: 775
<212> TYPE: PRT
<213> ORGANISM: Artificial Sequence
<220> FEATURE:
<223> OTHER INFORMATION: Deep Vent DNA polymerase

<400> SEQUENCE: 16

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

```
Asn Phe Arg Pro Tyr Ile Tyr Ala Leu Leu Lys Asp Asp Ser Gln Ile
         35                  40                  45

Asp Glu Val Arg Lys Ile Thr Ala Glu Arg His Gly Lys Ile Val Arg
 50                  55                  60

Ile Ile Asp Ala Glu Lys Val Arg Lys Phe Leu Gly Arg Pro Ile
 65                  70                  75                  80

Glu Val Trp Arg Leu Tyr Phe Glu His Pro Gln Asp Val Pro Ala Ile
                 85                  90                  95

Arg Asp Lys Ile Arg Glu His Ser Ala Val Ile Asp Ile Phe Glu Tyr
                    100                 105                 110

Asp Ile Pro Phe Ala Lys Arg Tyr Leu Ile Asp Lys Gly Leu Ile Pro
                115                 120                 125

Met Glu Gly Asp Glu Glu Leu Lys Leu Leu Ala Phe Asp Ile Glu Thr
130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
                180                 185                 190

Arg Phe Leu Lys Val Ile Arg Glu Lys Asp Pro Asp Val Ile Ile Thr
            195                 200                 205

Tyr Asn Gly Asp Ser Phe Asp Leu Pro Tyr Leu Val Lys Arg Ala Glu
210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Tyr Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445
```

```
Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Glu Tyr Ile Glu Phe Val Arg Lys Glu
            515                 520                 525

Leu Glu Glu Lys Phe Gly Phe Lys Val Leu Tyr Ile Asp Thr Asp Gly
530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
                580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Arg Gly Val Lys Val Arg Pro Gly Met Val Ile Gly Tyr Ile Val
            690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
                740                 745                 750

Lys Glu Asp Leu Arg Trp Gln Lys Thr Lys Gln Thr Gly Leu Thr Ala
            755                 760                 765

Trp Leu Asn Ile Lys Lys Lys
    770                 775

<210> SEQ ID NO 17
<211> LENGTH: 775
<212> TYPE: PRT
<213> ORGANISM: Artificial Sequence
<220> FEATURE:
<223> OTHER INFORMATION: K762Q variant of Deep Vent DNA polymerase
      amino acid sequence

<400> SEQUENCE: 17

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30
```

```
Asn Phe Arg Pro Tyr Ile Tyr Ala Leu Leu Lys Asp Asp Ser Gln Ile
         35                  40                  45

Asp Glu Val Arg Lys Ile Thr Ala Glu Arg His Gly Lys Ile Val Arg
 50                  55                  60

Ile Ile Asp Ala Glu Lys Val Arg Lys Phe Leu Gly Arg Pro Ile
 65                  70                  75                  80

Glu Val Trp Arg Leu Tyr Phe Glu His Pro Gln Asp Val Pro Ala Ile
                 85                  90                  95

Arg Asp Lys Ile Arg Glu His Ser Ala Val Ile Asp Ile Phe Glu Tyr
                100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
                180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
                420                 425                 430

Asp Val Ala Pro Glu Val Gly His Lys Phe Cys Lys Asp Phe Pro Gly
        435                 440                 445
```

```
Phe Ile Pro Ser Leu Leu Lys Arg Leu Leu Asp Glu Arg Gln Glu Ile
            450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
            515                 520                 525

Leu Glu Glu Lys Phe Gly Phe Lys Val Leu Tyr Ile Asp Thr Asp Gly
530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
            675                 680                 685

Ala Arg Gly Val Lys Val Arg Pro Gly Met Val Ile Gly Tyr Ile Val
            690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Gln Thr Gly Leu Thr Ala
            755                 760                 765

Trp Leu Asn Ile Lys Lys Lys
    770                 775

<210> SEQ ID NO 18
<211> LENGTH: 383
<212> TYPE: PRT
<213> ORGANISM: Artificial Sequence
<220> FEATURE:
<223> OTHER INFORMATION: Deep Vent DNA polymerase catalytic domain amino
      acid sequence

<400> SEQUENCE: 18

Ser Tyr Ala Gly Gly Tyr Val Lys Glu Pro Glu Lys Gly Leu Trp Glu
1               5                   10                  15

Gly Leu Val Ser Leu Asp Phe Arg Ser Leu Tyr Pro Ser Ile Ile Ile
            20                  25                  30
```

Thr His Asn Val Ser Pro Asp Thr Leu Asn Arg Glu Gly Cys Arg Glu
                35                  40                  45

Tyr Asp Val Ala Pro Glu Val Gly His Lys Phe Cys Lys Asp Phe Pro
         50                  55                  60

Gly Phe Ile Pro Ser Leu Leu Lys Arg Leu Leu Asp Glu Arg Gln Glu
65                  70                  75                  80

Ile Lys Arg Lys Met Lys Ala Ser Lys Asp Pro Ile Glu Lys Lys Met
                 85                  90                  95

Leu Asp Tyr Arg Gln Arg Ala Ile Lys Ile Leu Ala Asn Ser Tyr Tyr
             100                 105                 110

Gly Tyr Tyr Gly Tyr Ala Lys Ala Arg Trp Tyr Cys Lys Glu Cys Ala
             115                 120                 125

Glu Ser Val Thr Ala Trp Gly Arg Glu Tyr Ile Glu Phe Val Arg Lys
         130                 135                 140

Glu Leu Glu Glu Lys Phe Gly Phe Lys Val Leu Tyr Ile Asp Thr Asp
145                 150                 155                 160

Gly Leu Tyr Ala Thr Ile Pro Gly Ala Lys Pro Glu Ile Lys Lys
                 165                 170                 175

Lys Ala Leu Glu Phe Val Asp Tyr Ile Asn Ala Lys Leu Pro Gly Leu
             180                 185                 190

Leu Glu Leu Glu Tyr Glu Gly Phe Tyr Val Arg Gly Phe Phe Val Thr
         195                 200                 205

Lys Lys Lys Tyr Ala Leu Ile Asp Glu Glu Gly Lys Ile Ile Thr Arg
210                 215                 220

Gly Leu Glu Ile Val Arg Arg Asp Trp Ser Glu Ile Ala Lys Glu Thr
225                 230                 235                 240

Gln Ala Lys Val Leu Glu Ala Ile Leu Lys His Gly Asn Val Glu Glu
             245                 250                 255

Ala Val Lys Ile Val Lys Glu Val Thr Glu Lys Leu Ser Lys Tyr Glu
             260                 265                 270

Ile Pro Pro Glu Lys Leu Val Ile Tyr Glu Gln Ile Thr Arg Pro Leu
         275                 280                 285

His Glu Tyr Lys Ala Ile Gly Pro His Val Ala Val Ala Lys Arg Leu
             290                 295                 300

Ala Ala Arg Gly Val Lys Val Arg Pro Gly Met Val Ile Gly Tyr Ile
305                 310                 315                 320

Val Leu Arg Gly Asp Gly Pro Ile Ser Lys Arg Ala Ile Leu Ala Glu
                 325                 330                 335

Glu Phe Asp Leu Arg Lys His Lys Tyr Asp Ala Glu Tyr Tyr Ile Glu
             340                 345                 350

Asn Gln Val Leu Pro Ala Val Leu Arg Ile Leu Glu Ala Phe Gly Tyr
         355                 360                 365

Arg Lys Glu Asp Leu Arg Trp Gln Lys Thr Lys Gln Thr Gly Leu
370                 375                 380

<210> SEQ ID NO 19
<211> LENGTH: 383
<212> TYPE: PRT
<213> ORGANISM: Artificial Sequence
<220> FEATURE:
<223> OTHER INFORMATION: K762Q variant of Deep Vent DNA polymerase
      catalytic domain amino acid sequence

<400> SEQUENCE: 19

Ser Tyr Ala Gly Gly Tyr Val Lys Glu Pro Glu Lys Gly Leu Trp Glu

```
  1               5                  10                 15
Gly Leu Val Ser Leu Asp Phe Arg Ser Leu Tyr Pro Ser Ile Ile Ile
             20                 25                 30

Thr His Asn Val Ser Pro Asp Thr Leu Asn Arg Glu Gly Cys Arg Glu
             35                 40                 45

Tyr Asp Val Ala Pro Glu Val Gly His Lys Phe Cys Lys Asp Phe Pro
 50                 55                 60

Gly Phe Ile Pro Ser Leu Leu Lys Arg Leu Leu Asp Glu Arg Gln Glu
 65                 70                 75                 80

Ile Lys Arg Lys Met Lys Ala Ser Lys Asp Pro Ile Glu Lys Lys Met
                 85                 90                 95

Leu Asp Tyr Arg Gln Arg Ala Ile Lys Ile Leu Ala Asn Ser Tyr Tyr
                100                105                110

Gly Tyr Tyr Gly Tyr Ala Lys Ala Arg Trp Tyr Cys Lys Glu Cys Ala
            115                120                125

Glu Ser Val Thr Ala Trp Gly Arg Glu Tyr Ile Glu Phe Val Arg Lys
130                135                140

Glu Leu Glu Glu Lys Phe Gly Phe Lys Val Leu Tyr Ile Asp Thr Asp
145                150                155                160

Gly Leu Tyr Ala Thr Ile Pro Gly Ala Lys Pro Glu Glu Ile Lys Lys
                165                170                175

Lys Ala Leu Glu Phe Val Asp Tyr Ile Asn Ala Lys Leu Pro Gly Leu
            180                185                190

Leu Glu Leu Glu Tyr Glu Gly Phe Tyr Val Arg Gly Phe Phe Val Thr
            195                200                205

Lys Lys Lys Tyr Ala Leu Ile Asp Glu Glu Gly Lys Ile Ile Thr Arg
210                215                220

Gly Leu Glu Ile Val Arg Arg Asp Trp Ser Glu Ile Ala Lys Glu Thr
225                230                235                240

Gln Ala Lys Val Leu Glu Ala Ile Leu Lys His Gly Asn Val Glu Glu
                245                250                255

Ala Val Lys Ile Val Lys Glu Val Thr Glu Lys Leu Ser Lys Tyr Glu
            260                265                270

Ile Pro Pro Glu Lys Leu Val Ile Tyr Glu Gln Ile Thr Arg Pro Leu
            275                280                285

His Glu Tyr Lys Ala Ile Gly Pro His Val Ala Val Ala Lys Arg Leu
290                295                300

Ala Ala Arg Gly Val Lys Val Arg Pro Gly Met Val Ile Gly Tyr Ile
305                310                315                320

Val Leu Arg Gly Asp Gly Pro Ile Ser Lys Arg Ala Ile Leu Ala Glu
                325                330                335

Glu Phe Asp Leu Arg Lys His Lys Tyr Asp Ala Glu Tyr Tyr Ile Glu
            340                345                350

Asn Gln Val Leu Pro Ala Val Leu Arg Ile Leu Glu Ala Phe Gly Tyr
            355                360                365

Arg Lys Glu Asp Leu Arg Trp Gln Lys Thr Gln Gln Thr Gly Leu
370                375                380
```

<210> SEQ ID NO 20
<211> LENGTH: 844
<212> TYPE: PRT
<213> ORGANISM: Artificial Sequence
<220> FEATURE:
<223> OTHER INFORMATION: Deep Vent DNA polymerase amino acid sequence
      with DNA binding domain

<400> SEQUENCE: 20

```
Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Lys Asp Asp Ser Gln Ile
            35                  40                  45

Asp Glu Val Arg Lys Ile Thr Ala Glu Arg His Gly Lys Ile Val Arg
        50                  55                  60

Ile Ile Asp Ala Glu Lys Val Arg Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
        130                 135                 140

Leu Tyr His Glu Gly Glu Glu Phe Ala Lys Gly Pro Ile Ile Met Ile
145                 150                 155                 160

Ser Tyr Ala Asp Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
            195                 200                 205

Tyr Asn Gly Asp Ser Phe Asp Leu Pro Tyr Leu Val Lys Arg Ala Glu
            210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
        290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
        370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
```

-continued

```
                405                 410                 415
His Asn Val Ser Pro Asp Thr Leu Asn Arg Glu Gly Cys Arg Glu Tyr
                420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
            755                 760                 765

Trp Leu Asn Ile Lys Lys Lys Gly Thr Gly Gly Gly Ala Thr Val
            770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830
```

Lys Glu Leu Leu Gln Met Leu Glu Lys Gln Lys Lys
        835                 840

<210> SEQ ID NO 21
<211> LENGTH: 844
<212> TYPE: PRT
<213> ORGANISM: Artificial Sequence
<220> FEATURE:
<223> OTHER INFORMATION: K762Q variant of Deep Vent DNA polymerase amino
      acid sequence with DNA binding domain

<400> SEQUENCE: 21

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu

-continued

```
                340                 345                 350
Val Glu Trp Tyr Leu Leu Arg Lys Ala Tyr Glu Arg Asn Glu Leu Ala
            355                 360                 365
Pro Asn Lys Pro Asp Glu Arg Glu Tyr Glu Arg Arg Leu Arg Glu Ser
        370                 375                 380
Tyr Ala Gly Gly Tyr Val Lys Glu Pro Glu Lys Gly Leu Trp Glu Gly
385                 390                 395                 400
Leu Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
            420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Asp Glu Arg Gln Glu Ile
450                 455                 460
Lys Arg Lys Met Lys Ala Ser Lys Asp Pro Ile Glu Lys Lys Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Arg Lys Glu
        515                 520                 525
Leu Glu Glu Lys Phe Gly Phe Lys Val Leu Tyr Ile Asp Thr Asp Gly
        530                 535                 540
Leu Tyr Ala Thr Ile Pro Gly Ala Lys Pro Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Val Arg Gly Phe Phe Val Thr Lys
            580                 585                 590
Lys Lys Tyr Ala Leu Ile Asp Glu Glu Gly Lys Ile Ile Thr Arg Gly
        595                 600                 605
Leu Glu Ile Val Arg Arg Asp Trp Ser Glu Ile Ala Lys Glu Thr Gln
    610                 615                 620
Ala Lys Val Leu Glu Ala Ile Leu Lys His Gly Asn Val Glu Glu Ala
625                 630                 635                 640
Val Lys Ile Val Lys Glu Val Thr Glu Lys Leu Ser Lys Tyr Glu Ile
                645                 650                 655
Pro Pro Glu Lys Leu Val Ile Tyr Glu Gln Ile Thr Arg Pro Leu His
            660                 665                 670
Glu Tyr Lys Ala Ile Gly Pro His Val Ala Val Ala Lys Arg Leu Ala
        675                 680                 685
Ala Arg Gly Val Lys Val Arg Pro Gly Met Val Ile Gly Tyr Ile Val
        690                 695                 700
Leu Arg Gly Asp Gly Pro Ile Ser Lys Arg Ala Ile Leu Ala Glu Glu
705                 710                 715                 720
Phe Asp Leu Arg Lys His Lys Tyr Asp Ala Glu Tyr Tyr Ile Glu Asn
                725                 730                 735
Gln Val Leu Pro Ala Val Leu Arg Ile Leu Glu Ala Phe Gly Tyr Arg
            740                 745                 750
Lys Glu Asp Leu Arg Trp Gln Lys Thr Gln Gln Thr Gly Leu Thr Ala
        755                 760                 765
```

```
Trp Leu Asn Ile Lys Lys Gly Thr Gly Gly Gly Ala Thr Val
    770             775             780

Lys Phe Lys Tyr Lys Gly Glu Glu Lys Glu Val Asp Ile Ser Lys Ile
785             790             795             800

Lys Lys Val Trp Arg Val Gly Lys Met Ile Ser Phe Thr Tyr Asp Glu
                805             810             815

Gly Gly Gly Lys Thr Gly Arg Gly Ala Val Ser Glu Lys Asp Ala Pro
            820             825             830

Lys Glu Leu Leu Gln Met Leu Glu Lys Gln Lys Lys
        835             840
```

<210> SEQ ID NO 22
<211> LENGTH: 774
<212> TYPE: PRT
<213> ORGANISM: Thermococcus litoralis

<400> SEQUENCE: 22

```
Met Ile Leu Asp Thr Asp Tyr Ile Thr Lys Asp Gly Lys Pro Ile Ile
1               5               10              15

Arg Ile Phe Lys Lys Glu Asn Gly Glu Phe Lys Ile Glu Leu Asp Pro
            20              25              30

His Phe Gln Pro Tyr Ile Tyr Ala Leu Leu Lys Asp Asp Ser Ala Ile
        35              40              45

Glu Glu Ile Lys Ala Ile Lys Gly Glu Arg His Gly Lys Thr Val Arg
    50              55              60

Val Leu Asp Ala Val Lys Val Arg Lys Lys Phe Leu Gly Arg Glu Val
65              70              75              80

Glu Val Trp Lys Leu Ile Phe Glu His Pro Gln Asp Val Pro Ala Met
                85              90              95

Arg Gly Lys Ile Arg Glu His Pro Ala Val Val Asp Ile Tyr Glu Tyr
            100             105             110

Asp Ile Pro Phe Ala Lys Arg Tyr Leu Ile Asp Lys Gly Leu Ile Pro
        115             120             125

Met Glu Gly Asp Glu Glu Leu Lys Leu Leu Ala Phe Asp Ile Glu Thr
    130             135             140

Phe Tyr His Glu Gly Asp Glu Phe Gly Lys Gly Glu Ile Ile Met Ile
145             150             155             160

Ser Tyr Ala Asp Glu Glu Ala Arg Val Ile Thr Trp Lys Asn Ile
                165             170             175

Asp Leu Pro Tyr Val Asp Val Val Ser Asn Glu Arg Glu Met Ile Lys
            180             185             190

Arg Phe Val Gln Val Val Lys Glu Lys Asp Pro Asp Val Ile Ile Thr
        195             200             205

Tyr Asn Gly Asp Asn Phe Asp Leu Pro Tyr Leu Ile Lys Arg Ala Glu
    210             215             220

Lys Leu Gly Val Arg Leu Val Leu Gly Arg Asp Lys Glu His Pro Glu
225             230             235             240

Pro Lys Ile Gln Arg Met Gly Asp Ser Phe Ala Val Glu Ile Lys Gly
                245             250             255

Arg Ile His Phe Asp Leu Phe Pro Val Val Arg Arg Thr Ile Asn Leu
            260             265             270

Pro Thr Tyr Thr Leu Glu Ala Val Tyr Glu Ala Val Leu Gly Lys Thr
        275             280             285

Lys Ser Lys Leu Gly Ala Glu Glu Ile Ala Ala Ile Trp Glu Thr Glu
```

```
              290                 295                 300
Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                    325                 330                 335

Lys Leu Ile Gly Gln Ser Val Trp Asp Val Ser Arg Ser Ser Thr Gly
                    340                 345                 350

Asn Leu Val Glu Trp Tyr Leu Leu Arg Val Ala Tyr Ala Arg Asn Glu
                355                 360                 365

Leu Ala Pro Asn Lys Pro Asp Glu Glu Tyr Lys Arg Arg Leu Arg
            370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                    405                 410                 415

Val Thr His Asn Val Ser Pro Asp Thr Leu Glu Lys Glu Gly Cys Lys
                420                 425                 430

Asn Tyr Asp Val Ala Pro Ile Val Gly Tyr Arg Phe Cys Lys Asp Phe
                435                 440                 445

Pro Gly Phe Ile Pro Ser Ile Leu Gly Asp Leu Ile Ala Met Arg Gln
            450                 455                 460

Asp Ile Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
                500                 505                 510

Ala Glu Ser Val Thr Ala Trp Gly Arg His Tyr Ile Glu Met Thr Ile
            515                 520                 525

Arg Glu Ile Glu Glu Lys Phe Gly Phe Lys Val Leu Tyr Ala Asp Thr
            530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
                580                 585                 590

Thr Lys Lys Arg Tyr Ala Val Ile Asp Glu Glu Gly Arg Ile Thr Thr
            595                 600                 605

Arg Gly Leu Glu Val Val Arg Arg Asp Trp Ser Glu Ile Ala Lys Glu
            610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                    645                 650                 655

Arg Val Pro Leu Glu Lys Leu Val Ile His Glu Gln Ile Thr Arg Asp
                660                 665                 670

Leu Lys Asp Tyr Lys Ala Ile Gly Pro His Val Ala Ile Ala Lys Arg
                675                 680                 685

Leu Ala Ala Arg Gly Ile Lys Val Lys Pro Gly Thr Ile Ile Ser Tyr
            690                 695                 700

Ile Val Leu Lys Gly Ser Gly Lys Ile Ser Asp Arg Val Ile Leu Leu
705                 710                 715                 720
```

```
Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770

<210> SEQ ID NO 23
<211> LENGTH: 774
<212> TYPE: PRT
<213> ORGANISM: Artificial sequence
<220> FEATURE:
<223> OTHER INFORMATION: K764Q variant of Thermococcus litoralis DNA
      polymerase

<400> SEQUENCE: 23

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
```

```
            290                 295                 300
Glu Ser Met Lys Lys Leu Ala Gln Tyr Ser Met Glu Asp Ala Arg Ala
305                 310                 315                 320
Thr Tyr Glu Leu Gly Lys Glu Phe Phe Pro Met Glu Ala Glu Leu Ala
                    325                 330                 335
Lys Leu Ile Gly Gln Ser Val Trp Asp Val Ser Arg Ser Thr Gly
                340                 345                 350
Asn Leu Val Glu Trp Tyr Leu Leu Arg Val Ala Tyr Ala Arg Asn Glu
                355                 360                 365
Leu Ala Pro Asn Lys Pro Asp Glu Glu Tyr Lys Arg Arg Leu Arg
    370                 375                 380
Thr Thr Tyr Leu Gly Gly Tyr Val Lys Glu Pro Glu Lys Gly Leu Trp
385                 390                 395                 400
Glu Asn Ile Ile Tyr Leu Asp Phe Arg Ser Leu Tyr Pro Ser Ile Ile
                405                 410                 415
Val Thr His Asn Val Ser Pro Asp Thr Leu Glu Lys Glu Gly Cys Lys
                420                 425                 430
Asn Tyr Asp Val Ala Pro Ile Val Gly Tyr Arg Phe Cys Lys Asp Phe
            435                 440                 445
Pro Gly Phe Ile Pro Ser Ile Leu Gly Asp Leu Ile Ala Met Arg Gln
            450                 455                 460
Asp Ile Lys Lys Met Lys Ser Thr Ile Asp Pro Ile Glu Lys Lys
465                 470                 475                 480
Met Leu Asp Tyr Arg Gln Arg Ala Ile Lys Leu Leu Ala Asn Ser Tyr
                485                 490                 495
Tyr Gly Tyr Met Gly Tyr Pro Lys Ala Arg Trp Tyr Ser Lys Glu Cys
                500                 505                 510
Ala Glu Ser Val Thr Ala Trp Gly Arg His Tyr Ile Glu Met Thr Ile
                515                 520                 525
Arg Glu Ile Glu Glu Lys Phe Gly Phe Lys Val Leu Tyr Ala Asp Thr
                530                 535                 540
Asp Gly Phe Tyr Ala Thr Ile Pro Gly Glu Lys Pro Glu Leu Ile Lys
545                 550                 555                 560
Lys Lys Ala Lys Glu Phe Leu Asn Tyr Ile Asn Ser Lys Leu Pro Gly
                565                 570                 575
Leu Leu Glu Leu Glu Tyr Glu Gly Phe Tyr Leu Arg Gly Phe Phe Val
                580                 585                 590
Thr Lys Lys Arg Tyr Ala Val Ile Asp Glu Glu Gly Arg Ile Thr Thr
                595                 600                 605
Arg Gly Leu Glu Val Val Arg Arg Asp Trp Ser Glu Ile Ala Lys Glu
    610                 615                 620
Thr Gln Ala Lys Val Leu Glu Ala Ile Leu Lys Glu Gly Ser Val Glu
625                 630                 635                 640
Lys Ala Val Glu Val Val Arg Asp Val Val Glu Lys Ile Ala Lys Tyr
                645                 650                 655
Arg Val Pro Leu Glu Lys Leu Val Ile His Glu Gln Ile Thr Arg Asp
                660                 665                 670
Leu Lys Asp Tyr Lys Ala Ile Gly Pro His Val Ala Ile Ala Lys Arg
            675                 680                 685
Leu Ala Ala Arg Gly Ile Lys Val Lys Pro Gly Thr Ile Ile Ser Tyr
            690                 695                 700
Ile Val Leu Lys Gly Ser Gly Lys Ile Ser Asp Arg Val Ile Leu Leu
705                 710                 715                 720
```

```
Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Gln Gln Thr Gly Leu
        755                 760                 765

Asp Ala Trp Leu Lys Arg
    770

<210> SEQ ID NO 24
<211> LENGTH: 383
<212> TYPE: PRT
<213> ORGANISM: Artificial sequence
<220> FEATURE:
<223> OTHER INFORMATION: Thermococcus litoralis DNA polymerase catalytic
      domain amino acid sequence

<400> SEQUENCE: 24

Thr Tyr Leu Gly Gly Tyr Val Lys Glu Pro Glu Lys Gly Leu Trp Glu
1               5                   10                  15

Asn Ile Ile Tyr Leu Asp Phe Arg Ser Leu Tyr Pro Ser Ile Ile Val
            20                  25                  30

Thr His Asn Val Ser Pro Asp Thr Leu Glu Lys Glu Gly Cys Lys Asn
        35                  40                  45

Tyr Asp Val Ala Pro Ile Val Gly Tyr Arg Phe Cys Lys Asp Phe Pro
    50                  55                  60

Gly Phe Ile Pro Ser Ile Leu Gly Asp Leu Ile Ala Met Arg Gln Asp
65                  70                  75                  80

Ile Lys Lys Lys Met Lys Ser Thr Ile Asp Pro Ile Glu Lys Lys Met
                85                  90                  95

Leu Asp Tyr Arg Gln Arg Ala Ile Lys Leu Leu Ala Asn Ser Tyr Tyr
            100                 105                 110

Gly Tyr Met Gly Tyr Pro Lys Ala Arg Trp Tyr Ser Lys Glu Cys Ala
        115                 120                 125

Glu Ser Val Thr Ala Trp Gly Arg His Tyr Ile Glu Met Thr Ile Arg
    130                 135                 140

Glu Ile Glu Glu Lys Phe Gly Phe Lys Val Leu Tyr Ala Asp Thr Asp
145                 150                 155                 160

Gly Phe Tyr Ala Thr Ile Pro Gly Glu Lys Pro Glu Leu Ile Lys Lys
                165                 170                 175

Lys Ala Lys Glu Phe Leu Asn Tyr Ile Asn Ser Lys Leu Pro Gly Leu
            180                 185                 190

Leu Glu Leu Glu Tyr Glu Gly Phe Tyr Leu Arg Gly Phe Phe Val Thr
        195                 200                 205

Lys Lys Arg Tyr Ala Val Ile Asp Glu Glu Gly Arg Ile Thr Thr Arg
    210                 215                 220

Gly Leu Glu Val Val Arg Arg Asp Trp Ser Glu Ile Ala Lys Glu Thr
225                 230                 235                 240

Gln Ala Lys Val Leu Glu Ala Ile Leu Lys Glu Gly Ser Val Glu Lys
                245                 250                 255

Ala Val Glu Val Val Arg Asp Val Val Glu Lys Ile Ala Lys Tyr Arg
            260                 265                 270

Val Pro Leu Glu Lys Leu Val Ile His Glu Gln Ile Thr Arg Asp Leu
        275                 280                 285

Lys Asp Tyr Lys Ala Ile Gly Pro His Val Ala Ile Ala Lys Arg Leu
```

```
                    290                 295                 300
Ala Ala Arg Gly Ile Lys Val Lys Pro Gly Thr Ile Ile Ser Tyr Ile
305                 310                 315                 320

Val Leu Lys Gly Ser Gly Lys Ile Ser Asp Arg Val Ile Leu Leu Thr
                    325                 330                 335

Glu Tyr Asp Pro Arg Lys His Lys Tyr Asp Pro Asp Tyr Tyr Ile Glu
                    340                 345                 350

Asn Gln Val Leu Pro Ala Val Leu Arg Ile Leu Glu Ala Phe Gly Tyr
                355                 360                 365

Arg Lys Glu Asp Leu Arg Tyr Gln Ser Ser Lys Gln Thr Gly Leu
                370                 375                 380

<210> SEQ ID NO 25
<211> LENGTH: 383
<212> TYPE: PRT
<213> ORGANISM: Artificial sequence
<220> FEATURE:
<223> OTHER INFORMATION: K764Q variant of Thermococcus litoralis DNA
      polymerase catalytic domain amino acid sequence

<400> SEQUENCE: 25

Thr Tyr Leu Gly Gly Tyr Val Lys Glu Pro Glu Lys Gly Leu Trp Glu
1               5                   10                  15

Asn Ile Ile Tyr Leu Asp Phe Arg Ser Leu Tyr Pro Ser Ile Ile Val
                20                  25                  30

Thr His Asn Val Ser Pro Asp Thr Leu Glu Lys Glu Gly Cys Lys Asn
            35                  40                  45

Tyr Asp Val Ala Pro Ile Val Gly Tyr Arg Phe Cys Lys Asp Phe Pro
50                  55                  60

Gly Phe Ile Pro Ser Ile Leu Gly Asp Leu Ile Ala Met Arg Gln Asp
65                  70                  75                  80

Ile Lys Lys Lys Met Lys Ser Thr Ile Asp Pro Ile Glu Lys Lys Met
                85                  90                  95

Leu Asp Tyr Arg Gln Arg Ala Ile Lys Leu Leu Ala Asn Ser Tyr Tyr
                100                 105                 110

Gly Tyr Met Gly Tyr Pro Lys Ala Arg Trp Tyr Ser Lys Glu Cys Ala
            115                 120                 125

Glu Ser Val Thr Ala Trp Gly Arg His Tyr Ile Glu Met Thr Ile Arg
130                 135                 140

Glu Ile Glu Glu Lys Phe Gly Phe Lys Val Leu Tyr Ala Asp Thr Asp
145                 150                 155                 160

Gly Phe Tyr Ala Thr Ile Pro Gly Glu Lys Pro Glu Leu Ile Lys Lys
                165                 170                 175

Lys Ala Lys Glu Phe Leu Asn Tyr Ile Asn Ser Lys Leu Pro Gly Leu
            180                 185                 190

Leu Glu Leu Glu Tyr Glu Gly Phe Tyr Leu Arg Gly Phe Phe Val Thr
        195                 200                 205

Lys Lys Arg Tyr Ala Val Ile Asp Glu Glu Gly Arg Ile Thr Thr Arg
        210                 215                 220

Gly Leu Glu Val Val Arg Arg Asp Trp Ser Glu Ile Ala Lys Glu Thr
225                 230                 235                 240

Gln Ala Lys Val Leu Glu Ala Ile Leu Lys Glu Gly Ser Val Glu Lys
                245                 250                 255

Ala Val Glu Val Val Arg Asp Val Val Glu Lys Ile Ala Lys Tyr Arg
            260                 265                 270
```

```
Val Pro Leu Glu Lys Leu Val Ile His Glu Gln Ile Thr Arg Asp Leu
            275                 280                 285

Lys Asp Tyr Lys Ala Ile Gly Pro His Val Ala Ile Ala Lys Arg Leu
        290                 295                 300

Ala Ala Arg Gly Ile Lys Val Lys Pro Gly Thr Ile Ile Ser Tyr Ile
305                 310                 315                 320

Val Leu Lys Gly Ser Gly Lys Ile Ser Asp Arg Val Ile Leu Leu Thr
                325                 330                 335

Glu Tyr Asp Pro Arg Lys His Lys Tyr Asp Pro Asp Tyr Tyr Ile Glu
            340                 345                 350

Asn Gln Val Leu Pro Ala Val Leu Arg Ile Leu Glu Ala Phe Gly Tyr
        355                 360                 365

Arg Lys Glu Asp Leu Arg Tyr Gln Ser Ser Gln Gln Thr Gly Leu
    370                 375                 380

<210> SEQ ID NO 26
<211> LENGTH: 774
<212> TYPE: PRT
<213> ORGANISM: Thermococcus litoralis

<400> SEQUENCE: 26

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Ser Val Arg
    50                  55                  60

Val Val Asp Ala Val Lys Val Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Asp Lys Ile Lys Glu His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu Asn Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270
```

-continued

```
Pro Thr Tyr Thr Leu Glu Ala Val Tyr Glu Ala Val Leu Gly Lys Thr
        275                 280                 285
Lys Ser Lys Leu Gly Ala Glu Glu Ile Ala Ala Ile Trp Glu Thr Glu
290                 295                 300
Glu Ser Met Lys Lys Leu Ala Gln Tyr Ser Met Glu Asp Ala Arg Ala
305                 310                 315                 320
Thr Tyr Glu Leu Gly Lys Glu Phe Phe Pro Met Glu Ala Glu Leu Ala
                325                 330                 335
Lys Leu Ile Gly Gln Ser Val Trp Asp Val Ser Arg Ser Ser Thr Gly
                340                 345                 350
Asn Leu Val Glu Trp Tyr Leu Leu Arg Val Ala Tyr Glu Arg Asn Glu
                355                 360                 365
Leu Ala Pro Asn Lys Pro Asp Glu Glu Glu Tyr Lys Arg Arg Leu Arg
370                 375                 380
Thr Thr Tyr Leu Gly Gly Tyr Val Lys Glu Pro Glu Lys Gly Leu Trp
385                 390                 395                 400
Glu Asn Ile Ile Tyr Leu Asp Phe Arg Ser Leu Tyr Pro Ser Ile Ile
                405                 410                 415
Val Thr His Asn Val Ser Pro Asp Thr Leu Lys Glu Gly Cys Glu
                420                 425                 430
Asn Tyr Asp Ile Ala Pro Ile Val Ser Tyr Arg Phe Cys Lys Asp Phe
        435                 440                 445
Pro Gly Phe Ile Pro Ser Ile Leu Gly Asp Leu Ile Ala Met Arg Gln
    450                 455                 460
Glu Ile Lys Lys Lys Met Lys Ala Thr Ile Asp Pro Val Glu Arg Lys
465                 470                 475                 480
Met Leu Asp Tyr Arg Gln Arg Ala Val Lys Leu Leu Ala Asn Ser Tyr
                485                 490                 495
Tyr Gly Tyr Met Gly Tyr Pro Lys Ala Arg Trp Tyr Ser Lys Glu Cys
                500                 505                 510
Ala Glu Ser Val Thr Ala Trp Gly Arg His Tyr Ile Glu Met Thr Ile
        515                 520                 525
Lys Glu Ile Glu Glu Lys Phe Gly Phe Lys Val Leu Tyr Ala Asp Thr
    530                 535                 540
Asp Gly Phe Tyr Ala Thr Ile Ser Gly Glu Lys Pro Glu Ile Ile Lys
545                 550                 555                 560
Lys Lys Ala Arg Glu Phe Leu Asn Tyr Ile Asn Ser Lys Leu Pro Gly
                565                 570                 575
Leu Leu Glu Leu Glu Tyr Glu Gly Phe Tyr Leu Arg Gly Phe Phe Val
                580                 585                 590
Thr Lys Lys Arg Tyr Ala Val Ile Asp Glu Glu Gly Arg Ile Thr Thr
        595                 600                 605
Arg Gly Leu Glu Val Val Arg Arg Asp Trp Ser Glu Ile Ala Lys Glu
    610                 615                 620
Thr Gln Ala Lys Val Leu Glu Ala Ile Leu Lys Asp Gly Ser Val Glu
625                 630                 635                 640
Lys Ala Val Glu Ile Val Arg Asp Val Leu Glu Lys Ile Ala Lys Tyr
                645                 650                 655
Arg Val Pro Leu Glu Lys Leu Val Ile His Glu Gln Ile Thr Arg Asp
                660                 665                 670
Leu Lys Asp Tyr Lys Ala Ile Gly Pro His Val Ala Ile Ala Lys Arg
        675                 680                 685
```

```
Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Glu Lys His Lys Tyr Asp Pro Asp Tyr Tyr Ile
                    725                 730                 735

Glu Asn Gln Val Leu Pro Ala Val Leu Arg Ile Leu Glu Ala Phe Gly
                740                 745                 750

Tyr Arg Lys Glu Asp Leu Arg Tyr Gln Ser Ser Lys Gln Thr Gly Leu
            755                 760                 765

Asp Ala Trp Leu Lys Arg
    770
```

<210> SEQ ID NO 27
<211> LENGTH: 774
<212> TYPE: PRT
<213> ORGANISM: Artificial sequence
<220> FEATURE:
<223> OTHER INFORMATION: K764Q variant of Thermococcus litoralis DNA
  polymerase, sequence 2 (acc. ADK47977.1)

<400> SEQUENCE: 27

```
Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Ser Val Arg
    50                  55                  60

Val Val Asp Ala Val Lys Val Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Asp Lys Ile Lys Glu His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu Asn Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270
```

```
Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
                340                 345                 350

Asn Leu Val Glu Trp Tyr Leu Leu Arg Val Ala Tyr Glu Arg Asn Glu
                355                 360                 365

Leu Ala Pro Asn Lys Pro Asp Glu Glu Glu Tyr Lys Arg Arg Leu Arg
                370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Lys Glu Gly Cys Glu
                420                 425                 430

Asn Tyr Asp Ile Ala Pro Ile Val Ser Tyr Arg Phe Cys Lys Asp Phe
                435                 440                 445

Pro Gly Phe Ile Pro Ser Ile Leu Gly Asp Leu Ile Ala Met Arg Gln
                450                 455                 460

Glu Ile Lys Lys Lys Met Lys Ala Thr Ile Asp Pro Val Glu Arg Lys
465                 470                 475                 480

Met Leu Asp Tyr Arg Gln Arg Ala Val Lys Leu Leu Ala Asn Ser Tyr
                485                 490                 495

Tyr Gly Tyr Met Gly Tyr Pro Lys Ala Arg Trp Tyr Ser Lys Glu Cys
                500                 505                 510

Ala Glu Ser Val Thr Ala Trp Gly Arg His Tyr Ile Glu Met Thr Ile
                515                 520                 525

Lys Glu Ile Glu Glu Lys Phe Gly Phe Lys Val Leu Tyr Ala Asp Thr
                530                 535                 540

Asp Gly Phe Tyr Ala Thr Ile Ser Gly Glu Lys Pro Glu Ile Ile Lys
545                 550                 555                 560

Lys Lys Ala Arg Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
                580                 585                 590

Thr Lys Lys Arg Tyr Ala Val Ile Asp Glu Glu Gly Arg Ile Thr Thr
                595                 600                 605

Arg Gly Leu Glu Val Val Arg Arg Asp Trp Ser Glu Ile Ala Lys Glu
610                 615                 620

Thr Gln Ala Lys Val Leu Glu Ala Ile Leu Lys Asp Gly Ser Val Glu
625                 630                 635                 640

Lys Ala Val Glu Ile Val Arg Asp Val Leu Glu Lys Ile Ala Lys Tyr
                645                 650                 655

Arg Val Pro Leu Glu Lys Leu Val Ile His Glu Gln Ile Thr Arg Asp
                660                 665                 670

Leu Lys Asp Tyr Lys Ala Ile Gly Pro His Val Ala Ile Ala Lys Arg
                675                 680                 685
```

```
Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Glu Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Gln Thr Gly Leu
            755                 760                 765

Asp Ala Trp Leu Lys Arg
    770
```

<210> SEQ ID NO 28
<211> LENGTH: 383
<212> TYPE: PRT
<213> ORGANISM: Artificial sequence
<220> FEATURE:
<223> OTHER INFORMATION: Thermococcus litoralis DNA polymerase, sequence
      2 (acc. ADK47977.1), catalytic domain amino acid sequence

<400> SEQUENCE: 28

```
Thr Tyr Leu Gly Gly Tyr Val Lys Glu Pro Glu Lys Gly Leu Trp Glu
1               5                   10                  15

Asn Ile Ile Tyr Leu Asp Phe Arg Ser Leu Tyr Pro Ser Ile Ile Val
            20                  25                  30

Thr His Asn Val Ser Pro Asp Thr Leu Glu Lys Glu Gly Cys Glu Asn
        35                  40                  45

Tyr Asp Ile Ala Pro Ile Val Ser Tyr Arg Phe Cys Lys Asp Phe Pro
50                  55                  60

Gly Phe Ile Pro Ser Ile Leu Gly Asp Leu Ile Ala Met Arg Gln Glu
65                  70                  75                  80

Ile Lys Lys Lys Met Lys Ala Thr Ile Asp Pro Val Glu Arg Lys Met
                85                  90                  95

Leu Asp Tyr Arg Gln Arg Ala Val Lys Leu Leu Ala Asn Ser Tyr Tyr
            100                 105                 110

Gly Tyr Met Gly Tyr Pro Lys Ala Arg Trp Tyr Ser Lys Glu Cys Ala
        115                 120                 125

Glu Ser Val Thr Ala Trp Gly Arg His Tyr Ile Glu Met Thr Ile Lys
    130                 135                 140

Glu Ile Glu Glu Lys Phe Gly Phe Lys Val Leu Tyr Ala Asp Thr Asp
145                 150                 155                 160

Gly Phe Tyr Ala Thr Ile Ser Gly Glu Lys Pro Glu Ile Ile Lys Lys
                165                 170                 175

Lys Ala Arg Glu Phe Leu Asn Tyr Ile Asn Ser Lys Leu Pro Gly Leu
            180                 185                 190

Leu Glu Leu Glu Tyr Glu Gly Phe Tyr Leu Arg Gly Phe Phe Val Thr
        195                 200                 205

Lys Lys Arg Tyr Ala Val Ile Asp Glu Glu Gly Arg Ile Thr Thr Arg
    210                 215                 220

Gly Leu Glu Val Val Arg Arg Asp Trp Ser Glu Ile Ala Lys Glu Thr
225                 230                 235                 240

Gln Ala Lys Val Leu Glu Ala Ile Leu Lys Asp Gly Ser Val Glu Lys
                245                 250                 255

Ala Val Glu Ile Val Arg Asp Val Leu Glu Lys Ile Ala Lys Tyr Arg
            260                 265                 270
```

Val Pro Leu Glu Lys Leu Val Ile His Glu Gln Ile Thr Arg Asp Leu
            275                 280                 285

Lys Asp Tyr Lys Ala Ile Gly Pro His Val Ala Ile Ala Lys Arg Leu
        290                 295                 300

Ala Ala Arg Gly Ile Lys Val Lys Pro Gly Thr Ile Ile Ser Tyr Ile
305                 310                 315                 320

Val Leu Lys Gly Ser Gly Lys Ile Ser Asp Arg Val Ile Leu Leu Thr
                325                 330                 335

Glu Tyr Asp Pro Glu Lys His Lys Tyr Asp Pro Asp Tyr Tyr Ile Glu
            340                 345                 350

Asn Gln Val Leu Pro Ala Val Leu Arg Ile Leu Glu Ala Phe Gly Tyr
        355                 360                 365

Arg Lys Glu Asp Leu Arg Tyr Gln Ser Ser Lys Gln Thr Gly Leu
    370                 375                 380

<210> SEQ ID NO 29
<211> LENGTH: 383
<212> TYPE: PRT
<213> ORGANISM: Artificial sequence
<220> FEATURE:
<223> OTHER INFORMATION: K764Q variant of Thermococcus litoralis DNA
      polymerase, sequence 2 (acc. ADK47977.1), catalytic domain amino
      acid sequence

<400> SEQUENCE: 29

Thr Tyr Leu Gly Gly Tyr Val Lys Glu Pro Glu Lys Gly Leu Trp Glu
1               5                   10                  15

Asn Ile Ile Tyr Leu Asp Phe Arg Ser Leu Tyr Pro Ser Ile Ile Val
            20                  25                  30

Thr His Asn Val Ser Pro Asp Thr Leu Glu Lys Glu Gly Cys Glu Asn
        35                  40                  45

Tyr Asp Ile Ala Pro Ile Val Ser Tyr Arg Phe Cys Lys Asp Phe Pro
    50                  55                  60

Gly Phe Ile Pro Ser Ile Leu Gly Asp Leu Ile Ala Met Arg Gln Glu
65                  70                  75                  80

Ile Lys Lys Lys Met Lys Ala Thr Ile Asp Pro Val Glu Arg Lys Met
                85                  90                  95

Leu Asp Tyr Arg Gln Arg Ala Val Lys Leu Leu Ala Asn Ser Tyr Tyr
            100                 105                 110

Gly Tyr Met Gly Tyr Pro Lys Ala Arg Trp Tyr Ser Lys Glu Cys Ala
        115                 120                 125

Glu Ser Val Thr Ala Trp Gly Arg His Tyr Ile Glu Met Thr Ile Lys
    130                 135                 140

Glu Ile Glu Glu Lys Phe Gly Phe Lys Val Leu Tyr Ala Asp Thr Asp
145                 150                 155                 160

Gly Phe Tyr Ala Thr Ile Ser Gly Glu Lys Pro Glu Ile Ile Lys Lys
                165                 170                 175

Lys Ala Arg Glu Phe Leu Asn Tyr Ile Asn Ser Lys Leu Pro Gly Leu
            180                 185                 190

Leu Glu Leu Glu Tyr Glu Gly Phe Tyr Leu Arg Gly Phe Phe Val Thr
        195                 200                 205

Lys Lys Arg Tyr Ala Val Ile Asp Glu Glu Gly Arg Ile Thr Thr Arg
    210                 215                 220

Gly Leu Glu Val Val Arg Arg Asp Trp Ser Glu Ile Ala Lys Glu Thr
225                 230                 235                 240

```
Gln Ala Lys Val Leu Glu Ala Ile Leu Lys Asp Gly Ser Val Glu Lys
                245                 250                 255

Ala Val Glu Ile Val Arg Asp Val Leu Glu Lys Ile Ala Lys Tyr Arg
            260                 265                 270

Val Pro Leu Glu Lys Leu Val Ile His Glu Gln Ile Thr Arg Asp Leu
        275                 280                 285

Lys Asp Tyr Lys Ala Ile Gly Pro His Val Ala Ile Ala Lys Arg Leu
    290                 295                 300

Ala Ala Arg Gly Ile Lys Val Lys Pro Gly Thr Ile Ile Ser Tyr Ile
305                 310                 315                 320

Val Leu Lys Gly Ser Gly Lys Ile Ser Asp Arg Val Ile Leu Leu Thr
                325                 330                 335

Glu Tyr Asp Pro Glu Lys His Lys Tyr Asp Pro Asp Tyr Tyr Ile Glu
            340                 345                 350

Asn Gln Val Leu Pro Ala Val Leu Arg Ile Leu Glu Ala Phe Gly Tyr
        355                 360                 365

Arg Lys Glu Asp Leu Arg Tyr Gln Ser Ser Gln Gln Thr Gly Leu
    370                 375                 380

<210> SEQ ID NO 30
<211> LENGTH: 773
<212> TYPE: PRT
<213> ORGANISM: Thermococcus gorgonarius

<400> SEQUENCE: 30

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240
```

-continued

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
            275                 280                 285

Lys Val Tyr Ala Glu Glu Ile Ala Gln Ala Trp Glu Thr Gly Glu Gly
            290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
            325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Leu Ala Arg Arg Arg Glu Ser Tyr
            370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
            405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
            435                 440                 445

Ile Pro Ser Leu Leu Gly Asp Leu Leu Glu Glu Arg Gln Lys Val Lys
            450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
            515                 520                 525

Glu Glu Lys Phe Gly Phe Lys Val Leu Tyr Ala Asp Thr Asp Gly Phe
            530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
            565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
            645                 650                 655

```
Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
            675                 680                 685

Arg Gly Ile Lys Ile Arg Pro Gly Thr Val Ile Ser Tyr Ile Val Leu
            690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
            755                 760                 765

Leu Lys Pro Lys Thr
            770

<210> SEQ ID NO 31
<211> LENGTH: 773
<212> TYPE: PRT
<213> ORGANISM: Artificial sequence
<220> FEATURE:
<223> OTHER INFORMATION: R761Q variant of Thermococcus gorgonarius DNA
      polymerase

<400> SEQUENCE: 31

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240
```

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
        260                 265                 270

Tyr Thr Leu Glu Ala Val Tyr Glu Ala Ile Phe Gly Gln Pro Lys Glu
    275                 280                 285

Lys Val Tyr Ala Glu Glu Ile Ala Gln Ala Trp Glu Thr Gly Glu Gly
290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

```
Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Gln Gln Val Gly Leu Gly Ala Trp
        755                 760                 765

Leu Lys Pro Lys Thr
        770

<210> SEQ ID NO 32
<211> LENGTH: 383
<212> TYPE: PRT
<213> ORGANISM: Artificial sequence
<220> FEATURE:
<223> OTHER INFORMATION: Thermococcus gorgonarius DNA polymerase,
      catalytic domain amino acid sequence

<400> SEQUENCE: 32

Ser Tyr Ala Gly Gly Tyr Val Lys Glu Pro Glu Arg Gly Leu Trp Glu
1               5                   10                  15

Asn Ile Val Tyr Leu Asp Phe Arg Ser Leu Tyr Pro Ser Ile Ile Ile
            20                  25                  30

Thr His Asn Val Ser Pro Asp Thr Leu Asn Arg Glu Gly Cys Glu Glu
        35                  40                  45

Tyr Asp Val Ala Pro Gln Val Gly His Lys Phe Cys Lys Asp Phe Pro
    50                  55                  60

Gly Phe Ile Pro Ser Leu Leu Gly Asp Leu Leu Glu Glu Arg Gln Lys
65                  70                  75                  80

Val Lys Lys Lys Met Lys Ala Thr Ile Asp Pro Ile Glu Lys Lys Leu
                85                  90                  95

Leu Asp Tyr Arg Gln Arg Ala Ile Lys Ile Leu Ala Asn Ser Phe Tyr
            100                 105                 110

Gly Tyr Tyr Gly Tyr Ala Lys Ala Arg Trp Tyr Cys Lys Glu Cys Ala
        115                 120                 125

Glu Ser Val Thr Ala Trp Gly Arg Gln Tyr Ile Glu Thr Thr Ile Arg
    130                 135                 140

Glu Ile Glu Glu Lys Phe Gly Phe Lys Val Leu Tyr Ala Asp Thr Asp
145                 150                 155                 160

Gly Phe Phe Ala Thr Ile Pro Gly Ala Asp Ala Glu Thr Val Lys Lys
                165                 170                 175

Lys Ala Lys Glu Phe Leu Asp Tyr Ile Asn Ala Lys Leu Pro Gly Leu
            180                 185                 190

Leu Glu Leu Glu Tyr Glu Gly Phe Tyr Lys Arg Gly Phe Phe Val Thr
        195                 200                 205

Lys Lys Lys Tyr Ala Val Ile Asp Glu Glu Asp Lys Ile Thr Thr Arg
    210                 215                 220

Gly Leu Glu Ile Val Arg Arg Asp Trp Ser Glu Ile Ala Lys Glu Thr
225                 230                 235                 240
```

Gln Ala Arg Val Leu Glu Ala Ile Leu Lys His Gly Asp Val Glu Glu
                245                 250                 255

Ala Val Arg Ile Val Lys Glu Val Thr Glu Lys Leu Ser Lys Tyr Glu
            260                 265                 270

Val Pro Pro Glu Lys Leu Val Ile Tyr Glu Gln Ile Thr Arg Asp Leu
        275                 280                 285

Lys Asp Tyr Lys Ala Thr Gly Pro His Val Ala Val Ala Lys Arg Leu
290                 295                 300

Ala Ala Arg Gly Ile Lys Ile Arg Pro Gly Thr Val Ile Ser Tyr Ile
305                 310                 315                 320

Val Leu Lys Gly Ser Gly Arg Ile Gly Asp Arg Ala Ile Pro Phe Asp
                325                 330                 335

Glu Phe Asp Pro Ala Lys His Lys Tyr Asp Ala Glu Tyr Tyr Ile Glu
            340                 345                 350

Asn Gln Val Leu Pro Ala Val Glu Arg Ile Leu Arg Ala Phe Gly Tyr
        355                 360                 365

Arg Lys Glu Asp Leu Arg Tyr Gln Lys Thr Arg Gln Val Gly Leu
370                 375                 380

<210> SEQ ID NO 33
<211> LENGTH: 383
<212> TYPE: PRT
<213> ORGANISM: Artificial sequence
<220> FEATURE:
<223> OTHER INFORMATION: R761Q variant of Thermococcus gorgonarius DNA
      polymerase, catalytic domain amino acid sequence

<400> SEQUENCE: 33

Ser Tyr Ala Gly Gly Tyr Val Lys Glu Pro Glu Arg Gly Leu Trp Glu
1               5                   10                  15

Asn Ile Val Tyr Leu Asp Phe Arg Ser Leu Tyr Pro Ser Ile Ile Ile
            20                  25                  30

Thr His Asn Val Ser Pro Asp Thr Leu Asn Arg Glu Gly Cys Glu Glu
        35                  40                  45

Tyr Asp Val Ala Pro Gln Val Gly His Lys Phe Cys Lys Asp Phe Pro
    50                  55                  60

Gly Phe Ile Pro Ser Leu Leu Gly Asp Leu Leu Glu Glu Arg Gln Lys
65                  70                  75                  80

Val Lys Lys Lys Met Lys Ala Thr Ile Asp Pro Ile Glu Lys Lys Leu
                85                  90                  95

Leu Asp Tyr Arg Gln Arg Ala Ile Lys Ile Leu Ala Asn Ser Phe Tyr
            100                 105                 110

Gly Tyr Tyr Gly Tyr Ala Lys Ala Arg Trp Tyr Cys Lys Glu Cys Ala
        115                 120                 125

Glu Ser Val Thr Ala Trp Gly Arg Gln Tyr Ile Glu Thr Thr Ile Arg
    130                 135                 140

Glu Ile Glu Glu Lys Phe Gly Phe Lys Val Leu Tyr Ala Asp Thr Asp
145                 150                 155                 160

Gly Phe Phe Ala Thr Ile Pro Gly Ala Asp Ala Glu Thr Val Lys Lys
                165                 170                 175

Lys Ala Lys Glu Phe Leu Asp Tyr Ile Asn Ala Lys Leu Pro Gly Leu
            180                 185                 190

Leu Glu Leu Glu Tyr Glu Gly Phe Tyr Lys Arg Gly Phe Phe Val Thr
        195                 200                 205

Lys Lys Lys Tyr Ala Val Ile Asp Glu Glu Asp Lys Ile Thr Thr Arg

```
            210                 215                 220
Gly Leu Glu Ile Val Arg Arg Asp Trp Ser Glu Ile Ala Lys Glu Thr
225                 230                 235                 240

Gln Ala Arg Val Leu Glu Ala Ile Leu Lys His Gly Asp Val Glu Glu
                245                 250                 255

Ala Val Arg Ile Val Lys Glu Val Thr Glu Lys Leu Ser Lys Tyr Glu
                260                 265                 270

Val Pro Pro Glu Lys Leu Val Ile Tyr Glu Gln Ile Thr Arg Asp Leu
            275                 280                 285

Lys Asp Tyr Lys Ala Thr Gly Pro His Val Ala Val Ala Lys Arg Leu
290                 295                 300

Ala Ala Arg Gly Ile Lys Ile Arg Pro Gly Thr Val Ile Ser Tyr Ile
305                 310                 315                 320

Val Leu Lys Gly Ser Gly Arg Ile Gly Asp Arg Ala Ile Pro Phe Asp
                325                 330                 335

Glu Phe Asp Pro Ala Lys His Lys Tyr Asp Ala Glu Tyr Tyr Ile Glu
                340                 345                 350

Asn Gln Val Leu Pro Ala Val Glu Arg Ile Leu Arg Ala Phe Gly Tyr
            355                 360                 365

Arg Lys Glu Asp Leu Arg Tyr Gln Lys Thr Gln Gln Val Gly Leu
        370                 375                 380

<210> SEQ ID NO 34
<211> LENGTH: 774
<212> TYPE: PRT
<213> ORGANISM: Thermococcus kodakarensis

<400> SEQUENCE: 34

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205
```

```
Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Lys Glu Leu Ala Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
            610                 615                 620

Arg Val Leu Glu Ala Leu Leu Lys Asp Gly Asp Val Glu Lys Ala Val
```

```
                  625                 630                 635                 640
Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
                660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Ser Ala Trp
                755                 760                 765

Leu Lys Pro Lys Gly Thr
                770

<210> SEQ ID NO 35
<211> LENGTH: 774
<212> TYPE: PRT
<213> ORGANISM: Artificial sequence
<220> FEATURE:
<223> OTHER INFORMATION: R761Q variant of Thermococcus kodakarensis DNA
      polymerase

<400> SEQUENCE: 35

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
                35                  40                  45

Glu Glu Val Lys Lys Ile Thr Ala Glu Arg His Gly Thr Val Val Thr
            50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
                115                 120                 125

Met Glu Gly Asp Glu Glu Leu Lys Met Leu Ala Phe Asp Ile Glu Thr
            130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
                180                 185                 190

Arg Phe Leu Arg Val Val Lys Glu Lys Asp Pro Asp Val Leu Ile Thr
                195                 200                 205
```

```
Tyr Asn Gly Asp Asn Phe Asp Phe Ala Tyr Leu Lys Lys Arg Cys Glu
    210             215                 220

Lys Leu Gly Ile Asn Phe Ala Leu Gly Arg Asp Gly Ser Glu Pro Lys
225             230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
                260             265             270

Tyr Thr Leu Glu Ala Val Tyr Glu Ala Val Phe Gly Gln Pro Lys Glu
        275             280             285

Lys Val Tyr Ala Glu Glu Ile Thr Thr Ala Trp Glu Thr Gly Glu Asn
    290             295             300

Leu Glu Arg Val Ala Arg Tyr Ser Met Glu Asp Ala Lys Val Thr Tyr
305             310             315                 320

Glu Leu Gly Lys Glu Phe Leu Pro Met Glu Ala Gln Leu Ser Arg Leu
                325             330             335

Ile Gly Gln Ser Leu Trp Asp Val Ser Arg Ser Thr Gly Asn Leu
            340             345             350

Val Glu Trp Phe Leu Leu Arg Lys Ala Tyr Glu Arg Asn Glu Leu Ala
        355             360             365

Pro Asn Lys Pro Asp Glu Lys Glu Leu Ala Arg Arg Gln Ser Tyr
    370             375             380

Glu Gly Gly Tyr Val Lys Glu Pro Glu Arg Gly Leu Trp Glu Asn Ile
385             390             395                 400

Val Tyr Leu Asp Phe Arg Ser Leu Tyr Pro Ser Ile Ile Thr His
                405             410             415

Asn Val Ser Pro Asp Thr Leu Asn Arg Glu Gly Cys Lys Glu Tyr Asp
            420             425             430

Val Ala Pro Gln Val Gly His Arg Phe Cys Lys Asp Phe Pro Gly Phe
        435             440             445

Ile Pro Ser Leu Leu Gly Asp Leu Leu Glu Glu Arg Gln Lys Ile Lys
    450             455             460

Lys Lys Met Lys Ala Thr Ile Asp Pro Ile Glu Arg Lys Leu Leu Asp
465             470             475                 480

Tyr Arg Gln Arg Ala Ile Lys Ile Leu Ala Asn Ser Tyr Tyr Gly Tyr
            485             490             495

Tyr Gly Tyr Ala Arg Ala Arg Trp Tyr Cys Lys Glu Cys Ala Glu Ser
        500             505             510

Val Thr Ala Trp Gly Arg Glu Tyr Ile Thr Met Thr Ile Lys Glu Ile
    515             520             525

Glu Glu Lys Tyr Gly Phe Lys Val Ile Tyr Ser Asp Thr Asp Gly Phe
530             535             540

Phe Ala Thr Ile Pro Gly Ala Asp Ala Glu Thr Val Lys Lys Lys Ala
545             550             555             560

Met Glu Phe Leu Lys Tyr Ile Asn Ala Lys Leu Pro Gly Ala Leu Glu
            565             570             575

Leu Glu Tyr Glu Gly Phe Tyr Lys Arg Gly Phe Phe Val Thr Lys Lys
        580             585             590

Lys Tyr Ala Val Ile Asp Glu Glu Gly Lys Ile Thr Thr Arg Gly Leu
    595             600             605

Glu Ile Val Arg Arg Asp Trp Ser Glu Ile Ala Lys Glu Thr Gln Ala
610             615             620

Arg Val Leu Glu Ala Leu Leu Lys Asp Gly Asp Val Glu Lys Ala Val
```

```
               625                 630                 635                 640
     Arg Ile Val Lys Glu Val Thr Glu Lys Leu Ser Lys Tyr Glu Val Pro
                         645                 650                 655

Pro Glu Lys Leu Val Ile His Glu Gln Ile Thr Arg Asp Leu Lys Asp
                 660                 665                 670

Tyr Lys Ala Thr Gly Pro His Val Ala Val Ala Lys Arg Leu Ala Ala
                     675                 680                 685

Arg Gly Val Lys Ile Arg Pro Gly Thr Val Ile Ser Tyr Ile Val Leu
             690                 695                 700

Lys Gly Ser Gly Arg Ile Gly Asp Arg Ala Ile Pro Phe Asp Glu Phe
     705                 710                 715                 720

Asp Pro Thr Lys His Lys Tyr Asp Ala Glu Tyr Tyr Ile Glu Asn Gln
                         725                 730                 735

Val Leu Pro Ala Val Glu Arg Ile Leu Arg Ala Phe Gly Tyr Arg Lys
                 740                 745                 750

Glu Asp Leu Arg Tyr Gln Lys Thr Gln Gln Val Gly Leu Ser Ala Trp
                     755                 760                 765

Leu Lys Pro Lys Gly Thr
             770

<210> SEQ ID NO 36
<211> LENGTH: 383
<212> TYPE: PRT
<213> ORGANISM: Artificial sequence
<220> FEATURE:
<223> OTHER INFORMATION: Thermococcus kodakarensis DNA polymerase,
      catalytic domain amino acid sequence

<400> SEQUENCE: 36

Ser Tyr Glu Gly Gly Tyr Val Lys Glu Pro Glu Arg Gly Leu Trp Glu
     1               5                   10                  15

Asn Ile Val Tyr Leu Asp Phe Arg Ser Leu Tyr Pro Ser Ile Ile Ile
                     20                  25                  30

Thr His Asn Val Ser Pro Asp Thr Leu Asn Arg Glu Gly Cys Lys Glu
                 35                  40                  45

Tyr Asp Val Ala Pro Gln Val Gly His Arg Phe Cys Lys Asp Phe Pro
             50                  55                  60

Gly Phe Ile Pro Ser Leu Leu Gly Asp Leu Leu Glu Glu Arg Gln Lys
     65                  70                  75                  80

Ile Lys Lys Lys Met Lys Ala Thr Ile Asp Pro Ile Glu Arg Lys Leu
                         85                  90                  95

Leu Asp Tyr Arg Gln Arg Ala Ile Lys Ile Leu Ala Asn Ser Tyr Tyr
                     100                 105                 110

Gly Tyr Tyr Gly Tyr Ala Arg Ala Arg Trp Tyr Cys Lys Glu Cys Ala
                 115                 120                 125

Glu Ser Val Thr Ala Trp Gly Arg Glu Tyr Ile Thr Met Thr Ile Lys
             130                 135                 140

Glu Ile Glu Glu Lys Tyr Gly Phe Lys Val Ile Tyr Ser Asp Thr Asp
     145                 150                 155                 160

Gly Phe Phe Ala Thr Ile Pro Gly Ala Asp Ala Glu Thr Val Lys Lys
                         165                 170                 175

Lys Ala Met Glu Phe Leu Lys Tyr Ile Asn Ala Lys Leu Pro Gly Ala
                     180                 185                 190

Leu Glu Leu Glu Tyr Glu Gly Phe Tyr Lys Arg Gly Phe Phe Val Thr
                 195                 200                 205
```

```
Lys Lys Lys Tyr Ala Val Ile Asp Glu Glu Gly Lys Ile Thr Thr Arg
            210                 215                 220

Gly Leu Glu Ile Val Arg Arg Asp Trp Ser Glu Ile Ala Lys Glu Thr
225                 230                 235                 240

Gln Ala Arg Val Leu Glu Ala Leu Leu Lys Asp Gly Asp Val Glu Lys
                245                 250                 255

Ala Val Arg Ile Val Lys Glu Val Thr Glu Lys Leu Ser Lys Tyr Glu
            260                 265                 270

Val Pro Pro Glu Lys Leu Val Ile His Glu Gln Ile Thr Arg Asp Leu
        275                 280                 285

Lys Asp Tyr Lys Ala Thr Gly Pro His Val Ala Val Ala Lys Arg Leu
290                 295                 300

Ala Ala Arg Gly Val Lys Ile Arg Pro Gly Thr Val Ile Ser Tyr Ile
305                 310                 315                 320

Val Leu Lys Gly Ser Gly Arg Ile Gly Asp Arg Ala Ile Pro Phe Asp
                325                 330                 335

Glu Phe Asp Pro Thr Lys His Lys Tyr Asp Ala Glu Tyr Tyr Ile Glu
            340                 345                 350

Asn Gln Val Leu Pro Ala Val Glu Arg Ile Leu Arg Ala Phe Gly Tyr
        355                 360                 365

Arg Lys Glu Asp Leu Arg Tyr Gln Lys Thr Arg Gln Val Gly Leu
370                 375                 380

<210> SEQ ID NO 37
<211> LENGTH: 383
<212> TYPE: PRT
<213> ORGANISM: Artificial sequence
<220> FEATURE:
<223> OTHER INFORMATION: R761Q variant of Thermococcus kodakarensis DNA
      polymerase, catalytic domain amino acid sequence

<400> SEQUENCE: 37

Ser Tyr Glu Gly Gly Tyr Val Lys Glu Pro Glu Arg Gly Leu Trp Glu
1               5                   10                  15

Asn Ile Val Tyr Leu Asp Phe Arg Ser Leu Tyr Pro Ser Ile Ile Ile
            20                  25                  30

Thr His Asn Val Ser Pro Asp Thr Leu Asn Arg Glu Gly Cys Lys Glu
        35                  40                  45

Tyr Asp Val Ala Pro Gln Val Gly His Arg Phe Cys Lys Asp Phe Pro
    50                  55                  60

Gly Phe Ile Pro Ser Leu Leu Gly Asp Leu Leu Glu Glu Arg Gln Lys
65                  70                  75                  80

Ile Lys Lys Lys Met Lys Ala Thr Ile Asp Pro Ile Glu Arg Lys Leu
                85                  90                  95

Leu Asp Tyr Arg Gln Arg Ala Ile Lys Ile Leu Ala Asn Ser Tyr Tyr
            100                 105                 110

Gly Tyr Tyr Gly Tyr Ala Arg Ala Arg Trp Tyr Cys Lys Glu Cys Ala
        115                 120                 125

Glu Ser Val Thr Ala Trp Gly Arg Glu Tyr Ile Thr Met Thr Ile Lys
    130                 135                 140

Glu Ile Glu Glu Lys Tyr Gly Phe Lys Val Ile Tyr Ser Asp Thr Asp
145                 150                 155                 160

Gly Phe Phe Ala Thr Ile Pro Gly Ala Asp Ala Glu Thr Val Lys Lys
                165                 170                 175

Lys Ala Met Glu Phe Leu Lys Tyr Ile Asn Ala Lys Leu Pro Gly Ala
            180                 185                 190
```

```
Leu Glu Leu Glu Tyr Glu Gly Phe Tyr Lys Arg Gly Phe Val Thr
            195                 200                 205
Lys Lys Lys Tyr Ala Val Ile Asp Glu Glu Gly Lys Ile Thr Thr Arg
    210                 215                 220
Gly Leu Glu Ile Val Arg Arg Asp Trp Ser Glu Ile Ala Lys Glu Thr
225                 230                 235                 240
Gln Ala Arg Val Leu Glu Ala Leu Leu Lys Asp Gly Asp Val Glu Lys
                245                 250                 255
Ala Val Arg Ile Val Lys Glu Val Thr Glu Lys Leu Ser Lys Tyr Glu
            260                 265                 270
Val Pro Pro Glu Lys Leu Val Ile His Glu Gln Ile Thr Arg Asp Leu
            275                 280                 285
Lys Asp Tyr Lys Ala Thr Gly Pro His Val Ala Val Ala Lys Arg Leu
    290                 295                 300
Ala Ala Arg Gly Val Lys Ile Arg Pro Gly Thr Val Ile Ser Tyr Ile
305                 310                 315                 320
Val Leu Lys Gly Ser Gly Arg Ile Gly Asp Arg Ala Ile Pro Phe Asp
                325                 330                 335
Glu Phe Asp Pro Thr Lys His Lys Tyr Asp Ala Glu Tyr Tyr Ile Glu
            340                 345                 350
Asn Gln Val Leu Pro Ala Val Glu Arg Ile Leu Arg Ala Phe Gly Tyr
            355                 360                 365
Arg Lys Glu Asp Leu Arg Tyr Gln Lys Thr Gln Gln Val Gly Leu
    370                 375                 380

<210> SEQ ID NO 38
<211> LENGTH: 383
<212> TYPE: PRT
<213> ORGANISM: Artificial sequence
<220> FEATURE:
<223> OTHER INFORMATION: Thermococcus species 9N-7 DNA polymerase,
      catalytic domain amino acid sequence

<400> SEQUENCE: 38

Gly Tyr Ala Gly Gly Tyr Val Lys Glu Pro Glu Arg Gly Leu Trp Asp
1               5                   10                  15
Asn Ile Val Tyr Leu Asp Phe Arg Ser Leu Tyr Pro Ser Ile Ile Ile
            20                  25                  30
Thr His Asn Val Ser Pro Asp Thr Leu Asn Arg Glu Gly Cys Lys Glu
        35                  40                  45
Tyr Asp Val Ala Pro Glu Val Gly His Lys Phe Cys Lys Asp Phe Pro
    50                  55                  60
Gly Phe Ile Pro Ser Leu Leu Gly Asp Leu Leu Glu Glu Arg Gln Lys
65                  70                  75                  80
Ile Lys Arg Lys Met Lys Ala Thr Val Asp Pro Leu Glu Lys Lys Leu
                85                  90                  95
Leu Asp Tyr Arg Gln Arg Ala Ile Lys Ile Leu Ala Asn Ser Phe Tyr
            100                 105                 110
Gly Tyr Tyr Gly Tyr Ala Lys Ala Arg Trp Tyr Cys Lys Glu Cys Ala
        115                 120                 125
Glu Ser Val Thr Ala Trp Gly Arg Glu Tyr Ile Glu Met Val Ile Arg
    130                 135                 140
Glu Leu Glu Glu Lys Phe Gly Phe Lys Val Leu Tyr Ala Asp Thr Asp
145                 150                 155                 160
Gly Leu His Ala Thr Ile Pro Gly Ala Asp Ala Glu Thr Val Lys Lys
```

```
            165                 170                 175
Lys Ala Lys Glu Phe Leu Lys Tyr Ile Asn Pro Lys Leu Pro Gly Leu
            180                 185                 190

Leu Glu Leu Glu Tyr Glu Gly Phe Tyr Val Arg Gly Phe Val Thr
            195                 200                 205

Lys Lys Lys Tyr Ala Val Ile Asp Glu Glu Gly Lys Ile Thr Thr Arg
        210                 215                 220

Gly Leu Glu Ile Val Arg Arg Asp Trp Ser Glu Ile Ala Lys Glu Thr
225                 230                 235                 240

Gln Ala Arg Val Leu Glu Ala Ile Leu Lys His Gly Asp Val Glu Glu
            245                 250                 255

Ala Val Arg Ile Val Lys Glu Val Thr Glu Lys Leu Ser Lys Tyr Glu
            260                 265                 270

Val Pro Pro Glu Lys Leu Val Ile His Glu Gln Ile Thr Arg Asp Leu
        275                 280                 285

Arg Asp Tyr Lys Ala Thr Gly Pro His Val Ala Val Ala Lys Arg Leu
        290                 295                 300

Ala Ala Arg Gly Val Lys Ile Arg Pro Gly Thr Val Ile Ser Tyr Ile
305                 310                 315                 320

Val Leu Lys Gly Ser Gly Arg Ile Gly Asp Arg Ala Ile Pro Ala Asp
                325                 330                 335

Glu Phe Asp Pro Thr Lys His Arg Tyr Asp Ala Glu Tyr Tyr Ile Glu
            340                 345                 350

Asn Gln Val Leu Pro Ala Val Glu Arg Ile Leu Lys Ala Phe Gly Tyr
            355                 360                 365

Arg Lys Glu Asp Leu Arg Tyr Gln Lys Thr Lys Gln Val Gly Leu
        370                 375                 380

<210> SEQ ID NO 39
<211> LENGTH: 383
<212> TYPE: PRT
<213> ORGANISM: Artificial sequence
<220> FEATURE:
<223> OTHER INFORMATION: K761Q variant of Thermococcus species 9N-7 DNA
      polymerase, catalytic domain amino acid sequence

<400> SEQUENCE: 39

Gly Tyr Ala Gly Gly Tyr Val Lys Glu Pro Glu Arg Gly Leu Trp Asp
1               5                   10                  15

Asn Ile Val Tyr Leu Asp Phe Arg Ser Leu Tyr Pro Ser Ile Ile Ile
            20                  25                  30

Thr His Asn Val Ser Pro Asp Thr Leu Asn Arg Glu Gly Cys Lys Glu
        35                  40                  45

Tyr Asp Val Ala Pro Glu Val Gly His Lys Phe Cys Lys Asp Phe Pro
    50                  55                  60

Gly Phe Ile Pro Ser Leu Leu Gly Asp Leu Leu Glu Glu Arg Gln Lys
65                  70                  75                  80

Ile Lys Arg Lys Met Lys Ala Thr Val Asp Pro Leu Glu Lys Lys Leu
                85                  90                  95

Leu Asp Tyr Arg Gln Arg Ala Ile Lys Ile Leu Ala Asn Ser Phe Tyr
            100                 105                 110

Gly Tyr Tyr Gly Tyr Ala Lys Ala Arg Trp Tyr Cys Lys Glu Cys Ala
        115                 120                 125

Glu Ser Val Thr Ala Trp Gly Arg Glu Tyr Ile Glu Met Val Ile Arg
    130                 135                 140
```

Glu Leu Glu Glu Lys Phe Gly Phe Lys Val Leu Tyr Ala Asp Thr Asp
145                 150                 155                 160

Gly Leu His Ala Thr Ile Pro Gly Ala Asp Ala Glu Thr Val Lys Lys
            165                 170                 175

Lys Ala Lys Glu Phe Leu Lys Tyr Ile Asn Pro Lys Leu Pro Gly Leu
        180                 185                 190

Leu Glu Leu Glu Tyr Glu Gly Phe Tyr Val Arg Gly Phe Phe Val Thr
    195                 200                 205

Lys Lys Lys Tyr Ala Val Ile Asp Glu Glu Gly Lys Ile Thr Thr Arg
210                 215                 220

Gly Leu Glu Ile Val Arg Arg Asp Trp Ser Glu Ile Ala Lys Glu Thr
225                 230                 235                 240

Gln Ala Arg Val Leu Glu Ala Ile Leu Lys His Gly Asp Val Glu Glu
            245                 250                 255

Ala Val Arg Ile Val Lys Glu Val Thr Glu Lys Leu Ser Lys Tyr Glu
        260                 265                 270

Val Pro Pro Glu Lys Leu Val Ile His Glu Gln Ile Thr Arg Asp Leu
    275                 280                 285

Arg Asp Tyr Lys Ala Thr Gly Pro His Val Ala Val Ala Lys Arg Leu
290                 295                 300

Ala Ala Arg Gly Val Lys Ile Arg Pro Gly Thr Val Ile Ser Tyr Ile
305                 310                 315                 320

Val Leu Lys Gly Ser Gly Arg Ile Gly Asp Arg Ala Ile Pro Ala Asp
            325                 330                 335

Glu Phe Asp Pro Thr Lys His Arg Tyr Asp Ala Glu Tyr Tyr Ile Glu
        340                 345                 350

Asn Gln Val Leu Pro Ala Val Glu Arg Ile Leu Lys Ala Phe Gly Tyr
    355                 360                 365

Arg Lys Glu Asp Leu Arg Tyr Gln Lys Thr Gln Gln Val Gly Leu
370                 375                 380

<210> SEQ ID NO 40
<211> LENGTH: 775
<212> TYPE: PRT
<213> ORGANISM: Thermococcusspecies9N-7

<400> SEQUENCE: 40

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
            85                  90                  95

Arg Asp Arg Ile Arg Ala His Pro Ala Val Val Asp Ile Tyr Glu Tyr
        100                 105                 110

Asp Ile Pro Phe Ala Lys Arg Tyr Leu Ile Asp Lys Gly Leu Ile Pro
    115                 120                 125

Met Glu Gly Asp Glu Glu Leu Thr Met Leu Ala Phe Asp Ile Glu Thr
130                 135                 140

```
Leu Tyr His Glu Gly Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
        165                 170                 175

Asp Leu Pro Tyr Val Asp Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Cys Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
        290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
            405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
        530                 535                 540

His Ala Thr Ile Pro Gly Ala Asp Ala Glu Thr Val Lys Lys Lys Ala
545                 550                 555                 560
```

```
Lys Glu Phe Leu Lys Tyr Ile Asn Pro Lys Leu Pro Gly Leu Leu Glu
                565                 570                 575
Leu Glu Tyr Glu Gly Phe Tyr Val Arg Gly Phe Phe Val Thr Lys Lys
            580                 585                 590
Lys Tyr Ala Val Ile Asp Glu Glu Gly Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Arg Asp
            660                 665                 670
Tyr Lys Ala Thr Gly Pro His Val Ala Val Ala Lys Arg Leu Ala Ala
        675                 680                 685
Arg Gly Val Lys Ile Arg Pro Gly Thr Val Ile Ser Tyr Ile Val Leu
    690                 695                 700
Lys Gly Ser Gly Arg Ile Gly Asp Arg Ala Ile Pro Ala Asp Glu Phe
705                 710                 715                 720
Asp Pro Thr Lys His Arg Tyr Asp Ala Glu Tyr Tyr Ile Glu Asn Gln
                725                 730                 735
Val Leu Pro Ala Val Glu Arg Ile Leu Lys Ala Phe Gly Tyr Arg Lys
            740                 745                 750
Glu Asp Leu Arg Tyr Gln Lys Thr Lys Gln Val Gly Leu Gly Ala Trp
        755                 760                 765
Leu Lys Val Lys Gly Lys Lys
    770                 775

<210> SEQ ID NO 41
<211> LENGTH: 775
<212> TYPE: PRT
<213> ORGANISM: Artificial sequence
<220> FEATURE:
<223> OTHER INFORMATION: K761Q variant of Thermococcus species 9N-7 DNA
      polymerase

<400> SEQUENCE: 41

Met Ile Leu Asp Thr Asp Tyr Ile Thr Glu Asn Gly Lys Pro Val Ile
1               5                   10                  15
Arg Val Phe Lys Lys Glu Asn Gly Glu Phe Lys Ile Glu Tyr Asp Arg
            20                  25                  30
Thr Phe Glu Pro Tyr Phe Tyr Ala Leu Leu Lys Asp Asp Ser Ala Ile
        35                  40                  45
Glu Asp Val Lys Lys Val Thr Ala Lys Arg His Gly Thr Val Val Lys
    50                  55                  60
Val Lys Arg Ala Glu Lys Val Gln Lys Lys Phe Leu Gly Arg Pro Ile
65                  70                  75                  80
Glu Val Trp Lys Leu Tyr Phe Asn His Pro Gln Asp Val Pro Ala Ile
                85                  90                  95
Arg Asp Arg Ile Arg Ala His Pro Ala Val Val Asp Ile Tyr Glu Tyr
            100                 105                 110
Asp Ile Pro Phe Ala Lys Arg Tyr Leu Ile Asp Lys Gly Leu Ile Pro
        115                 120                 125
Met Glu Gly Asp Glu Glu Leu Thr Met Leu Ala Phe Asp Ile Glu Thr
    130                 135                 140
```

```
Leu Tyr His Glu Gly Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
            165                 170                 175

Asp Leu Pro Tyr Val Asp Val Val Ser Thr Glu Lys Glu Met Ile Lys
                180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Cys Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560
```

-continued

```
Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Gln Gln Val Gly Leu Gly Ala Trp
        755                 760                 765

Leu Lys Val Lys Gly Lys Lys
    770                 775

<210> SEQ ID NO 42
<211> LENGTH: 63
<212> TYPE: PRT
<213> ORGANISM: Artificial sequence
<220> FEATURE:
<223> OTHER INFORMATION: Sso7d SNS-dsDBD amino acid sequence of
      Sulfolobus solfataricus (see US 6,627,424)

<400> SEQUENCE: 42

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60

<210> SEQ ID NO 43
<211> LENGTH: 65
<212> TYPE: PRT
<213> ORGANISM: Artificial sequence
<220> FEATURE:
<223> OTHER INFORMATION: Sac7d SNS-dsDBD amino acid sequence of
      Sulfolobus acidocaldarius

<400> SEQUENCE: 43

Val Lys Val Lys Phe Lys Tyr Lys Gly Glu Glu Lys Glu Val Asp Thr
1               5                   10                  15
```

Ser Lys Ile Lys Lys Val Trp Arg Val Gly Lys Met Val Ser Phe Thr
             20                  25                  30

Tyr Asp Asp Asn Gly Lys Thr Gly Arg Gly Ala Val Ser Glu Lys Asp
             35                  40                  45

Ala Pro Lys Glu Leu Leu Asp Met Leu Ala Arg Ala Glu Arg Glu Lys
 50                  55                  60

Lys
 65

<210> SEQ ID NO 44
<211> LENGTH: 56
<212> TYPE: PRT
<213> ORGANISM: Artificial sequence
<220> FEATURE:
<223> OTHER INFORMATION: Pyrobaculum aerophilum Pae3192 amino acid
      sequence

<400> SEQUENCE: 44

Ser Lys Lys Gln Lys Leu Lys Phe Tyr Asp Ile Lys Ala Lys Gln Ala
 1               5                  10                  15

Phe Glu Thr Asp Gln Tyr Glu Val Ile Glu Lys Gln Thr Ala Arg Gly
             20                  25                  30

Pro Met Met Phe Ala Val Ala Lys Ser Pro Tyr Thr Gly Ile Lys Val
             35                  40                  45

Tyr Arg Leu Leu Gly Lys Lys Lys
 50                  55

<210> SEQ ID NO 45
<211> LENGTH: 55
<212> TYPE: PRT
<213> ORGANISM: Artificial sequence
<220> FEATURE:
<223> OTHER INFORMATION: Pyrobaculum aerophilum Pae0384 amino acid
      sequence

<400> SEQUENCE: 45

Ala Lys Gln Lys Leu Lys Phe Tyr Asp Ile Lys Ala Lys Gln Ser Phe
 1               5                  10                  15

Glu Thr Asp Lys Tyr Glu Val Ile Glu Lys Glu Thr Ala Arg Gly Pro
             20                  25                  30

Met Leu Phe Ala Val Ala Thr Ser Pro Tyr Thr Gly Ile Lys Val Tyr
             35                  40                  45

Arg Leu Leu Gly Lys Lys Lys
 50                  55

<210> SEQ ID NO 46
<211> LENGTH: 55
<212> TYPE: PRT
<213> ORGANISM: Artificial sequence
<220> FEATURE:
<223> OTHER INFORMATION: Aeropyrum pernix Ape3192 amino acid sequence

<400> SEQUENCE: 46

Pro Lys Lys Glu Lys Ile Lys Phe Phe Asp Leu Val Ala Lys Lys Tyr
 1               5                  10                  15

Tyr Glu Thr Asp Asn Tyr Glu Val Glu Ile Lys Glu Thr Lys Arg Gly
             20                  25                  30

Lys Phe Arg Phe Ala Lys Ala Lys Ser Pro Tyr Thr Gly Lys Ile Phe
             35                  40                  45

Tyr Arg Val Leu Gly Lys Ala
 50                  55

<210> SEQ ID NO 47
<211> LENGTH: 59
<212> TYPE: PRT
<213> ORGANISM: Artificial sequence
<220> FEATURE:
<223> OTHER INFORMATION: HmfA HMf family archaeal histone amino acid
      sequence of Methanothermus fervidus

<400> SEQUENCE: 47

Gly Glu Leu Pro Ile Ala Pro Ile Gly Arg Ile Ile Lys Asn Ala Gly
1               5                   10                  15

Ala Glu Arg Val Ser Asp Asp Ala Arg Ile Ala Leu Ala Lys Val Leu
            20                  25                  30

Glu Glu Met Gly Glu Glu Ile Ala Ser Glu Ala Val Lys Leu Ala Lys
        35                  40                  45

His Ala Gly Arg Lys Thr Ile Lys Ala Glu Asp
    50                  55

<210> SEQ ID NO 48
<211> LENGTH: 59
<212> TYPE: PRT
<213> ORGANISM: Artificial sequence
<220> FEATURE:
<223> OTHER INFORMATION: HMfB HMf family archaeal histone amino acid
      sequence of Methanothermus fervidus

<400> SEQUENCE: 48

Glu Leu Pro Ile Ala Pro Ile Gly Arg Ile Ile Lys Asp Ala Gly Ala
1               5                   10                  15

Glu Arg Val Ser Asp Asp Ala Arg Ile Thr Leu Ala Lys Ile Leu Glu
            20                  25                  30

Glu Met Gly Arg Asp Ile Ala Ser Glu Ala Ile Lys Leu Ala Arg His
        35                  40                  45

Ala Gly Arg Lys Thr Ile Lys Ala Glu Asp Ile
    50                  55

<210> SEQ ID NO 49
<211> LENGTH: 59
<212> TYPE: PRT
<213> ORGANISM: Artificial sequence
<220> FEATURE:
<223> OTHER INFORMATION: HpyA1 HMf family archaeal histone amino acid
      sequence of Pyrococcus strain GB-3a

<400> SEQUENCE: 49

Gly Glu Leu Pro Ile Ala Pro Val Asp Arg Leu Ile Arg Lys Ala Gly
1               5                   10                  15

Ala Glu Arg Val Ser Glu Glu Ala Ala Lys Ile Leu Ala Glu Tyr Leu
            20                  25                  30

Glu Glu Tyr Ala Ile Glu Val Ser Lys Lys Ala Val Glu Phe Ala Arg
        35                  40                  45

His Ala Gly Arg Lys Thr Val Lys Ala Glu Asp
    50                  55

<210> SEQ ID NO 50
<211> LENGTH: 59
<212> TYPE: PRT
<213> ORGANISM: Artificial sequence
<220> FEATURE:
<223> OTHER INFORMATION: HpyA2 HMf family archaeal histone amino acid
      sequence of Pyrococcus strain GB-3a

```
<400> SEQUENCE: 50

Ala Glu Leu Pro Ile Ala Pro Val Asp Arg Leu Ile Arg Lys Ala Gly
1               5                   10                  15

Ala Gln Arg Val Ser Glu Gln Ala Ala Lys Leu Leu Ala Glu His Leu
            20                  25                  30

Glu Glu Lys Ala Leu Glu Ile Ala Arg Lys Ala Val Asp Leu Ala Lys
        35                  40                  45

His Ala Gly Arg Lys Thr Val Lys Ala Glu Asp
    50                  55

<210> SEQ ID NO 51
<211> LENGTH: 62
<212> TYPE: PRT
<213> ORGANISM: Artificial sequence
<220> FEATURE:
<223> OTHER INFORMATION: Sso7d sequence non-specific DNA-binding domain
      amino acid sequence

<400> SEQUENCE: 51

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys
    50                  55                  60

<210> SEQ ID NO 52
<211> LENGTH: 194
<212> TYPE: PRT
<213> ORGANISM: Artificial sequence
<220> FEATURE:
<223> OTHER INFORMATION: Pyrococcus 3'-5' exonuclease domain amino acid
      sequence

<400> SEQUENCE: 52

Glu Glu Leu Lys Leu Leu Ala Phe Asp Ile Glu Thr Leu Tyr His Glu
1               5                   10                  15

Gly Glu Glu Phe Gly Lys Gly Pro Ile Ile Met Ile Ser Tyr Ala Asp
            20                  25                  30

Glu Glu Glu Ala Lys Val Ile Thr Trp Lys Lys Ile Asp Leu Pro Tyr
        35                  40                  45

Val Glu Val Val Ser Ser Glu Arg Glu Met Ile Lys Arg Phe Leu Lys
    50                  55                  60

Ile Ile Arg Glu Lys Asp Pro Asp Ile Ile Thr Tyr Asn Gly Asp
65                  70                  75                  80

Ser Phe Asp Leu Pro Tyr Leu Ala Lys Arg Ala Glu Lys Leu Gly Ile
                85                  90                  95

Lys Leu Thr Ile Gly Arg Asp Gly Ser Glu Pro Lys Met Gln Arg Ile
            100                 105                 110

Gly Asp Met Thr Ala Val Glu Val Lys Gly Arg Ile His Phe Asp Leu
        115                 120                 125

Tyr His Val Ile Arg Arg Thr Ile Asn Leu Pro Thr Tyr Thr Leu Glu
    130                 135                 140

Ala Val Tyr Glu Ala Ile Phe Gly Lys Pro Lys Glu Lys Val Tyr Ala
145                 150                 155                 160

Asp Glu Ile Ala Lys Ala Trp Glu Thr Gly Glu Gly Leu Glu Arg Val
```

Ala Lys Tyr Ser Met Glu Asp Ala Lys Ala Thr Tyr Glu Leu Gly Lys
            165                 170                 175
        180                 185                 190

Glu Phe

<210> SEQ ID NO 53
<211> LENGTH: 103
<212> TYPE: PRT
<213> ORGANISM: Artificial sequence
<220> FEATURE:
<223> OTHER INFORMATION: 2A7 antibody light chain variable region

<400> SEQUENCE: 53

Thr Gln Ser Pro Ala Ser Leu Ala Val Ser Leu Gly Gln Arg Ala Thr
1               5                   10                  15

Ile Ser Tyr Arg Ala Ser Lys Ser Val Ser Thr Ser Gly Tyr Ser Tyr
            20                  25                  30

Met His Trp Asn Gln Gln Lys Pro Gly Gln Pro Pro Arg Leu Leu Ile
        35                  40                  45

Tyr Leu Val Ser Asn Leu Glu Ser Gly Val Pro Ala Arg Phe Ser Gly
    50                  55                  60

Ser Gly Ser Gly Thr Asp Phe Thr Leu Asn Ile His Pro Val Glu Glu
65                  70                  75                  80

Glu Asp Ala Ala Thr Tyr Tyr Cys Gln His Ile Arg Glu Leu Thr Arg
                85                  90                  95

Ser Glu Gly Gly Pro Ser Trp
            100

<210> SEQ ID NO 54
<211> LENGTH: 104
<212> TYPE: PRT
<213> ORGANISM: Artificial sequence
<220> FEATURE:
<223> OTHER INFORMATION: 2A7 antibody heavy chain variable region

<400> SEQUENCE: 54

Gly Pro Gly Leu Val Ala Pro Ser Gln Ser Leu Ser Ile Thr Cys Thr
1               5                   10                  15

Val Ser Gly Phe Ser Leu Thr Asp Tyr Gly Val Ser Trp Val Arg Gln
            20                  25                  30

Ser Pro Gly Gln Gly Leu Glu Trp Leu Gly Ile Ile Trp Gly Asp Gly
        35                  40                  45

Ser Thr Asp Tyr His Ser Ser Leu Ile Ser Arg Leu Arg Ile Ser Lys
    50                  55                  60

Asp Asn Ser Lys Ser Gln Val Phe Leu Lys Leu Asn Ser Leu Gln Thr
65                  70                  75                  80

Asp Asp Thr Ala Thr Tyr Tyr Cys Ala Arg Pro Val Ile Gly Asn Tyr
                85                  90                  95

Ala Met Asp Tyr Trp Gly Gln Gly
            100

<210> SEQ ID NO 55
<211> LENGTH: 101
<212> TYPE: PRT
<213> ORGANISM: Artificial sequence
<220> FEATURE:
<223> OTHER INFORMATION: 5D3 antibody light chain variable region

<400> SEQUENCE: 55

Thr Gln Ser Pro Ala Ser Leu Ala Val Ser Leu Gly Gln Arg Ala Thr
1               5                   10                  15

Ile Ser Cys Arg Ala Ser Glu Ser Val Glu Tyr Tyr Gly Thr Arg Leu
                20                  25                  30

Met Gln Trp Tyr Gln Gln Lys Pro Gly Lys Ala Pro Lys Leu Leu Ile
            35                  40                  45

Tyr Gly Ala Ser Asn Val Glu Ser Gly Val Pro Ala Arg Phe Ser Gly
        50                  55                  60

Ser Gly Ser Gly Thr Asp Phe Ser Leu Asn Ile His Pro Val Glu Glu
65                  70                  75                  80

Asp Asp Phe Ala Met Tyr Phe Cys Gln Gln Ser Arg Lys Val Pro Trp
                85                  90                  95

Thr Phe Gly Gly Gly
            100

<210> SEQ ID NO 56
<211> LENGTH: 105
<212> TYPE: PRT
<213> ORGANISM: Artificial sequence
<220> FEATURE:
<223> OTHER INFORMATION: 5D3 antibody heavy chain variable region

<400> SEQUENCE: 56

Ser Gly Pro Gly Leu Val Ala Pro Ser Gln Ser Leu Ser Ile Thr Cys
1               5                   10                  15

Thr Val Ser Gly Phe Ser Leu Thr Asp Tyr Gly Val Ser Trp Val Arg
                20                  25                  30

Gln Ser Pro Gly Gln Gly Leu Glu Trp Leu Gly Ile Ile Trp Gly Asp
            35                  40                  45

Gly Ser Thr Asp Tyr His Ser Ser Leu Ile Ser Arg Leu Arg Ile Ser
        50                  55                  60

Lys Asp Asn Ser Lys Ser Gln Val Phe Leu Lys Leu Asn Ser Leu Gln
65                  70                  75                  80

Thr Asp Asp Thr Ala Thr Tyr Tyr Cys Ala Arg Pro Val Ile Gly Asn
                85                  90                  95

Tyr Ala Met Asp Tyr Trp Gly Gln Gly
            100                 105

<210> SEQ ID NO 57
<211> LENGTH: 15
<212> TYPE: PRT
<213> ORGANISM: Artificial sequence
<220> FEATURE:
<223> OTHER INFORMATION: 2A7 antibody light chain CDR-L1

<400> SEQUENCE: 57

Arg Ala Ser Lys Ser Val Ser Thr Ser Gly Tyr Ser Tyr Met His
1               5                   10                  15

<210> SEQ ID NO 58
<211> LENGTH: 7
<212> TYPE: PRT
<213> ORGANISM: Artificial sequence
<220> FEATURE:
<223> OTHER INFORMATION: 2A7 antibody light chain CDR-L2

<400> SEQUENCE: 58

Leu Val Ser Asn Leu Glu Ser
1               5

```
<210> SEQ ID NO 59
<211> LENGTH: 9
<212> TYPE: PRT
<213> ORGANISM: Artificial sequence
<220> FEATURE:
<223> OTHER INFORMATION: 2A7 antibody light chain CDR-L3

<400> SEQUENCE: 59

Gln His Ile Arg Glu Leu Thr Arg Ser
1               5

<210> SEQ ID NO 60
<211> LENGTH: 9
<212> TYPE: PRT
<213> ORGANISM: Artificial sequence
<220> FEATURE:
<223> OTHER INFORMATION: 2A7 antibody heavy chain CDR-H1

<400> SEQUENCE: 60

Phe Ser Leu Thr Asp Tyr Gly Val Ser
1               5

<210> SEQ ID NO 61
<211> LENGTH: 18
<212> TYPE: PRT
<213> ORGANISM: Artificial sequence
<220> FEATURE:
<223> OTHER INFORMATION: 2A7 antibody heavy chain CDR-H2

<400> SEQUENCE: 61

Ile Ile Trp Gly Asp Gly Ser Thr Asp Tyr His Ser Ser Leu Ile Ser
1               5                   10                  15

Arg Leu

<210> SEQ ID NO 62
<211> LENGTH: 10
<212> TYPE: PRT
<213> ORGANISM: Artificial sequence
<220> FEATURE:
<223> OTHER INFORMATION: 2A7 antibody heavy chain CDR-H3

<400> SEQUENCE: 62

Pro Val Ile Gly Asn Tyr Ala Met Asp Tyr
1               5                   10

<210> SEQ ID NO 63
<211> LENGTH: 15
<212> TYPE: PRT
<213> ORGANISM: Artificial sequence
<220> FEATURE:
<223> OTHER INFORMATION: 5D3 antibody light chain CDR-L1

<400> SEQUENCE: 63

Arg Ala Ser Glu Ser Val Glu Tyr Tyr Gly Thr Arg Leu Met Gln
1               5                   10                  15

<210> SEQ ID NO 64
<211> LENGTH: 7
<212> TYPE: PRT
<213> ORGANISM: Artificial sequence
<220> FEATURE:
<223> OTHER INFORMATION: 5D3 antibody light chain CDR-L2

<400> SEQUENCE: 64

Gly Ala Ser Asn Val Glu Ser
1               5
```

<210> SEQ ID NO 65
<211> LENGTH: 9
<212> TYPE: PRT
<213> ORGANISM: Artificial sequence
<220> FEATURE:
<223> OTHER INFORMATION: 5D3 antibody light chain CDR-L3

<400> SEQUENCE: 65

Gln Gln Ser Arg Lys Val Pro Trp Thr
1               5

<210> SEQ ID NO 66
<211> LENGTH: 9
<212> TYPE: PRT
<213> ORGANISM: Artificial sequence
<220> FEATURE:
<223> OTHER INFORMATION: 5D3 antibody heavy chain CDR-H1

<400> SEQUENCE: 66

Phe Ser Leu Thr Asp Tyr Gly Val Ser
1               5

<210> SEQ ID NO 67
<211> LENGTH: 18
<212> TYPE: PRT
<213> ORGANISM: Artificial sequence
<220> FEATURE:
<223> OTHER INFORMATION: 5D3 antibody heavy chain CDR-H2

<400> SEQUENCE: 67

Ile Ile Trp Gly Asp Gly Ser Thr Asp Tyr His Ser Ser Leu Ile Ser
1               5                   10                  15

Arg Leu

<210> SEQ ID NO 68
<211> LENGTH: 10
<212> TYPE: PRT
<213> ORGANISM: Artificial sequence
<220> FEATURE:
<223> OTHER INFORMATION: 5D3 antibody heavy chain CDR-H3

<400> SEQUENCE: 68

Pro Val Ile Gly Asn Tyr Ala Met Asp Tyr
1               5                   10

<210> SEQ ID NO 69
<211> LENGTH: 766
<212> TYPE: PRT
<213> ORGANISM: Artificial sequence
<220> FEATURE:
<223> OTHER INFORMATION: Pyrococcus DNA polymerase sequence including
      exonuclease domain and catalytic domain

<400> SEQUENCE: 69

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
                20                  25                  30

Thr Phe Arg Pro Tyr Ile Tyr Ala Leu Leu Lys Asp Asp Ser Lys Ile
            35                  40                  45

Glu Glu Val Lys Lys Ile Thr Ala Glu Arg His Gly Lys Ile Val Arg
        50                  55                  60

Ile Val Asp Ala Glu Lys Val Glu Lys Lys Phe Leu Gly Arg Pro Ile
65                  70                  75                  80

```
Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
                100                 105                 110

Asp Ile Pro Phe Ala Lys Arg Tyr Leu Ile Asp Lys Gly Leu Ile Pro
                115                 120                 125

Met Glu Gly Asp Glu Glu Leu Lys Leu Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Ser Ser Glu Arg Glu Met Ile Lys
                180                 185                 190

Arg Phe Leu Lys Ile Ile Arg Glu Lys Asp Pro Asp Ile Ile Ile Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Arg Glu Tyr Glu Arg Arg Leu Arg Glu Ser
    370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
                420                 425                 430

Asp Val Ala Pro Glu Val Gly His Lys Phe Cys Lys Asp Phe Pro Gly
                435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495
```

```
Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu
        755                 760                 765

<210> SEQ ID NO 70
<211> LENGTH: 766
<212> TYPE: PRT
<213> ORGANISM: Artificial sequence
<220> FEATURE:
<223> OTHER INFORMATION: Pyrococcus DNA polymerase sequence including
      exonuclease domain and catalytic domain, K762Q

<400> SEQUENCE: 70

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95
```

-continued

```
Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
            130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Ile Ile Arg Glu Lys Asp Pro Asp Ile Ile Ile Thr
            195                 200                 205

Tyr Asn Gly Asp Ser Phe Asp Leu Pro Tyr Leu Ala Lys Arg Ala Glu
            210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Thr Gly Glu Gly
            290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
            370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Lys Ile
            450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510
```

Ser Val Thr Ala Trp Gly Arg Glu Tyr Ile Glu Phe Val Trp Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Gln Gln Thr Gly Leu
        755                 760                 765

<210> SEQ ID NO 71
<211> LENGTH: 766
<212> TYPE: PRT
<213> ORGANISM: Artificial sequence
<220> FEATURE:
<223> OTHER INFORMATION: Pyrococcus DNA polymerase sequence including
      exonuclease domain and catalytic domain, A408S K762Q

<400> SEQUENCE: 71

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

```
Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Ile Ile Arg Glu Lys Asp Pro Asp Ile Ile Ile Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525
```

-continued

```
Leu Glu Glu Lys Phe Gly Phe Lys Val Leu Tyr Ile Asp Thr Asp Gly
    530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
                580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Trp Gln Lys Thr Gln Gln Thr Gly Leu
            755                 760                 765

<210> SEQ ID NO 72
<211> LENGTH: 22
<212> TYPE: DNA
<213> ORGANISM: Artificial Sequence
<220> FEATURE:
<223> OTHER INFORMATION: primer

<400> SEQUENCE: 72
gccagggttt tcccagtcac ga                                              22
```